(12) United States Patent
Ritchie et al.

(10) Patent No.: US 10,697,969 B2
(45) Date of Patent: Jun. 30, 2020

(54) METHODS FOR DIAGNOSING A COLORECTAL CANCER (CRC) HEALTH STATE OR CHANGE IN CRC HEALTH STATE, OR FOR DIAGNOSING RISK OF DEVELOPING CRC OR THE PRESENCE OF CRC IN A SUBJECT

(71) Applicant: MED-LIFE DISCOVERIES LP, Saskatoon (CA)

(72) Inventors: Shawn Ritchie, Saskatoon (CA); Dayan Goodenowe, Saskatoon (CA)

(73) Assignee: MED-LIFE DISCOVERIES LP, Saskatoon, Saskatchewan (CA)

( * ) Notice: Subject to any disclaimer, the term of this patent is extended or adjusted under 35 U.S.C. 154(b) by 394 days.

(21) Appl. No.: 15/192,522

(22) Filed: Jun. 24, 2016

(65) Prior Publication Data
US 2016/0377622 A1   Dec. 29, 2016

Related U.S. Application Data

(63) Continuation of application No. 11/910,942, filed as application No. PCT/CA2006/001502 on Sep. 12, 2006, now abandoned.

(60) Provisional application No. 60/804,764, filed on Jun. 14, 2006, provisional application No. 60/716,310, filed on Sep. 12, 2005.

(51) Int. Cl.
| | |
|---|---|
| *G01N 33/48* | (2006.01) |
| *G01N 33/50* | (2006.01) |
| *G01N 33/574* | (2006.01) |
| *G01N 33/82* | (2006.01) |

(52) U.S. Cl.
CPC . *G01N 33/57419* (2013.01); *G01N 33/57449* (2013.01); *G01N 33/57484* (2013.01); *G01N 33/82* (2013.01)

(58) Field of Classification Search
None
See application file for complete search history.

(56) References Cited

U.S. PATENT DOCUMENTS

| | | | |
|---|---|---|---|
| 4,956,788 | A | 9/1990 | Guan et al. |
| 4,978,852 | A | 12/1990 | Williams et al. |
| 5,233,190 | A | 8/1993 | Schlereth et al. |
| 6,329,146 | B1 | 12/2001 | Crooke et al. |
| 6,677,114 | B1 | 1/2004 | Schneider et al. |
| 6,680,203 | B2 | 1/2004 | Dasseux et al. |
| 7,005,255 | B2 | 2/2006 | Kaddurah-Daouk et al. |
| 2002/0009394 | A1 | 1/2002 | Kostler et al. |
| 2002/0009740 | A1 | 1/2002 | Kaddurah-Daouk et al. |
| 2002/0019023 | A1 | 2/2002 | Dasseux et al. |
| 2003/0108876 | A1 | 6/2003 | Speir |
| 2003/0134304 | A1 | 7/2003 | Van Der Greef |
| 2003/0232446 | A1 | 12/2003 | Scholl et al. |
| 2004/0029120 | A1 | 2/2004 | Goodenowe |
| 2004/0121327 | A1 | 6/2004 | Manns |
| 2004/0146853 | A1 | 7/2004 | Kaddurah-Daouk et al. |
| 2005/0014132 | A1 | 1/2005 | Kaddurah-Daouk et al. |
| 2006/0134676 | A1 | 6/2006 | Kaddurah-Daouk et al. |
| 2006/0134677 | A1 | 6/2006 | Kaddurah-Daouk et al. |
| 2006/0134678 | A1 | 6/2006 | Kaddurah-Daouk et al. |
| 2007/0026389 | A1 | 2/2007 | Kaddurah-Daouk et al. |
| 2007/0072203 | A1 | 3/2007 | Kaddurah-Daouk et al. |
| 2007/0172820 | A1 | 7/2007 | Kaddurah-Daouk et al. |
| 2007/0178599 | A1 | 8/2007 | Kaddurah-Daouk et al. |
| 2009/0325150 | A1 | 12/2009 | Martignetti et al. |

FOREIGN PATENT DOCUMENTS

| | | |
|---|---|---|
| CA | 2185574 | 3/1995 |
| CA | 2252715 | 4/1997 |
| CA | 2264535 | 8/1997 |
| CA | 2339817 | 8/1999 |
| CA | 2322019 | 9/1999 |
| CA | 2303758 | 4/2000 |
| CA | 2303761 | 4/2000 |
| CA | 2370749 | 4/2000 |
| CA | 2360816 | 10/2000 |
| WO | 9823950 A1 | 6/1998 |
| WO | 0077712 | 12/2000 |
| WO | 01/057518 A2 | 8/2001 |
| WO | 0157519 | 8/2001 |
| WO | 0178652 A2 | 10/2001 |

(Continued)

OTHER PUBLICATIONS

Diamandis EP. Mass spectrometry as a diagnostic and a cancer biomarker discovery tool. Molecular & Cellular Proteomics, vol. 3.4, pp. 367-378. (Year: 2004).* Trethewey et al., Current Opinions in Plant Biology 2:83-85 (1999).
Shinka et al., J. ChromatographyB 732:469-477 (1999).
Darius et al., J. ChromatographyB 682:67-72 (1996).
Huang et al., J. Am. Soc. Mass Spectrom. 10:1166-1173 (1999).
White et al., Analytical Chemistry 55:339-343 (1983).
Ledford et al., Analytical Chemistry 52:463-468 (1980).
Skrzydlewska et al., J. of Toxicology and Environmental Health (64): 213-222 (2001).

(Continued)

*Primary Examiner* — Russell S Negin
(74) *Attorney, Agent, or Firm* — Pepper Hamilton LLP

(57) ABSTRACT

The present invention relates to the diagnosis of colorectal and ovarian cancers (CRC and OC, respectively). The present invention describes the relationship between endogenous small molecules and CRC or OC. Specifically, the present invention relates to the diagnosis of CRC and OC through the measurement of vitamin E isoforms and related metabolites. The present invention also relates to diagnostic markers identified in said method. The present invention relates to the underlying case and pre-symptomatic phases of CRC, the diagnosis of various stages and severity of CRC, the early detection of CRC, monitoring and diagnosing the effect of therapy on CRC and OC health states.

12 Claims, 44 Drawing Sheets

(56) References Cited

FOREIGN PATENT DOCUMENTS

| WO | 0192872 | 12/2001 |
|---|---|---|
| WO | 0196861 | 12/2001 |
| WO | 0204957 | 1/2002 |
| WO | 03005628 | 1/2003 |
| WO | 03/014724 A1 | 2/2003 |
| WO | 2004090550 A2 | 10/2004 |
| WO | 2004102190 A1 | 11/2004 |

OTHER PUBLICATIONS

Stahelin et al. JNCI 73(6): 1463-1468 (1984).
Jensen et al., Analytical Chemistry 71:2076-2084 (1999).
Conrads et al., "Cancer Diagnosis using Proteomic Patterns," Expert Rev. Mol. Diagn. 3(4):411-420 (2003).
Conrads et al., "Proteomic Patterns as a Diagnostic Tool for Early-Stage Cancer: A Review of its Progress to a Clinically Relevant Tool," Mol. Diagn. 8(2):77-85 (2004).
Zhao et al., "Identification of Colorectal Cancer Using Proteomic Patterns in Serum," Ai Zheng 23(6):614-618 (2004) (abstract in English).
International Preliminary Examination Report for corresponding PCT Application PCT/CA2006/001502.
PubChem Public Chemical Database, "diisodecyl phthalate—Compound Summary," XP002575737 retrieved from NCBI Accession No. 33599 (Mar. 27, 2005).
Supplementary Partial European Search Report for European Patent Application No. EP06817639 (dated Mar. 30, 2010).
Skryzydlewska et al., "Lipid Peroxidation and Antioxidant Status in Colorectal Cancer," World J. Gastrol. 11(3):403-406 (2005).
Yu et al., "Ovarian Cancer Identification Based on Dimensionality Reduction for High-Throughput Mass Spectrometry Data," Bioinformatics 21(10):2200-2209 (2005).
Griffin et al., "Metabolic Profiles of Cancer Cells," Nat. Rev. 4:551-561 (2004).

\* cited by examiner

A. 416.3666, C28H48O2, gamma-tocopherol (1)

B. 410.3184, C28H42O2, gamma-tocotrienol (2)

C. 448.3406, C28H48O4 (3)

D. 464.3522, C28H48O5 (4)

E. 446.3406, C28H46O4 (5)

F. 466.3661, C28H50O5 (6)

G. 450.3726, C28H50O4 (7)

H. 468.3840, C28H52O5 (8)

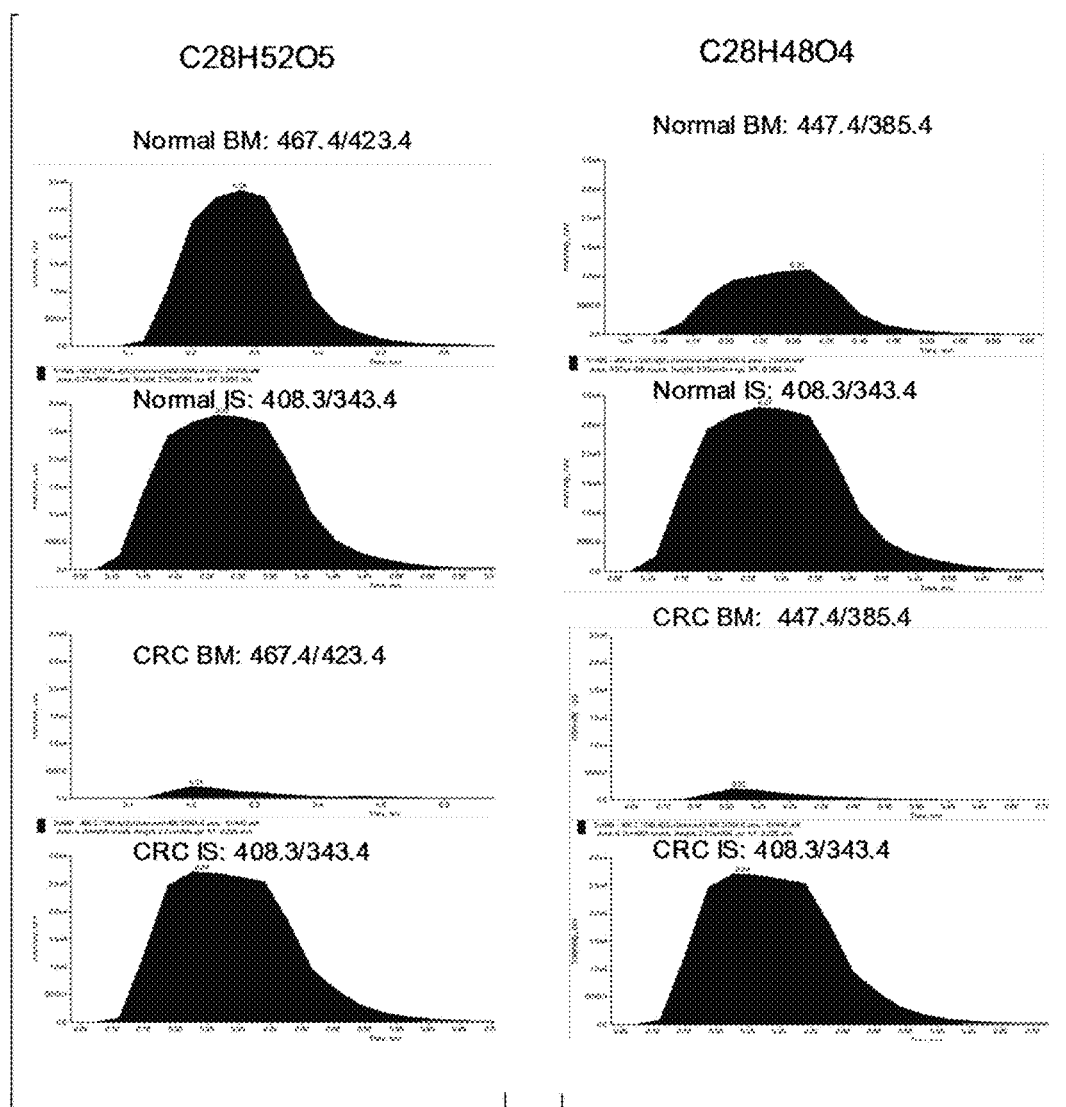
*FIG. 27C*     *FIG. 27D*

METHODS FOR DIAGNOSING A COLORECTAL CANCER (CRC) HEALTH STATE OR CHANGE IN CRC HEALTH STATE, OR FOR DIAGNOSING RISK OF DEVELOPING CRC OR THE PRESENCE OF CRC IN A SUBJECT

This application is continuation of U.S. patent application Ser. No. 11/910,942, which is a national stage application under 35 U.S.C. § 371 of PCT Application CA2006/001502, filed Sep. 12, 2006, which claims benefit under 35 U.S.C. § 119 of U.S. Provisional Patent Application No. 60/804,764, filed Jun. 14, 2006, and 60/716,310, filed Sep. 12, 2005.

FIELD OF INVENTION

The present invention relates to the diagnosis, of colorectal and ovarian cancer (CRC and OC, respectively). The present invention describes the relationship between endogenous small molecules and CRC or OC. Specifically, the present invention relates to the diagnosis of CRC and OC through the measurement of vitamin E-related metabolites. The present invention also relates to diagnostic markers identified in said method.

BACKGROUND OF THE INVENTION

Colorectal Cancer is the third most common malignancy in the world, and represents approximately ten percent of the world's total cancer incidence [1]. Due to the aging worldwide population, CRC represents a serious public health problem requiring new actions that will minimize the impact of this disease. The chance of surviving CRC is closely related to the stage of the disease at diagnosis (as shown in Table 1; the earlier the diagnosis, the greater the likelihood of survival. For example, there is less than a 5% chance of 5-year survival when diagnosed late in the disease timeframe (Dukes' stage D), while there is greater than 90% chance of 5-year survival when diagnosed early (Dukes' stage A). Therefore, CRC patients would greatly benefit from early detection because of the effectiveness of surgical treatment early on.

Currently, the risk factors for CRC are not well understood. In fact, few specific risk factors other than diet have been established for the disease. Inflammatory bowel disease and familial adenomatous polyposis (FAP) increase risk, but still only account for a very small proportion of overall CRC incidence. Ethnic and racial differences, as well as migrant studies, suggests that environmental factors play a role in disease etiology, as incidence rates among migrants and their descendants climb rapidly, reaching those of the host country [2, 3]. Overall, fewer than 15% of CRC cases are familial, suggesting a large impact of diet, environment, and lifestyle on the etiology of the disease.

The most common current screening tests for CRC are: 1) the fecal occult blood test (FOBT), which is based on the assumption that cancers will bleed, and can therefore be detected in the stool using chemical or immunological assays; and 2) invasive methods that identify gross abnormalities. The FOBT is the most widespread test used for CRC, and involves a crude test for the peroxidase-like activity of heme in hemoglobin. However, the sensitivity of the test is only approximately 50%, with a 20% sensitivity for adenomas, due to the fact that not all adenomas and CRCs bleed [2].

Methods for identifying gross abnormalities can include flexible sigmoidoscopy and colonoscopy, as well as double-contrast barium enema and virtual colonoscopy. Colonoscopy is the next test for patients with a positive FOBT, and, with an 80% false positive rate, imposes unnecessary hazards and risks to a large number of individuals. Colonoscopy is usually the preferred method for screening average and increased-risk individuals over the age of 50 who have a history of CRC or prior adenomatous polyps, or other predisposing diseases such as inflammatory bowel disease. There is no evidence that screening using colonoscopy alone in average-risk populations reduces incidence or mortality [3], however, sigmoidoscopy and integrated evaluations comprising combinations of the above techniques can reduce the expected CRC rates in higher-risk individuals over a given length of time [4].

Although colonoscopy is still the standard test for the presence or absence of polyps and CRC, it can miss 15% of lesions >1 cm in diameter [5]. Complications with colonoscopy can include perforation, hemorrhage, respiratory depression, arrhythmias, and infection [6]. Approximately one in 1,000 patients suffer perforations and three in 1,000 experience hemorrhaging. Between one and three deaths out of 10,000 tests occur as a result of the procedure [3]. Other disadvantages such as the lack of trained personnel, patient discomfort, and high cost will likely prevent the colonoscopy from becoming a routine CRC screening method for the general population (see Table 2). Most sporadic CRCs are thought to develop from benign adenomas, of which only a small number will ever develop to malignancy. Given that the time period for malignant development from benign adenoma is five to ten years, the detection of adenomas across the general population by colonoscopy/sigmoidoscopy would require a gross overtreatment of patients, being both costly and potentially harmful [7].

Computerized Tomography Colonography (CTC), or virtual colonoscopy, is a recent non-invasive technique for imaging the colon, with reports varying dramatically on the performance characteristics of the assay (ranging between 39% and 94% specificity), due primarily to technological differences in the patient preparation and the hardware and software used for the analysis. Other limitations of CTC include high false-positive readings, inability to detect flat adenomas, no capacity to remove polyps, repetitive and cumulative radiation doses, and cost [6].

With advances in our understanding of the molecular pathology of CRC, several new screening methods based on DNA analysis from stool samples have emerged. These are typically PCR-based assays used to identify mutations known to occur in the adenoma-to-carcinoma sequence, or in familial CRC. Commonly screened gene mutations include KRAS, TP53, APC, as well as assays for microsatellite instability and hypermethylated DNA. Table 2, reproduced from Davies et al [7], compares current screening methods for CRC.

All of the methods described above are typically only capable of detecting CRC after the formation of an adenoma, and are generally not ideally suited for large-scale population screening. None of the above tests provide a quantitative assessment of a CRC-positive or negative promoting environment. Neither do any of the above tests provide a quantitative assessment of the effect of CRC on normal human biochemistry and related health states. Whether genomics-based tests will result in high diagnostic accuracy for sporadic CRC remains to be seen. Davies et at [7] outlined the features of an ideal screening test for CRC, as follows: 1) inexpensive; 2) simple to perform; 3) non-invasive; 4) represents the whole colon; 5) unambiguous interpretation of results (that is, high sensitivity, specificity, positive predictive value, and negative predictive value); 6) easy to teach; and 7) easy to maintain quality control.

A diagnostic assay based on small molecules or metabolites in serum fulfills the above criteria, as development of assays capable of detecting specific metabolites is relatively simple and cost effective per assay. The test would be minimally invasive and would be indicative of disease status regardless of colonic proximity. Translation of the method into a clinical assay compatible with current clinical chemistry laboratory hardware would be commercially acceptable and effective, and would result in rapid deployment worldwide. Furthermore, the requirement for highly trained personnel to perform and interpret the test would be eliminated.

CRC-specific biomarkers in human serum that could provide an assessment of CRC presence, of a CRC-promoting or inhibitory environment, of the physiological burden of CRC, or a combination of these characteristics would be extremely beneficial in the management of CRC risk, prevention, and treatment. A test designed to measure these biomarkers would be widely accepted by the general population as it would be minimally invasive and could possibly be used to monitor an individual's susceptibility to disease prior to resorting to, or in combination with, conventional screening methods.

Ovarian Cancer is the fifth leading cause of cancer death among women [8]. It has been estimated that over 22,000 new cases of ovarian cancer will be diagnosed this year, with 16,210 deaths predicted in the United States alone [9]. Ovarian cancer is typically not identified until the patient has reached stage III or IV and have a poor prognosis (5 year survival of around 25-30%) [10]. The current screening procedures for ovarian cancer involve the combination of bimanual pelvic examination, transvaginal ultrasonography and serum CA125 measurements [9]. The efficacy of this screening procedure for ovarian cancer is currently of unknown benefit, as there is a lack of evidence that the screen reduces mortality rates, and it is under scrutiny for the risks associated with false positive results [8, 11]. According to the American Cancer Society CA125 measurement and transvaginal ultrasonography are not reliable screening or diagnostic tests for ovarian cancer, and that the only current method available to make a definite diagnosis is surgically.

CA125, cancer antigen-125, is a high molecular weight mucin that has been found to be elevated in most ovarian cancer cells as compared to normal cells [9]. A CA125 test result that is higher than 30-35 U/ml is typically accepted as being at an elevated level [9]. There have been difficulties in establishing the accuracy, sensitivity and specificity of the CA125 screen for ovarian cancer due to the different thresholds to define elevated CA125, varying sizes of patient groups tested, and broad ranges in the age and ethnicity of patients [8]. According to the Johns Hopkins University pathology website the CA125 test only returns a true positive result for ovarian cancer in roughly 50% of stage I patients and about 80% in stage II, III and IV. Endometriosis, benign ovarian cysts, pelvic inflammatory disease and even the first trimester of a pregnancy have been reported to increase the serum levels of CA125 [11]. The National Institute of Health's website states that CA-125 is not an effective general screening test for ovarian cancer. They report that only about 3 out of 100 healthy women with elevated CA125 levels are actually found to have ovarian cancer, and about 20% of ovarian cancer diagnosed patients actually have elevated CA125 levels.

The identification of highly specific and sensitive ovarian cancer biomarkers in human serum, therefore, would be extremely beneficial, as the test would be non-invasive and could possibly be used to monitor individual susceptibility to disease prior to, or in combination with, conventional methods. A serum test is minimally invasive and would be accepted across the general population.

SUMMARY OF THE INVENTION

In one embodiment of the present invention there is provided a method for identifying metabolite markers for use in diagnosing CRC and OC comprising the steps of: introducing a sample from a patient presenting said disease state, said sample containing a plurality of unidentified metabolites into a high resolution mass spectrometer, for example, a Fourier Transform Ion Cyclotron Resonance Mass Spectrometer (FTMS); obtaining, identifying and quantifying data for the metabolites; creating a database of said identifying and quantifying data; comparing the identifying and quantifying data from the sample with corresponding data from a control sample; identifying one or more metabolites that differ; and selecting the minimal number of metabolite markers needed for optimal diagnosis.

In a further embodiment of the present invention there is provided a process for developing a metabolite biomarker test to diagnose a health state of an organism comprising: obtaining biological samples from organisms from a plurality of health states; introducing said biological samples into a high resolution/accurate mass spectrometer to obtain identifying and quantifying data on the metabolites contained within the biological samples to discover metabolites that differ in intensity between a plurality of health states; identifying the minimal set of biomarkers necessary to differentiate said health states using multivariate statistics; confirming these biomarkers using an independent MS method; and creating a targeted high throughput method for the measurement of the biomarkers identified and verified.

In a further embodiment of the present invention there is provided a method for identifying colorectal cancer-specific metabolic markers comprising the steps of: introducing a sample from a patient diagnosed with colorectal/ovarian cancer, said sample containing a plurality of unidentified metabolites into a Fourier Transform Ion Cyclotron Resonance Mass Spectrometer (FTMS); obtaining identifying and quantifying data for the metabolites; creating a database of said identifying and quantifying data; comparing the identifying and quantifying data from the sample with corresponding data from a control sample; identifying one or more metabolites that differ; wherein the metabolites are selected from the group consisting of metabolites one or more of the metabolites shown in Table 3, or fragments or derivatives thereof.

In a further embodiment of the present invention there is provided a method for identifying colorectal cancer-specific metabolic markers comprising the steps of: introducing a sample from a patient diagnosed with colorectal/ovarian cancer, said sample containing a plurality of unidentified metabolites into a Fourier Transform Ion Cyclotron Resonance Mass Spectrometer (FTMS); obtaining identifying and quantifying data for the metabolites; creating a database of said identifying and quantifying data; comparing the identifying and quantifying data from the sample with corresponding data from a control sample; identifying one or more metabolites that differ; wherein the metabolites are selected from the group consisting of metabolites with neutral accurate masses measured in Daltons of, or substantially equivalent to, 446.3406, 448.3563, 450.3726, 464.3522, 466.3661, 468.3840, 538.4259, 592.4711, and 594.4851 and the LC-MS/MS fragment patterns shown in any one of FIGS. 13 to 21 or fragments or derivative thereof; and selecting the minimal number of metabolite markers needed for optimal diagnosis.

In a further embodiment of the present invention there is provided a method for identifying ovarian cancer-specific metabolic markers comprising the steps of: introducing a sample from a patient diagnosed for colorectal/ovarian cancer, said sample containing a plurality of unidentified metabolites into a Fourier Transform Ion Cyclotron Resonance Mass Spectrometer (FTMS); obtaining identifying and quantifying data for the metabolites; creating a database of said identifying and quantifying data; comparing the identifying and quantifying data from the sample with corresponding data from a control sample; identifying one or more metabolites that differ; wherein the metabolites are selected from the group consisting of metabolites with accurate neutral masses measured in Daltons of, or substantially equivalent to, 446.3406, 448.3563, 450.3726, 464.3522, 466.3661, 468.3840, 538.4259, 592.4711, and 594.4851 and the LC-MS/MS fragment patterns shown in any one of FIGS. 13 to 21 or fragments or derivative thereof; and selecting the minimal number of metabolite markers needed for optimal diagnosis.

In one embodiment of the present invention there is provided a CRC/OC cancer-specific metabolic marker selected from the metabolites listed in Table 3 or fragments or derivatives thereof.

In one embodiment of the present invention there is provided a CRC/OC cancer-specific metabolic marker selected from the group consisting of metabolites with an accurate neutral mass (measured in Daltons) of, or substantially equivalent to, 446.3406, 448.3563, 450.3726, 464.3522, 466.3661, 468.3840, 538.4259, 592.4711, and 594.4851 or fragments or derivative thereof where a +/−5 ppm difference would indicate the same metabolite.

In yet a further embodiment of the present invention there is provided a colorectal/ovarian cancer-specific metabolic marker selected from the group consisting of metabolites with an accurate neutral mass measured in Daltons of, or substantially equivalent to, 446.3406, 448.3563, 450.3726, 464.3522, 466.3661, 468.3840, 538.4259, 592.4711, and 594.4851 and the LC-MS/MS fragment patterns shown in any one of FIGS. 13 to 21 or fragments or derivatives thereof.

In yet a further embodiment of the present invention there is provided a colorectal/ovarian cancer-specific metabolic marker selected from the group consisting of metabolites with a molecular formula selected from the group consisting of: $C_{28}H_{46}O_4$, $C_{28}H_{48}O_4$, $C_{28}H_{50}O_4$, $C_{28}H_{48}O_5$, $C_{28}H_{50}O_5$, $C_{28}H_{52}O_5$, $C_{32}H_{58}O_6$, $C_{36}H_{64}O_6$ and $C_{36}H_{66}O_6$.

In a further aspect of the invention there is provided a method for diagnosing a patient for the presence of a colorectal or ovarian cancer or at risk of developing CRC or OC comprising the steps of: screening a sample from said patient for the presence or absence of one or more metabolic markers selected from the group consisting of metabolites listed in Table 3, or fragments or derivates thereof, wherein a difference in intensity of one or more of said metabolic markers indicates the presence of CRC or OC In a further embodiment of this aspect of the invention there is provided a method for diagnosing a patient for the presence of a colorectal or ovarian cancer comprising the steps of: screening a sample from said patient for the presence or absence of one or more metabolic markers selected from the group consisting of metabolites with an accurate neutral mass of, or substantially equivalent to, 446.3406, 448.3563, 450.3726, 464.3522, 466.3661, 468.3840, 538.4259, 592.4711, and 594.4851; wherein the absence of one or more of said metabolic markers indicates the presence of CRC or OC.

In a further embodiment of the present invention there is provided a method for diagnosing the presence or absence of CRC or OC in a test subject of unknown disease status, comprising: obtaining a blood sample from said test subject; analyzing said blood sample to obtain quantifying data on molecules selected from the group comprised of molecules identified by the neutral accurate masses 446.3406, 448.3563, 450.3726, 464.3522, 466.3661, 468.3840, 538.4259, 592.4711, and 594.4851 or molecules having masses substantially equal to these molecules or fragments of derivatives thereof; comparing the quantifying data obtained on said molecules in said test subject with quantifying data obtained from said molecules from a plurality of CRC or OC-positive humans or quantifying data obtained from a plurality of CRC or OC-negative humans; and using said comparison to determine the probability that the test subject is CRC/OC positive or negative.

The present invention also discloses the identification of vitamin E-like metabolites that are differentially expressed in the serum of CRC- and OC-positive patients versus healthy controls. The differential expressions disclosed are specific to CRC and OC.

In one embodiment of the present invention, a serum test, developed using an optimal subset of metabolites selected from the group consisting of vitamin E-like metabolites, can be used to diagnose CRC/OC presence, or the presence of a CRC or OC-promoting or inhibiting environment.

In another embodiment of the present invention, a serum test, developed using an optimal subset of metabolites selected from the group consisting of vitamin E-like metabolites, can be used to diagnose the CRC health-state resulting from the effect of treatment of a patient diagnosed with CRC. Treatment may include chemotherapy, surgery, radiation therapy, biological therapy, or other.

In another embodiment of the present invention, a serum test, developed using an optimal subset of metabolites selected from the group consisting of vitamin E-like metabolites, can be used to longitudinally monitor the CRC status of a patient on a CRC therapy to determine the appropriate dose or a specific therapy for the patient.

The present invention also discloses the identification of gamma-tocopherol/tocotrienol metabolites in which the aromatic ring structure has been reduced that are differentially expressed in the serum of CRC- and OC-positive patients versus healthy controls. The differential expressions disclosed are specific to CRC and OC.

The present invention discloses the presence of gamma-tocopherol/tocotrienol metabolites in which there exists —$OC_2H_5$, —$OC_4H_9$, or —$OC_8H_{17}$ moieties attached to the hydroxychroman-containing structure in human serum.

The present invention also discloses the identification of alpha-tocopherol metabolites that are differentially expressed in the serum of CRC-positive patients versus healthy controls. The differential expressions disclosed are specific to CRC.

In a further embodiment of the present invention there is provided a method for identifying and diagnosing individuals who would benefit from anti-oxidant therapy comprising: obtaining a blood sample from said test subject; analyzing said blood sample to obtain quantifying data on all, or a subset of, tocopherols, tocotrienols, vitamin E-related metabolites or metabolic derivatives of said metabolite classes; comparing the quantifying data obtained on said molecules in said test subject with reference data obtained from the analysis of a plurality of CRC- or OC-negative humans; and using said comparison to determine the probability that the test subject would benefit from such therapy.

In a further embodiment of the present invention there is provided a method for determining the probability that a subject is at risk of developing OC or CRC comprising: obtaining a blood sample from a CRC or OC asymptomatic subject; analyzing said blood sample to obtain quantifying data on all, or a subset of, tocopherols, tocotrienols, or metabolic derivatives of said metabolite classes; comparing the quantifying data obtained on said molecules in said test subject with reference data obtained from the analysis of a plurality of CRC- or OC-negative humans; using said comparison to determine the probability that the test subject is at risk of developing OC or CRC.

In a further embodiment of the present invention there is provided a method for diagnosing individuals who respond to a dietary, chemical, or biological therapeutic strategy designed to prevent, cure, or stabilize CRC or OC or improve symptoms associated with CRC or OC comprising: obtaining one or more blood samples from said test subject either from a single collection or from multiple collections over time; analyzing said blood samples to obtain quantifying data on all, or a subset of, tocopherols, tocotrienols, vitamin E-like molecules, or metabolic derivatives of said metabolite classes; comparing the quantifying data obtained on said molecules in said test subject's samples with reference data obtained from said molecules from a plurality of CRC- or OC-negative humans; and using said comparison to determine whether the metabolic state of said test subject has improved during said therapeutic strategy.

In a further embodiment of the present invention, there is provided a method for identifying individuals who are deficient in the cellular uptake or transport of vitamin E and related metabolites by the analysis of serum or tissue using various strategies, including, but not limited to: radiolabeled tracer studies, gene expression or protein expression analysis of vitamin E transport proteins, analysis of genomic aberrations or mutations in vitamin E transport proteins, in vivo or ex vivo imaging of vitamin E transport protein levels, antibody-based detection (enzyme-linked immunosorbant assay, ELISA) of vitamin E transport proteins.

This summary of the invention does not necessarily describe all features of the invention.

BRIEF DESCRIPTION OF THE DRAWINGS

These and other features of the invention will become more apparent from the following description in which reference is made to the appended drawings wherein:

FIGS. 7A to 7F). Top panel for each of FIGS. 7A-7F, 5 normal samples; bottom panel for each of FIGS. 7A-7F, 5 CRC-positive samples.

FIGS. 8A to 8F). Top panel for each of FIGS. 8A-8F, 5 normal samples; bottom panel for each of FIGS. 8A-8F, 5 CRC-positive samples.

FIGS. 27A-27G show Analyst screenshots of the 6 CRC biomarker transitions and internal standard transitions (FIG. 27A to 27F), and housekeeping transitions (FIG. 27G). Each page shows the peak areas for the transitions of two biomarkers in a typical "normal" and typical "CRC positive" individual. For each of FIGS. 27A to 27G, the top four plots are from the normal, the bottom four are from the CRC positive. BM: biomarker, IS: internal standard.

FIG. 31A shows the C30 series of tocopherol metabolites that arise from linolenic acid. FIG. 31B shows the C32 series of tocopherol metabolites that arise from linoleic acid. FIG. 31C shows the C36 series of tocopherol metabolites that arise from oleic acid.

FIG. 33A shows the short-chain alkane radical and long-chain aldehyde which results from breakdown at the bond indicated by the dotted line "A", and FIG. 33B shows the short-chain aldehyde and long-chain alkane radical that would result from spontaneous breakdown at bond "B" (dotted line B).

DETAILED DESCRIPTION OF THE INVENTION

Figure 1:
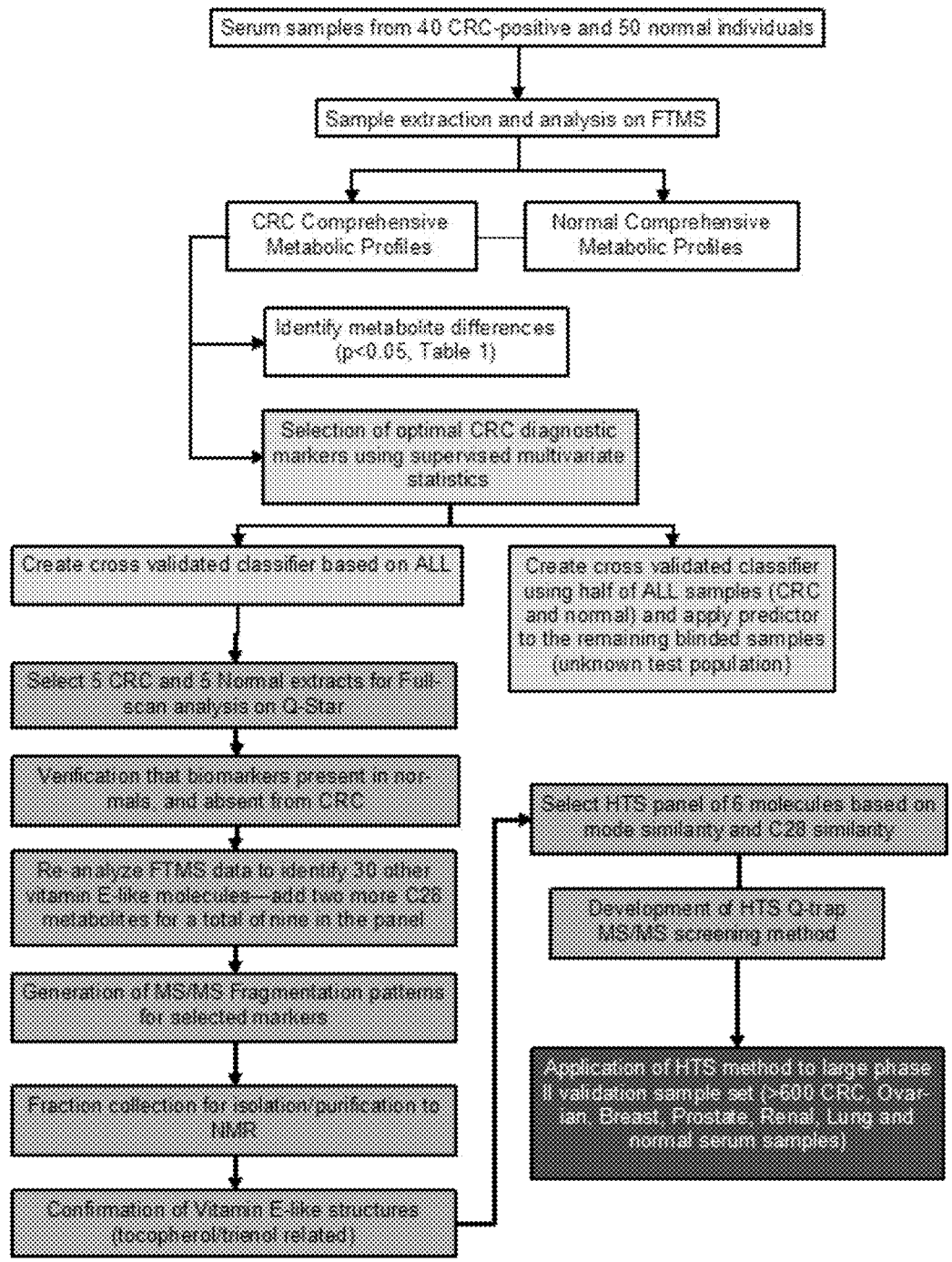
FIG. 1 shows a summary of the steps involved in the identification of the CRC/OC diagnostic biomarker panel in accordance with an embodiment of the present invention

The present invention relates to the diagnosis of colorectal and ovarian cancers (CRC and OC, respectively). The present invention describes the relationship between endogenous small molecules and CRC or OC. Specifically, the present invention relates to the diagnosis of CRC and OC through the measurement of vitamin E isoforms and related metabolites. More specifically, the present invention relates to the relationship between vitamin E-related metabolites in human serum and the implications thereof in CRC and OC.

The present invention discloses for the first time clear and unambiguous biochemical changes specifically associated with CRC. These findings also imply that the measurement of these biomarkers may provide a universal means of measuring the effectiveness of CRC therapies. This would dramatically decrease the cost of performing clinical trials as a simple biochemical test can be used to assess the viability of new therapeutics. Furthermore, one would not have to wait until the tumor progresses or until the patient dies to determine whether the therapy provided any benefit. The use of such a test would enable researchers to determine in months, rather than years, the effectiveness of dose, formulation, and chemical structure modifications of CRC therapies.

The present invention relates to a method of diagnosing CRC or OC by measuring the levels of specific small molecules present in human serum and comparing them to "normal" reference levels. In one embodiment of the present application there is described a novel method for the early detection and diagnosis of CRC or OC and the monitoring the effects of treatment on CRC and OC.

The preferred method involves the use of a high-throughput screening (HTS) assay developed from a subset of metabolites selected from Table 3 for the diagnosis of one or more diseases or particular health-states. The utility of the claimed method is demonstrated and validated through the development of a HTS assay capable of diagnosing a CRC-positive health-state.

The impact of such an assay on CRC and OC would be tremendous, as literally everyone could be screened longitudinally throughout their lifetime to assess risk and detect these diseases early. Given that the performance characteristics of the test are representative for the general CRC population, this test alone may be superior to any other currently available CRC screening method, as it may have the potential to detect disease progression prior to that detectable by conventional methods. The early detection of disease is critical to positive treatment outcome.

In order to determine whether there are biochemical markers of a given health-state in a particular population, a group of patients representative of the health state (i.e. a particular disease) and a group of "normal" counterparts are required. Biological samples taken from the patients in a particular health-state category can then be compared to the same samples taken from the normal population to identify differences between the two groups, by extracting the samples and analyzing using various analytical platforms including, but not limited to, Fourier transform ion cyclotron resonance mass spectrometry (FTMS) and liquid chromatography mass spectrometry (LC-MS). The biological samples could originate from anywhere within the body, including, but not limited to, blood (serum/plasma), cerebrospinal fluid (CSF), urine, stool, breath, saliva, or biopsy of any solid tissue including tumor, adjacent normal, smooth and skeletal muscle, adipose tissue, liver, skin, hair, kidney, pancreas, lung, colon, stomach, or other.

For the invention of the CRC diagnostic assay described, serum samples were obtained from representative populations of healthy CRC- and OC-negative individuals, and of professionally diagnosed CRC-positive patients. Throughout this application, the term "serum" will be used, but it will be obvious to those skilled in the art that plasma, whole blood, or a sub-fraction of whole blood may be used in the method.

When a blood sample is drawn from a patient there are several ways in which the sample can be processed. The range of processing can be as little as none (i.e. frozen whole blood) or as complex as the isolation of a particular cell type. The most common and routine procedures involve the preparation of either serum or plasma from whole blood. All blood sample processing methods, including spotting of blood samples onto solid-phase supports, such as filter paper or other immobile materials, are also contemplated by the invention.

The processed blood sample described above is then further processed to make it compatible with the analytical analysis technique to be employed in the detection and measurement of the biochemicals contained within the processed blood sample (in our case, a serum sample). The types of processing can range from as little as no further processing to as complex as differential extraction and chemical derivatization. Extraction methods include, but are not limited to, sonication, soxhlet extraction, microwave assisted extraction (MAE), supercritical fluid extraction (SFE), accelerated solvent extraction (ASE), pressurized liquid extraction (PLE), pressurized hot water extraction (PHWE), and/or surfactant-assisted extraction in common solvents such as methanol, ethanol, mixtures of alcohols and water, or organic solvents such as ethyl acetate or hexane. The preferred method of extracting metabolites for FTMS non-targeted analysis is to perform a liquid/liquid extraction whereby non-polar metabolites dissolve in an organic solvent and polar metabolites dissolve in an aqueous solvent. In one embodiment of the present invention, the metabolites contained within the serum samples were separated into polar and non-polar extracts by sonication and vigorous mixing (vortex mixing).

Extracts of biological samples are amenable to analysis on essentially any mass spectrometry platform, either by direct injection or following chromatographic separation. Typical mass spectrometers are comprised of a source, which ionizes molecules within the sample, and a detector for detecting the ionized particles. Examples of common sources include electron impact, electrospray ionization (ESI), atmospheric pressure chemical ionization (APCI), matrix assisted laser desorption ionization (MALDI), surface enhanced laser desorption ionization (SELDI), and derivations thereof. Common ion detectors can include quadrupole-based systems, time-of-flight (TOF), magnetic sector, ion cyclotron, and derivations thereof.

In accordance with the present invention the small molecules are identified by a method known as non-targeted analysis. Non-targeted analysis involves the measurement of as many molecules in a sample as possible, without any prior knowledge or selection of the components prior to the analysis (see WO 01/57518, published Aug. 9, 2001). Therefore, the potential for non-targeted analysis to discover novel metabolite biomarkers is high versus targeted methods, which detect a predefined list of molecules. The present invention uses a non-targeted method to identify metabolite components that differ between CRC-positive and healthy individuals, followed by the development of a high-throughput targeted assay for a subset of the metabolites identified from the non-targeted analysis. However, it would be obvious to anyone skilled in the art that other metabolite profiling strategies could potentially be used to discover some or all of the differentially regulated metabolites disclosed in this application and that the metabolites described herein, however discovered or measured, represent unique chemical entities that are independent of the analytical technology that may be used to detect and measure them.

According to this analysis many hundreds of small molecules, metabolites, or metabolite fragments can be identified that have differential abundances between CRC-positive serum and normal serum. The present invention discloses 480 metabolite masses, as listed in Table 3, which were found to have statistically significant differential abundances between CRC-positive serum and normal serum. All of these features, which differ statistically between the two populations have potential diagnostic utility. However, the incorporation of 480 signals into a commercially diagnostic assay is impractical, so well known methods of selecting an optimum diagnostic set of markers or metabolites was conducted.

From the methods described in this patent, a panel of nine metabolites was chosen as optimal for discriminating CRCs form normals. In the present invention colorectal cancer-specific metabolic markers selected from the group consisting of metabolites with an accurate neutral mass (measured in Daltons) of, or substantially equivalent to, 446.3406, 448.3563, 450.3726, 464.3522, 466.3661, 468.3840, 538.4259, 592.4711, and 594.4851 where a +/−5 ppm difference would indicate the same metabolite, were identified. These markers can thus be used in a diagnostic test to screen patients for the presence of CRC.

Of the nine metabolites described above, six were selected further for implementation into a high-throughput screening (HTS) assay. The HTS assay is based upon conventional triple-quadrupole mass spectrometry technology (See FIG. 26 for summary). The HTS assay works by directly injecting a serum extract into the triple-quad mass spectrometer, which then individually isolates each of the six parent molecules by single-ion monitoring (SIM). This is followed by the fragmentation of each molecule using an inert gas (called a collision gas, collectively referred to collision-induced dissociation or CID). The intensity of a specific fragment from each parent biomarker is then measured and recorded, through a process called multiple-reaction monitoring (MRM). In addition, an internal standard molecule is also added to each sample and subject to fragmentation as well. This internal standard fragment should have the same intensity in each sample if the method and instrumentation is operating correctly. When all six biomarker fragment intensities, as well as the internal standard fragment intensities are collected, a ratio of the biomarker to IS fragment intensities are calculated, and the ratios log-transformed. The lowest value of the six for each patient sample is then compared to a previously determined distribution of disease-positive and controls, to determine the relative likelihood that the person is positive or negative for the disease.

There are multiple types of cost-effective assay platform options currently available depending on the molecules being detected. These can include colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays, image analysis such as MRI, petscan, CT scan, and various mass spectrometry-based systems.

According to this aspect of the invention, there is provided the development of a commercial method for screening patients for CRC using the MS/MS fragmentation patterns identified in the previous section. There are numerous options for the deployment of the assay world-wide. The two most obvious are: 1, the development of MS/MS methods compatible with current laboratory instrumentation and triple-quadrupole mass spectrometers which are readily in place in many labs around the world, and/or 2, the establishment of a testing facility where samples could be shipped and analyzed at one location, and the results sent back to the patient or patient's physician.

The structural elucidation of the selected metabolites was determined following a series of physical and chemical property investigations. For example the principal characteristics that are normally used for this identification are accurate mass and molecular formula determination, polarity, acid/base properties, NMR spectra, and MS/MS or MSn spectra. With the elucidation of the identity of the metabolites of the present invention it is possible to identify the metabolic pathway or pathways involved in the progression of the disease.

The molecular formulas of the nine preferred diagnostic markers (446.3406, 448.3563, 450.3726, 464.3522, 466.3661, 468.3840, 538.4259, 592.4711, and 594.4851), were determined to be $C_{28}H_{46}O_4$, $C_{28}H_{48}O_4$, $C_{28}H_{50}O_4$, $C_{28}H_{48}O_5$, $C_{28}H_{50}O_5$, $C_{28}H_{52}O_5$, $C_{32}H_{58}O_6$, $C_{36}H_{64}O_6$, $C_{36}H_{66}O_6$ based on their accurate neutral mass, polarity, and ionization characteristics. These metabolites have been determined, according to the present invention to consist of a semi-saturated chroman ring and phytyl side chain and therefore consistent with a vitamin E-related structure.

A significant amount of research has been performed on the effects of vitamin E in vitro and on animals models of CRC whereas very little research has been done regarding vitamin E and OC. As early as 1980, Cook and McNamara [12] showed a protective effect of vitamin E on chemically induced colon cancer in mice. However, human studies have failed to provide any compelling evidence that vitamin E plays a significant role in any of the prevention, cause, treatment, or supportive treatment of CRC. Coulter et al showed that out of 38 studies there was no significant effect of alpha-tocopherol treatment for any individual cancer, and that a pooled relative risk alone was 0.91 (95% CI: 0.74 m 1.12)[13].

The term "vitamin E" collectively refers to eight naturally occurring isoforms, four tocopherols (alpha, beta, gamma, and delta) and four tocotrienols (alpha, beta, gamma, and delta). The predominant form found in western diets is gamma-tocopherol whereas the predominant form found in human serum/plasma is alpha-tocopherol. Tocotrienols are also present in the diet, but are more concentrated in cereal grains and certain vegetable oils such as palm and rice bran oil. Interestingly, it is suggested that tocotrienols may be more potent than tocopherols in preventing cardiovascular disease and cancer [14]. This may be attributable to the increased distribution of tocotrienols within lipid membranes, a greater ability to interact with radicals, and the ability to be quickly recycled more quickly than tocopherol counterparts [15]. It has been demonstrated that in rat liver microsomes, the efficacy of alpha-tocotrienol to protect against iron-mediated lipid peroxidation was 40 times higher that that of alpha-tocopherol [15]. However, measurements in human plasma indicate that trienols are either not detected or present only in minute concentrations [16], due possibly to the higher lipophilicity resulting in preferential bilary excretion [17].

A considerable amount of research related to the discrepancy between the distribution of alpha and gamma tocopherol has been performed on these isoforms. It has been known and reported as early as 1974 that gamma- and alpha-tocopherol have similar intestinal absorption but significantly different plasma concentrations [18]. In the Bieri and Evarts study [18], rats were depleted of vitamin E for 10 days and then fed a diet containing an alpha:gamma ratio of 0.5 for 14 days. At day 14, the plasma alpha:gamma ratio was observed to be 5.5! The authors attributed this to a significantly higher turnover of gamma-tocopherol, however, the cause of this increased turnover was unknown. Plasma concentrations of the tocopherols are believed to be tightly regulated by the hepatic tocopherol binding protein. This protein has been shown to preferentially bind to alpha-tocopherol [19]. Large increases in alpha-tocopherol consumption result in only small increases in plasma concentrations [20]. Similar observations hold true for tocotrienols, where high dose supplementation has been shown to result in maximal plasma concentrations of approximately only 1 to 3 micromolar [21]. More recently, Birringer et al [17] showed that although upwards of 50% of ingested gamma-tocopherol is metabolized by human hepatoma HepG2 cells by omega-oxidation to various alcohols and carboxylic acids, less than 3% of alpha-tocopherol is metabolized by this pathway. This system appears to be responsible for the increased turnover of gamma-tocopherol. In this paper, they showed that the creation of the omega COOH from gamma-tocopherol occurred at a rate of >50× than the creation of the analogous omega COOH from alpha-tocopherol. Birringer also showed that the trienols are metabolized via a similar, but more complex omega carboxylation pathway requiring auxiliary enzymes [17].

It is likely that the existence of these two structurally selective processes has biological significance. Birringer et al [17] propose that the purpose of the gamma-tocopherol-specific P450 omega hydroxylase is the preferential elimination of gamma-tocopherol/trienol as 2,7,8-trimethyl-2-(beta-carboxy-3'-carboxyethyl)-6-hydroxychroman (gamma-CEHC). We argue, however, that if the biological purpose is simply to eliminate gamma-tocopherol/trienol, it would be far simpler and more energy efficient via selective hydroxylation and glucuronidation. The net biological effect of these two processes, which has not been commented on in the vitamin E literature, is that the two primary dietary vitamin E isoforms (alpha and gamma), upon entering the liver during first-pass metabolism, are shunted into two separate metabolic systems. System 1 quickly moves the most biologically active antioxidant isoform (alpha-tocopherol) into the blood stream to supply the tissues of the body with adequate levels of this essential vitamin. System 2 quickly converts gamma-tocopherol into the omega COOH. In the present invention it is disclosed that significant concentrations of six isoforms of gamma-tocopherol/tocotrienol omega COOH are present in normal human serum at all times. We were able to estimate that the concentration of each of these molecules in human serum is in the low micromolar range by measuring cholic acid, an organically soluble carboxylic acid-containing internal standard used in the triple-quadrupole method. This is within the previously reported plasma concentration range of 0.5 to 2 micromolar for γ-tocopherol (approximately 20 times lower than that of alpha-tocopherol) [22] The cumulative total, therefore, of all six novel γ-tocopheric acids in serum is not trivial, and likely exceeds that of γ-tocopherol itself. None of the other shorter chain length gamma-tocopherol/trienol metabolites described by Birringer et al [17] were detected in the serum. Also, the alpha and gamma tocotrienols were also not detected in the serum of patients used in the studies reported in this work, suggesting that the primary purpose of the gamma-tocopherol/trineol-specific P450 omega hydroxylase is the formation of the omega COOH and not gamma-CEHC. Not to be bound by the correctness of the theory, it is therefore suggested that the various gamma-tocopherol/tocotrienol omega COOH metabolites disclosed in the present application are novel bioactive agents and that they perform specific and necessary biological functions for the maintenance of normal health and for the prevention of disease.

Of relevance is also the fact that it has been shown that mammals are able to convert trienols to tocopherols in vivo [23, 24]. Since two of the novel six vitamin E-like metabolites contain a saturated phytyl side chain, and are therefore tocopherol-like, and the other four harbor a semi-saturated phytyl side chain, suggesting a tocotrienol origin. Since mammals cannot introduce the double-bonds, therefore, it is possible that all six molecules originate from a tocotrienol-like precursor.

Just as trienols have been reported to have biological activities separate from the tocopherols [25], gamma-tocopherol has been reported to have biological functions separate and distinct from alpha-tocopherol. For example, key differences between alpha tocopherol and alpha tocotrienol include the ability of alpha tocotrienol to specifically prevent neurodegeneration by regulating specific mediators of cell death [26], the ability of trienols to lower cholesterol [27], the ability to reduce oxidative protein damage and extend life span of *C. elegans* [28], and the ability to suppress the growth of breast cancer cells [29, 30]. Key differences between the gamma and alpha forms of tocopherol include the ability of gamma to decrease proinflammatory eicosanoids in inflammation damage in rats [31] and inhibition of cyclooxygenase (COX-2) activity [32]. In Jiang et al [32] it was reported that it took 8-24 hours for gamma-tocopherol to be effective and that arachadonic acid competitively inhibits the suppression activity of gamma-tocopherol. It is hypothesized that the omega COOH metabolites of gamma-tocopherol may be the primary bioactive species responsible for its anti-inflammation activity. The conversion of arachadonic acid into eicosanoids is a critical step in inflammation. It is more conceivable that omega COOH forms of gamma-tocopherol, due to their structural similarities to arachadonic acid, are more potent competitive inhibitors of this formation than native gamma-tocopherol.

In one aspect of this invention there is provided novel gamma-tocopherol/tocotrienol metabolites in human serum. These gamma-tocopherol/trienol metabolites have had the aromatic ring structure reduced. In this aspect of the invention, the gamma-tocopherol/tocotrienol metabolites comprise —$OC_2H_5$, —$OC_4H_9$, or —$OC_8H_{17}$ moieties attached to the hydroxychroman structure in human serum.

Not to be bound to any particular theory, the present invention discloses a hypothesis as to how gamma-tocopherol/tocotrienol can react with alkane radicals to create a stable alkene and a stabilized gamma-tocopherol/tocotrienol radical. It is suggested that, through this mechanism, one molecule of gamma-tocopherol/tocotrienol can neutralize up to six alkane radicals. The present invention further suggests how a gamma-tocopherol/tocotrienol radical can react with a lipid peroxide and subsequently neutralize the lipid peroxide into a stable gamma-tocopherol/tocotrienol alkyl ether and a stable lipid aldehyde. It is also suggested that the presence of iron may catalyze this reaction.

The uptake and concentration of gamma-tocopherol is dramatically different in colon epithelial cells relative to plasma. Tran and Chan [33] showed that gamma-tocopherol is preferentially taken up by human endothelial cells versus alpha-tocopherol, and Nair et al [34] showed that the in vivo concentration of gamma-tocopherol in human colon epithelial cells is 2-fold higher than alpha-tocopherol. Therefore, tissues that are primarily fed by the blood supply are preferentially enriched with alpha-tocopherol [18] whereas colon epithelial cells, which absorb tocopherols directly from the large intestine have concentrations representative of the dietary ratio of these isoforms [34].

The present application discloses that alpha-tocopherol/tocotrienol concentrations are significantly decreased in the serum of CRC patients versus controls but not in OC, prostate, renal cell, breast, or lung cancers. It is further disclosed that gamma-tocopherol and gamma-tocopherol/tocotrienol-related metabolite intensities are significantly decreased in the serum of CRC and OC patients versus controls but not in prostate, renal cell, breast, or lung cancers.

Not wishing to be bound by any particular theory, in the present invention it is hypothesized that the novel metabolites disclosed herein are indicators of vitamin E activity and that the decrease of such metabolites is indicative of one of the following situations:
1. A hyper-oxidative or metabolic state that is consuming vitamin E and related metabolites at a rate in excess of that being supplied by the diet;
2. A dietary deficiency or impaired absorption of vitamin E and related metabolites;
3. A dietary deficiency or impaired absorption/epithelial transport of vitamin E-related metabolites Specifically relating to the association of serum vitamin E concentrations and CRC, there have been no reports of significantly reduced vitamin E levels in CRC patients relative to controls. The most recent and robust study is that of Ingles et al [35]. In this study the authors stated: "We assayed plasma alpha and gamma-tocopherol concentrations for 332 subjects with colorectal adenomas and 363 control subjects from this previously signoidoscopy-based study. Increasing alpha and decreasing gamma-tocopherol levels were associated with decreased occurrence of large (>=1 cm) but not of small (<=1 cm) adenomas; however, after adjustment for potential confounding variables, these trends were not significant."

In all of the aforementioned related epidemiological studies concerning vitamin E and CRC, the focus of the research surrounded the implications of diet on disease incidence. None of these studies contemplate the effect of the disease on these endogenous metabolites. Therefore, one of the underlying hypothesis is that a dietary deficiency in a specific vitamin or nutrient leads to an increased risk of a particular disease. The hypothesis that the disease state leads to a deficiency in an essential nutrient or vitamin is not contemplated.

Based on the discoveries disclosed in this application, it is contemplated that although dietary deficiencies may increase the risk of CRC incidence (which has not been conclusively proven), the presence of CRC results in a decrease of vitamin E isoforms and related metabolites. These decreased levels are not likely to be the result of a simple dietary deficiency, as such a strong association would have been revealed in epidemiological studies. If CRC causes a decrease in these metabolites and not vice versa, then the weak epidemiological linkages between vitamin E concentrations and CRC may simply be the result of early, undetected CRC presence in the assumed normal cohort, as it is known that CRC can take many years to manifest to a size and degree that is detectable by colonoscopy.

Based on the discoveries disclosed in this application, it is also contemplated that the decreased levels of vitamin E-like metabolites are not the result of a simple dietary deficiency, but rather impairment in the colonic epithelial uptake of vitamin E and related molecules. This therefore represents a rate-limiting step for the sufficient provision of anti-oxidant capacity to epithelial cells under an oxidative stress load. In this model, the dietary effects of increased iron consumption through red meats, high saturated fat, and decreased fibre (resulting in a decreased iron chelation effect [36]) results in the previously mentioned Fenton-induced free radical propagation, of which sufficient scavenging is dependent upon adequate epithelial levels of vitamin E. Increases in epithelial free radical load, combined with a vitamin E-related transport deficiency, would therefore be reflected by a decrease in vitamin E-like metabolites as anti-oxidants, as well as decreases in the reduced carboxylated isoforms resulting from hepatic uptake and P450-mediated metabolism. It has recently been shown that the uptake of Vitamin E into CaCo-2 colonic epithelial cells is a saturable process, heavily dependent upon a protein-mediated event [37]. Because protein transporters are in essence enzymes, and follow typical Michaelis-Menton kinetics, the rate at which vitamin E can be taken up into colonic epithelial cells would reach a maximal velocity (Vmax), which may not be capable of providing a sufficient anti-oxidant protective effect for the development of CRC. At some point in time, therefore, increasing rates of oxidative stress above the rate at which vitamin E can be transported into colon epithelial cells will deplete the intracolonic/epithelial pool. Therefore, the hypothesis for the development of CRC is based not only on increases in iron and low fiber in the diet, but on a deficiency in epithelial uptake of vitamin E gamma and related metabolites. This is consistent with many of the epidemiological studies showing a lack of any significant correlation between CRC incidence and dietary vitamin E supplementation, as large doses of vitamin E under this model would not be reflected by increased intra-epithelia levels.

The accurate neutral masses of the nine metabolites (M-H ions converted to neutral mass) specific to CRC pathology were determined by FTICR-MS to be 446.3406, 448.3563, 450.3726, 464.3522, 466.3661, 468.3840, 538.4259, 592.4711, and 594.4851. Based on these accurate neutral mass values, the molecular formulas of the nine preferred diagnostic markers were determined to be $C_{28}H_{46}O_4$, $C_{28}H_{48}O_4$, $C_{28}H_{50}O_4$, $C_{28}H_{48}O_5$, $C_{28}H_{50}O_5$, $C_{28}H_{52}O_5$, $C_{32}H_{58}O_6$, $C_{36}H_{64}O_6$, $C_{36}H_{66}O_6$, respectively.

The M-H ions of these metabolites are characterized as having a collision induced dissociation (CID) MS/MS fragmentation pattern comprising one or more than one of the daughter ions shown in FIGS. 13 to 21. More particularly, the M-H ions of these seven metabolites are characterized as having a collision induced dissociation (CID) MS/MS fragmentation pattern comprising each of the daughter ions shown in FIGS. 13 to 21.

Based upon the accurate mass MS/MS spectra, putative structures were assigned to each of the biomarkers. The collective interpretation of the MS/MS spectra of the biomarkers revealed that they all contain a carboxylic acid moiety (as evidenced by a loss of $CO_2$) and at least one hydroxyl moiety (as evidenced by the loss of H2O). Furthermore all of the structures except the $C_{28}H_{46}O_4$ produced a $C_{18}H_xO_y$ fragment where $x \geq 31$ and $y \geq 2$, suggestive of a highly saturated fatty acid side chain. This information is consistent with the $C_{28}$ molecules being metabolites of gamma-tocopherol and gamma-tocotrienol. The $C_{32}$ and $C_{36}$ biomarkers were subsequently hypothesized to be metabolic byproducts resulting from the reaction of gamma-tocopherol and the lipid peroxides of linoleic and oleic acid residues, respectively.

Figure 12:
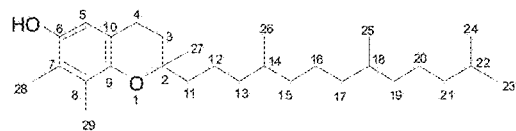
FIG. 12 shows the structures of gamma tocopherol and tocotrienol (Structures A and B, respectively) and six of the C28-containing vitamin-E-like molecules (Structures C to H, respectively) as determined by MSMS and NMR.
Figure 12:
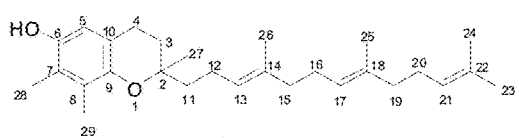
Figure 12:
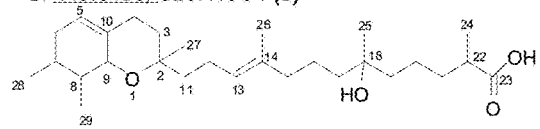
Figure 12:
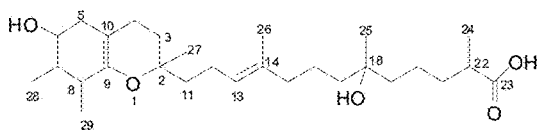
Figure 12:
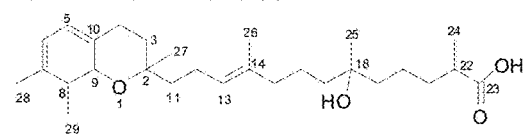
Figure 12:
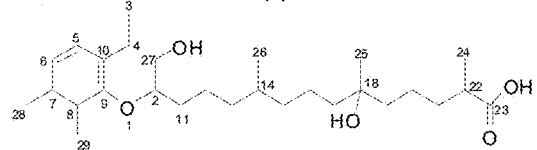
Figure 12:
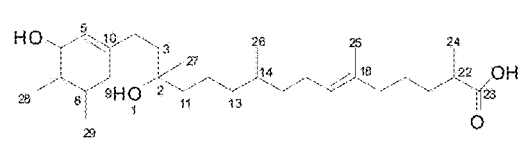
Figure 12:
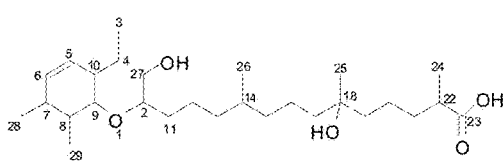

The confirmed structures for four of, and putative structures for two of, the selected six metabolites are shown in FIG. 12.

The present invention is also defined with reference to the following examples that are not to be construed as limiting.

EXAMPLES

Example 1

Discovery and Identification of Differentially Expressed Metabolites in CRC-Positive Versus Normal Healthy Controls The biochemical markers of CRC described in the invention were derived from the analysis of 40 serum samples from CRC-positive patients (24 TNM stage I/II and 16 stage III/IV) and 50 serum samples from healthy controls. All samples were single time-point collections, and the CRC samples were taken either immediately prior to or immediately following surgical resection of a tumor. All samples were taken prior to chemo- or radiation therapy.

Multiple non-targeted metabolomics strategies have been described in the scientific literature including NMR [38], GC-MS [39-41], LC-MS, and FTMS strategies [38, 42-44]. The metabolic profiling strategy employed for the discovery of differentially expressed metabolites in this application was the non-targeted FTMS strategy invented by Phenomenome Discoveries [40, 44-47].

The invention described herein involved the analysis of serum extracts from 90 individuals (40 CRC, 50 normal) by direct injection into an FTMS and ionization by either ESI or APCI, in both positive and negative modes. The advantage of FTMS over other MS-based platforms is the high resolving capability that allows for the separation of metabolites differing by only hundredths of a Dalton, many of which would be missed by lower resolution instruments. Organic (100% butanol) sample extracts were diluted either three or six-fold in methanol:0.1% (v/v) ammonium hydroxide (50:50, v/v) for negative ionization modes, or in methanol:0.1% (v/v) formic acid (50:50, v/v) for positive ionization modes. For APCI, ethyl acetate organic sample extracts were directly injected without diluting. All analyses were performed on a Bruker Daltonics APEX III FTMS equipped with a 7.0 T actively shielded superconducting magnet (Bruker Daltonics, Billerica, Mass.). Samples were directly injected using ESI and APCI at a flow rate of 600 μL per hour. Ion transfer/detection parameters were optimized using a standard mix of serine, tetra-alanine, reserpine, Hewlett-Packard tuning mix and the adrenocorticotrophic hormone fragment 4-10. In addition, the instrument conditions were tuned to optimize ion intensity and broad-band accumulation over the mass range of 100-1000 amu according to the instrument manufacturer's recommendations. A mixture of the abovementioned standards was used to internally calibrate each sample spectrum for mass accuracy over the acquisition range of 100-1000 amu.

In total six separate analyses comprising combinations of extracts and ionization modes were obtained for each sample:
Aqueous Extract
1. Positive ESI (analysis mode 1101)
2. Negative ESI (analysis mode 1102)
Organic Extract
3. Positive ESI (analysis mode 1201)
4. Negative ESI (analysis mode 1202)
5. Positive APCI (analysis mode 1203)
6. Negative APCI (analysis mode 1204)

Using a linear least-squares regression line, mass axis values were calibrated such that each internal standard mass peak had a mass error of <1 ppm compared with its theoretical mass. Using XMASS software from Bruker Daltonics Inc., data file sizes of 1 megaword were acquired and zero-filled to 2 megawords. A sin m data transformation was performed prior to Fourier transform and magnitude calculations. The mass spectra from each analysis were integrated, creating a peak list that contained the accurate mass and absolute intensity of each peak. Compounds in the range of 100-2000 m/z were analyzed. In order to compare and summarize data across different ionization modes and polarities, all detected mass peaks were converted to their corresponding neutral masses assuming hydrogen adduct formation. A self-generated two-dimensional (mass vs. sample intensity) array was then created using DISCO VAmetrics™ software (Phenomenome Discoveries Inc., Saskatoon, SK, Canada). The data from multiple files were integrated and this combined file was then processed to determine all of the unique masses. The average of each unique mass was determined, representing the y-axis. A column was created for each file that was originally selected to be analyzed, representing the x-axis. The intensity for each mass found in each of the files selected was then filled into its representative x,y coordinate. Coordinates that did not contain an intensity value were left blank. Once in the array, the data were further processed, visualized and interpreted, and putative chemical identities were assigned. Each of the spectra were then peak picked to obtain the mass and intensity of all metabolites detected. These data from all modes were then merged to create one data file per sample. The data from all 90 samples were then merged and aligned to create a two-dimensional metabolite array in which each sample is represented by a column and each unique metabolite is represented by a single row. In the cell corresponding to a given metabolite sample combination, the intensity of the metabolite in that sample is displayed. When the data is represented in this format, metabolites showing differences between groups of samples (i.e., normal and cancer) can be determined.

A student's T-test was used to select for metabolites that differ between the normal and the CRC-positive samples ($p<0.05$). The metabolites (480) that met this criterion are shown in Table 3. These are all features that differ in a statistically significant way between the two populations and therefore have potential diagnostic utility. The features are described by their accurate mass and analysis mode, which together are sufficient to provide the putative molecular formulas and chemical characteristics (such as polarity and putative functional groups) of each metabolite. However, the incorporation and development of 480 signals into a commercially useful assay is impractical, so supervised statistical methods were used to extract the optimum diagnostic feature set from the 480, as described below.

A supervised statistical method called prediction analysis of microarrays (PAM) was used to select metabolite features having optimal diagnostic properties from the initial array [48]. The method involves training a classifier algorithm using samples with a corresponding known diagnosis, which can then be applied to diagnose unknown samples (i.e. a test set). Several supervised methods exist, of which any could have been used to identify the best feature set, including artificial neural networks (ANNs), support vector machines (SVMs), partial least squares discriminant analysis (PLSDA), sub-linear association methods, Bayesian inference methods, supervised principal component analysis (PCA), shrunken centroids (described here), or others (see [49] for review).

Figure 2A:
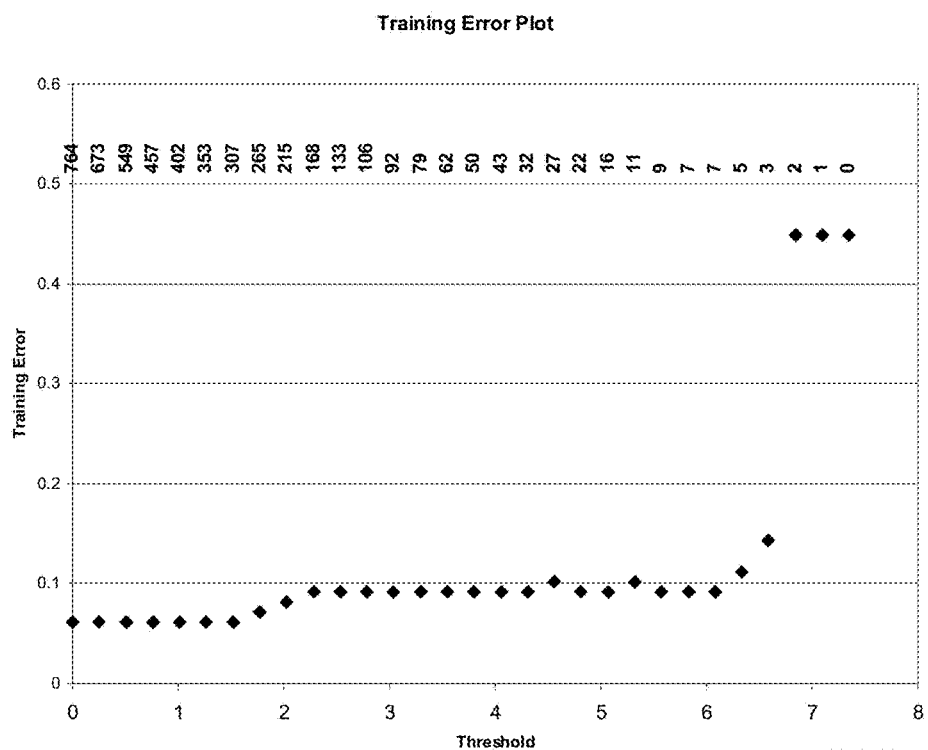
FIGS. 2A-2B are graphs that show the prediction of microarray analysis (PAM) training error (FIG. 2A) and cross validation misclassification error (FIG. 2B) plots.
Figure 2B:
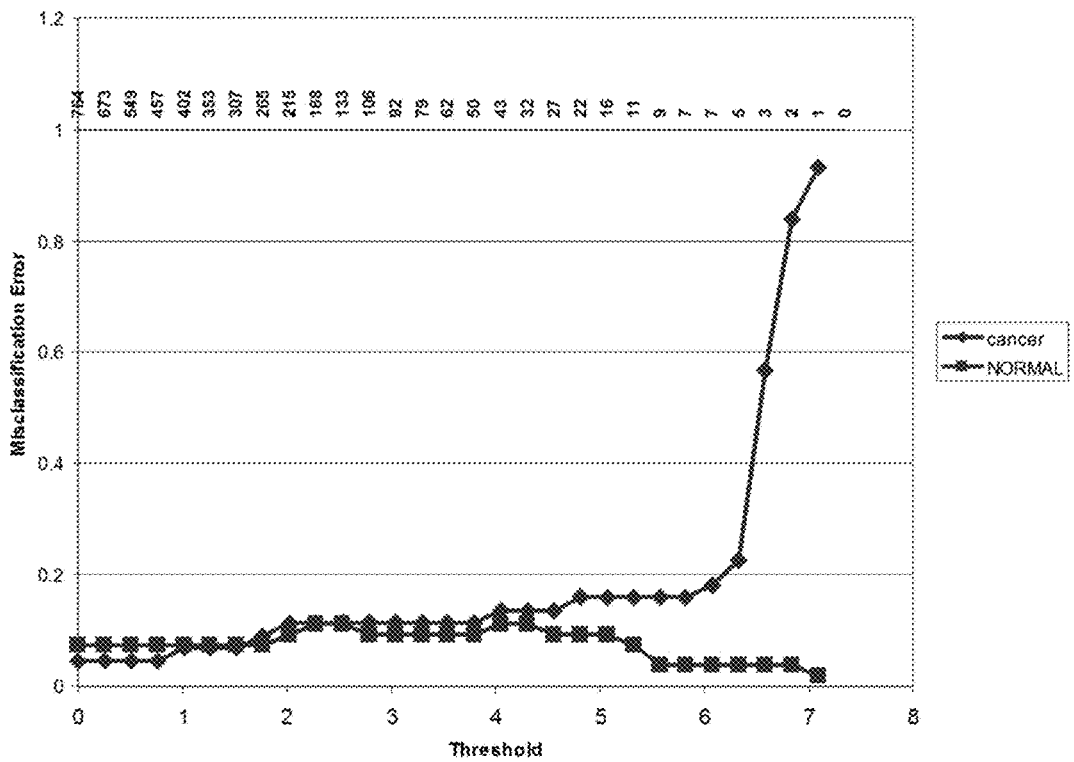

Since there were only 40 CRC samples to work with in the study, the validity of the PAM method for diagnosing CRC was tested in two ways. First, a cross-validated training classifier was created using all 90 samples (CRC and normal), leaving no samples for a test set. The second method involved randomly splitting the samples in half, using one half to generate a classifier and the other half as a blinded "test set" for diagnosis. Since the first method creates the classifier using more samples, its predictive accuracy would be expected to be higher than the second approach, and consequently should require fewer metabolites for high diagnostic accuracy. The key point is that the same diagnostic features identified in the first method are also inclusive to the subset identified in the second method. Based on these results, and signal-to-noise intensity information from the mass spectrometry data, seven metabolites were selected as the optimal CRC diagnostic biomarker set for further structural characterization. The graph in FIG. 2A shows the number of metabolites required to achieve given training errors at various threshold values (a user-definable PAM parameter). The plot shows that a training classifier with less than 10% error rate (0.1 training error) is possible with as few as 7 metabolite features (threshold value of approximately 5.8, see arrow). It is worthwhile to note that the lowest training error can be achieved using 300 or greater metabolite features, however, the error is only a few percent lower than using 7 metabolite features, and using hundreds of features would be impractical for clinical utility. The plot in FIG. 2B is conceptually similar to that in FIG. 2A, however, the graph in 2B shows the misclassification error of the trained classifier for CRC and normal individuals following the cross-validation procedure integral to the PAM program. The line connected by diamonds mirrors the previous result, showing that minimal cross-validated misclassification error for CRC-positive individuals can be achieved using as few as seven metabolites. It also shows that normal individuals, depicted by the squares, can be accurately diagnosed as normal using only one metabolite feature, but at this threshold, the misclassification error for CRC is greater than 95% (see arrows). Therefore, the best combination of metabolite features based on this method, which can both positively and negatively diagnose CRC comprises a combination of seven metabolite features. These included masses of, or substantially equivalent to 446.3406, 450.3726, 466.3661, 538.4259, 468.384, 592.4711, and 594.4851.

Figure 3:
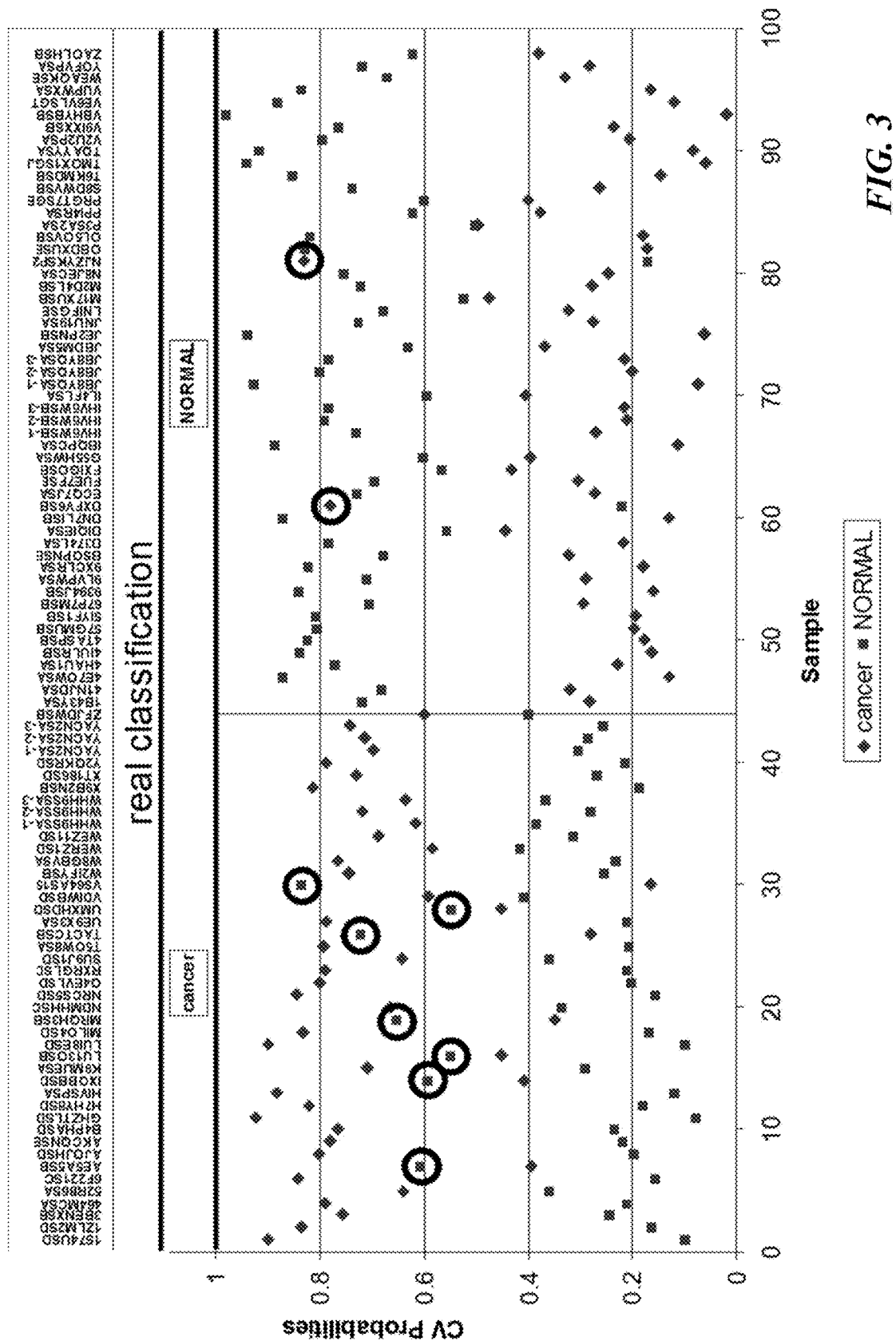
FIG. 3 shows the PAM output cross-validated diagnostic probabilities for all samples based on the classifier created in FIGS. 2A-2B.
Figure 4:
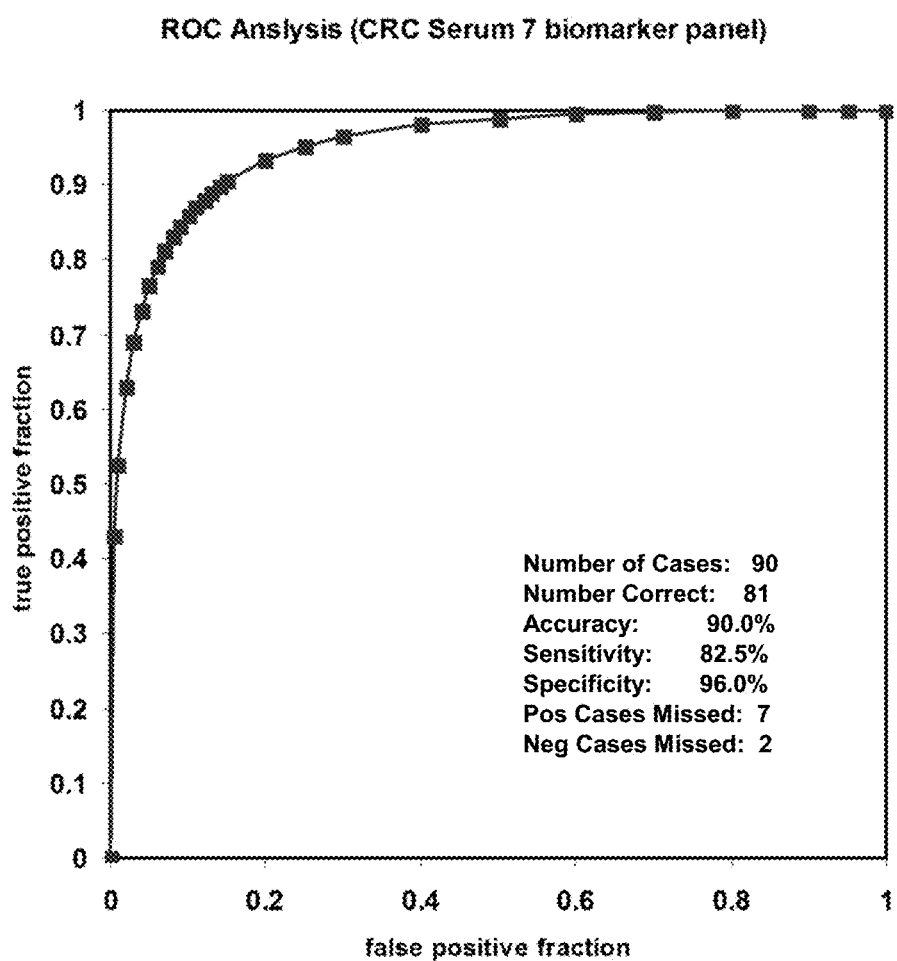
FIG. 4 shows the receiver-operator characteristic curve based on cross-validated probabilities.

The individual cross-validated diagnostic probabilities for each of the 90 individuals in the study are shown in FIG. 3. All of the CRC-positive samples are listed on the left side of the graph, and the normal individuals on the right. Each sample contains two points on the graph, one showing the probability of having CRC (diamonds), and one showing the probability of not having CRC (i.e. normal, squares). As can be seen, there are seven CRC samples, which classify as normal (circled on the left side of the graph) and two normal samples that classify as CRC-positive (circled on the right side of the graph). The predicted probabilities were then used to create the receiver-operating characteristic (ROC) curve in FIG. 4 using JROCFIT, which shows the true positive fraction (those with CRC being predicted to have CRC) versus the false positive fraction (normal individuals predicted as having CRC). The area under the curve is 95%, with a sensitivity of 82.5%, and a specificity of 96%. Overall, the diagnostic accuracy is 90% based on the cross-validated design. These seven metabolites were further selected for structural characterization.

Figure 5:
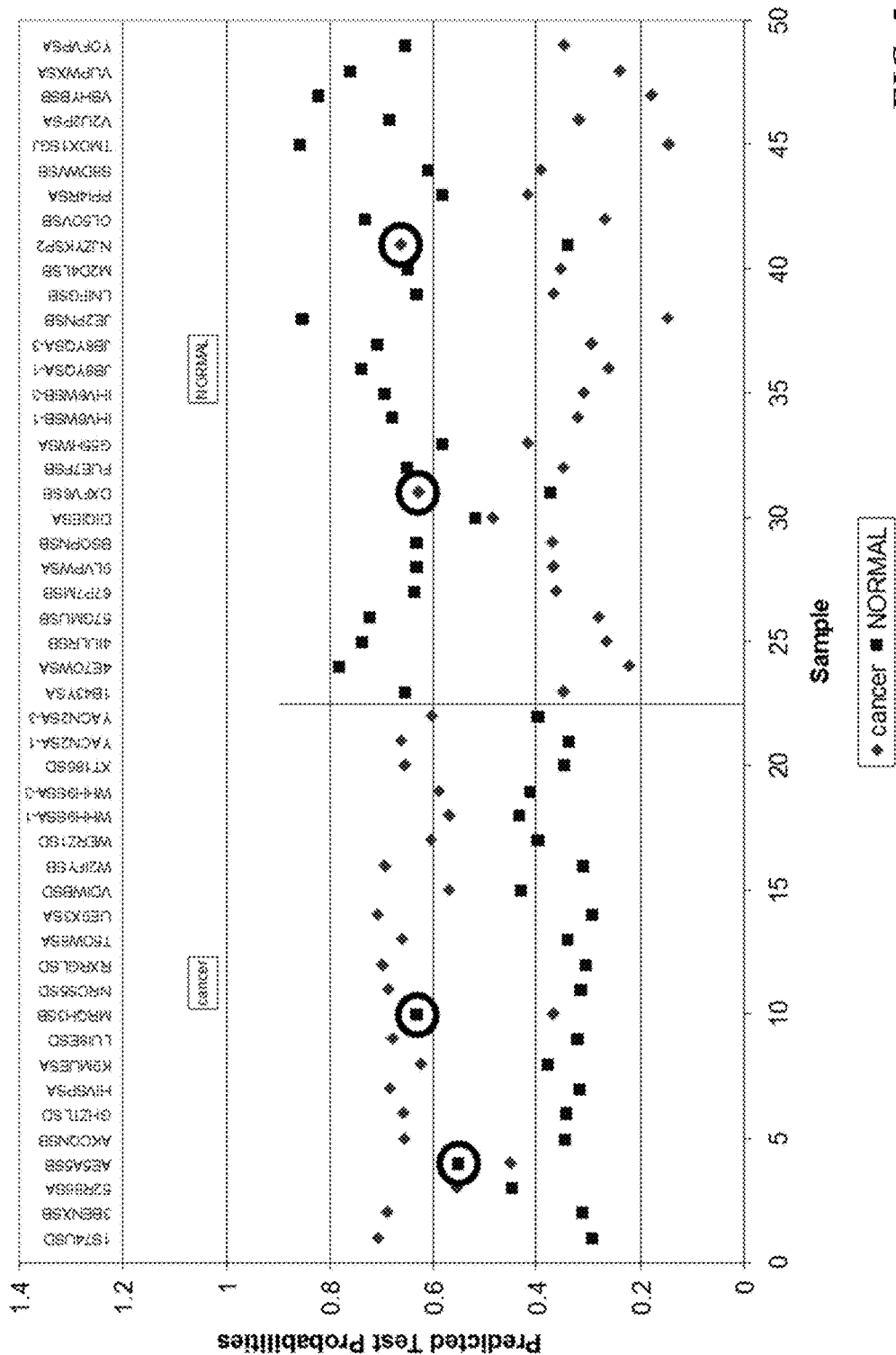
FIG. 5 shows the diagnostic predictions for blinded test samples when half the samples are used for training and the other half are used as a blinded test set.
Figures 6A, 6B:
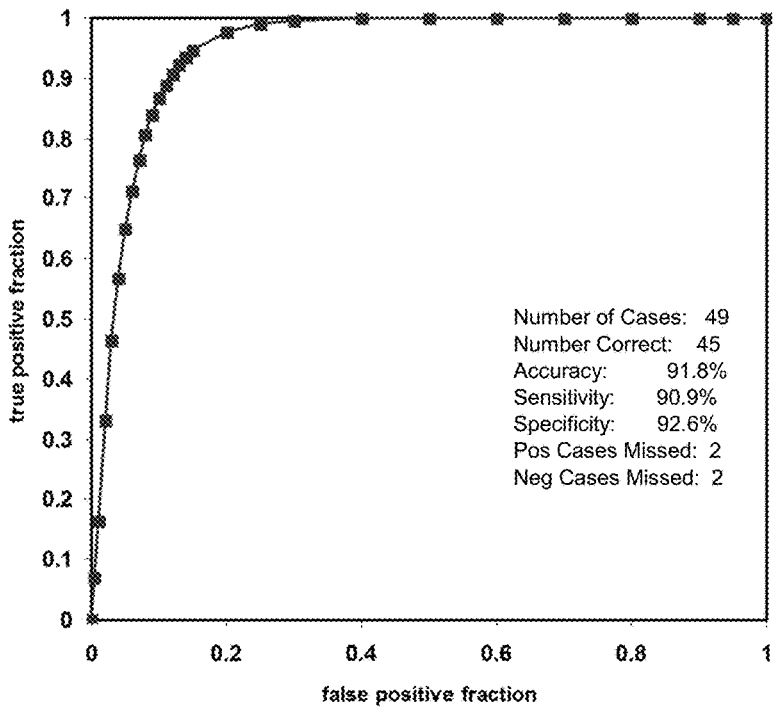
FIGS. 6A-6B show the prediction results (FIG. 6A) and receiver-operator characteristic curve (FIG. 6B) based on blinded test set diagnosis.
Figures 7A, 7B, 7C, 7D, 7E, 7F:
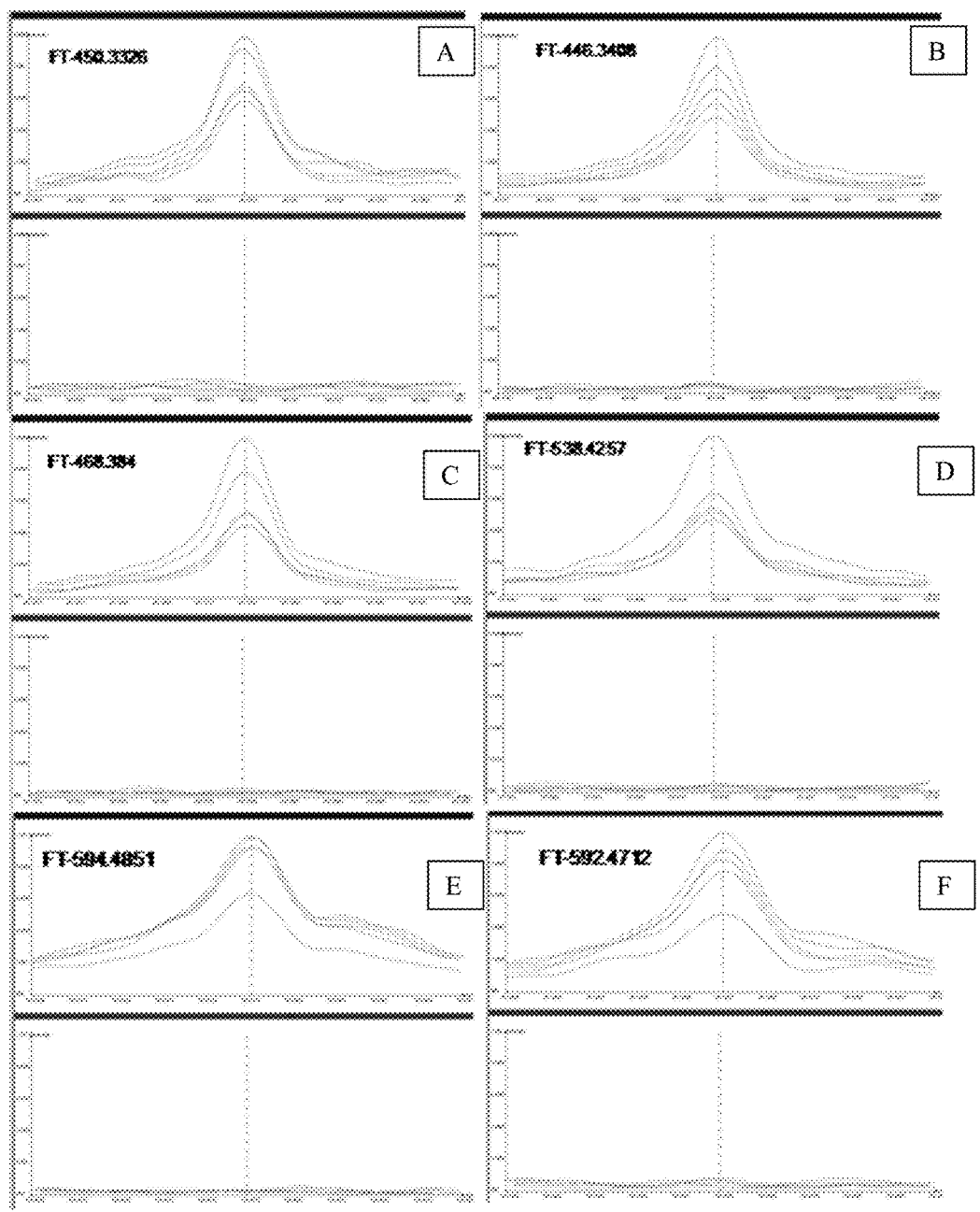
FIGS. 7A-7F show the raw FTMS spectra for six of the selected biomarkers (FTMS neutral mass shown.
Figures 8A, 8B, 8C, 8D, 8E, 8F:
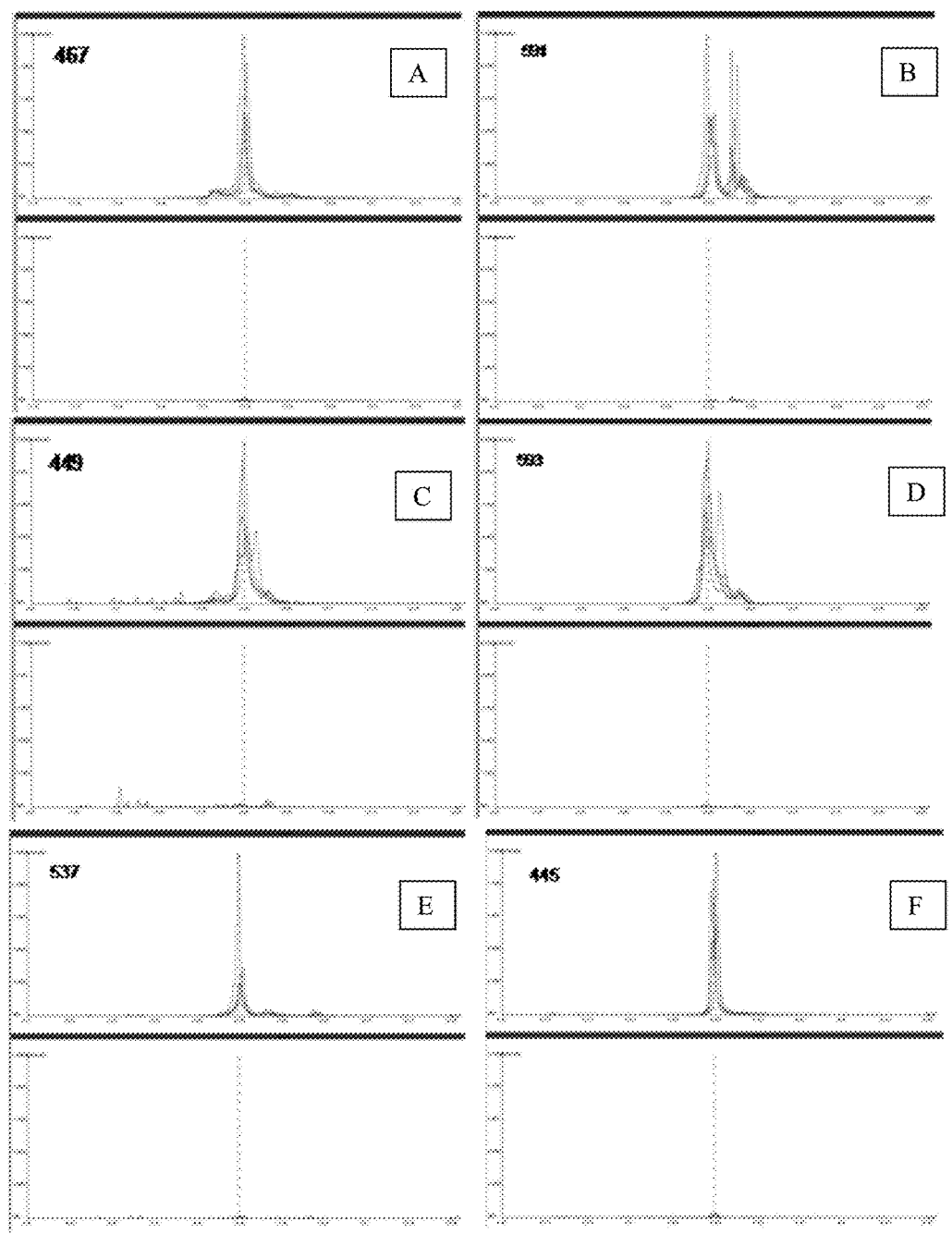
FIGS. 8A-8F show the QSTAR extracted ion chromatograms for six of the biomarkers (nominal detected mass indicated.

The more samples that are available as the training set, the more accurate the resulting classifier should be at diagnosing unknown samples. This was the reason for using all 90 samples to identify the optimal diagnostic marker panel described above. However, the drawback of this approach is that it leaves no samples available as blinded test set (which were not included in the training set). To address this problem, the samples were randomly split into two groups: one for creating the classifier and one to use as a test set. The training set comprised 21 CRC samples and 27 normals. The optimal number of metabolites required for the lowest misclassification error using these samples was 16, listed at the bottom of FIG. 5. Within these 16 are contained the subset of seven described above. The classifier was next used to predict the diagnosis of the remaining samples (blinded; 22 CRC and 27 normal). The predicted probabilities of the blinded test samples as either being CRC-positive or normal are plotted in FIG. 5. The results show that two of the CRC-positive samples are given a higher probability of being normal, and two of the normals are given a higher probability of being CRC-positive. FIG. 6A lists the patients, which were used in the test set, and their actual and predicted diagnosis. The probabilities from FIG. 5 were then translated into a ROC curve, as shown in FIG. 6B. The performance characteristics based on classification of the blinded test set were sensitivity of 91%, specificity of 92.6%, and overall diagnostic accuracy of 91.8%.

To verify that the seven metabolites selected by the classifier were indeed showing differences between CRC and normal serum, the raw spectral data were visualized. Spectra for six of the seven biomarkers for five of the normal and five of the CRC samples are shown in FIGS. 7A to 7F (normals on the top and CRCs on the bottom of each panel). In each case, the marker is present in the normal samples, and absent from the CRC samples.

Based upon these results, a clear distinction can be made between the serum of CRC-positive patients and healthy (non-CRC) individuals. Therefore, such findings, capable of identifying and distinguishing CRC-positive and CRC-negative serum, can form the basis for a CRC diagnostic test as described in this application.

Example 2

Independent Method Confirmation of Discovered Metabolites

The intensity differences between normal and CRC serums for the seven diagnostic metabolites discovered using the FTMS method were verified using an independent mass spectrometry method. Five representative CRC-positive sample extracts and five representative normal sample extracts were analyzed by LC-MS using an HP 1050 high-performance liquid chromatography interfaced to an ABI QSTAR® mass spectrometer.

Ethyl acetate fractions from five CRC and five normal sample extracts were evaporated under nitrogen gas and reconstituted in 70 uL of isopropanol:methanol:formic acid (10:90:0.1). 10 µL of the reconstituted sample was subjected to HPLC (HP 1050 with Hypersil ODS 5 u, 125×4 mm column, Agilent Technologies) for full scan, and 30 µL for MS/MS at a flow rate of 1 ml/min.

Eluate from the HPLC was analyzed using an ABI QSTAR® XL mass spectrometer fitted with an atmospheric pressure chemical ionization (APCI) source in negative mode. The scan type in full scan mode was time-of-flight (TOF) with an accumulation time of 1.0000 seconds, mass range between 50 and 1500 Da, and duration time of 55 min. Source parameters were as follows: Ion source gas 1 (GS1) 80; Ion source gas 2 (GS2) 10; Curtain gas (CUR) 30; Nebulizer Current (NC)–3.0; Temperature 400° C.; Declustering Potential (DP)–60; Focusing Potential (FP)–265; Declustering Potential 2 (DP2)–15. In MS/MS mode, scan type was product ion, accumulation time was 1.0000 seconds, scan range between 50 and 650 Da and duration time 55 min. All source parameters are the same as above, with collision energy (CE) of –35 V and collision gas (CAD, nitrogen) of 5 psi.

The extracted ion chromatograms (EICs) as detected in the QSTAR® for six of the biomarkers are shown in FIGS. 8A to 8F. The top panel shows the five normal EICs, and the bottom panel of each shows the five CRC EICs. Also, the sensitivity of the QSTAR® is superior as compared to the FTMS, resulting in a greater magnitude in intensity difference between the normal and CRC populations for the selected biomarkers.

Figures 9A, 9B, 9C:
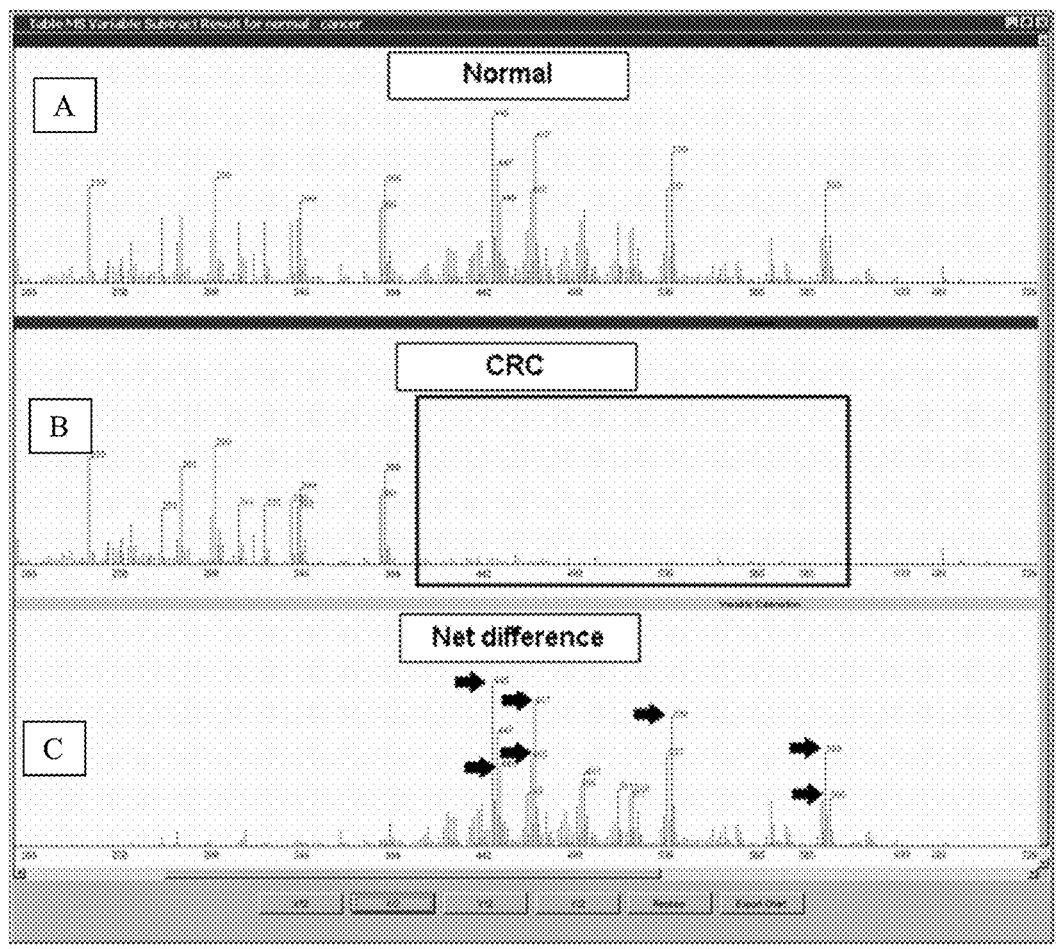
FIGS. 9A-9C show the average extracted mass spectra for retention time window; 16-17 minutes for 5 normal (FIG. 9A) and 5 CRC (FIG. 9B) serum samples as detected on the QSTAR and the net difference (FIG. 9C).

FIG. 9 shows three sets of extracted mass spectra (EMS) for six of the metabolites at a retention time window of 16-17 minutes. FIG. 9A represent the average EMS of the five normal samples, while FIG. 9B represents the average EMS for the five CRC samples. FIG. 9C shows the net difference between the top two spectra. As can be seen, all peaks in the mass range between approximately 445 and 600 Da are barely detectable in the CRC panel (boxed region). All seven of the biomarkers identified on the FTMS platform were detected on the Q-Trap, and were seven of the most abundant peaks in this mass range (highlighted by arrows).

Figure 10A:
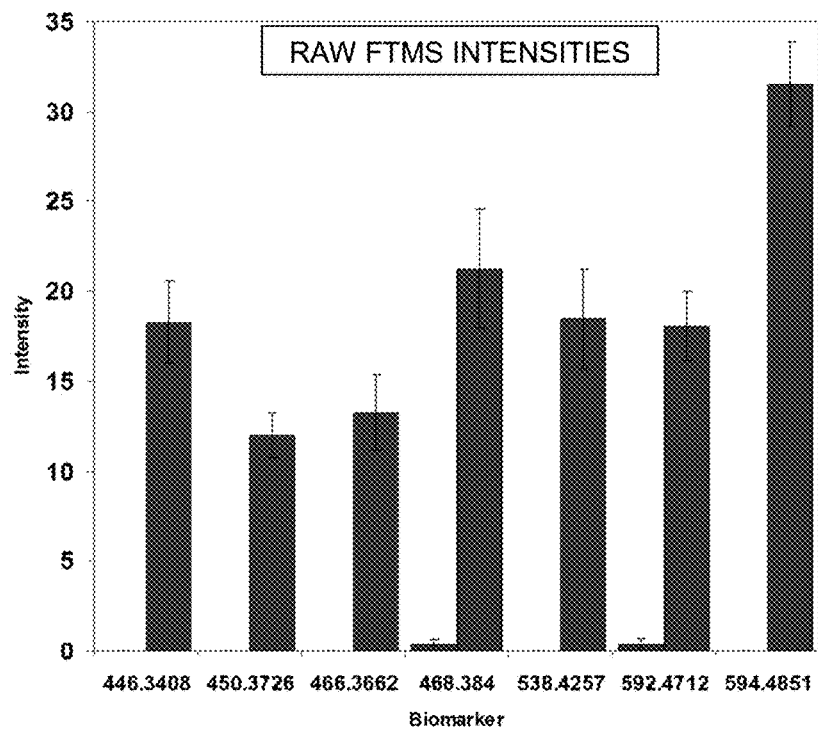
FIGS. 10A-10B show the averaged CRC biomarker intensities of five CRC and five normal samples from FTMS (FIG. 10A) and Q-star (FIG. 10B) analysis. CRC-positive in the first column for each biomarker; normals shown in the second column for each biomarker.
Figure 10B:
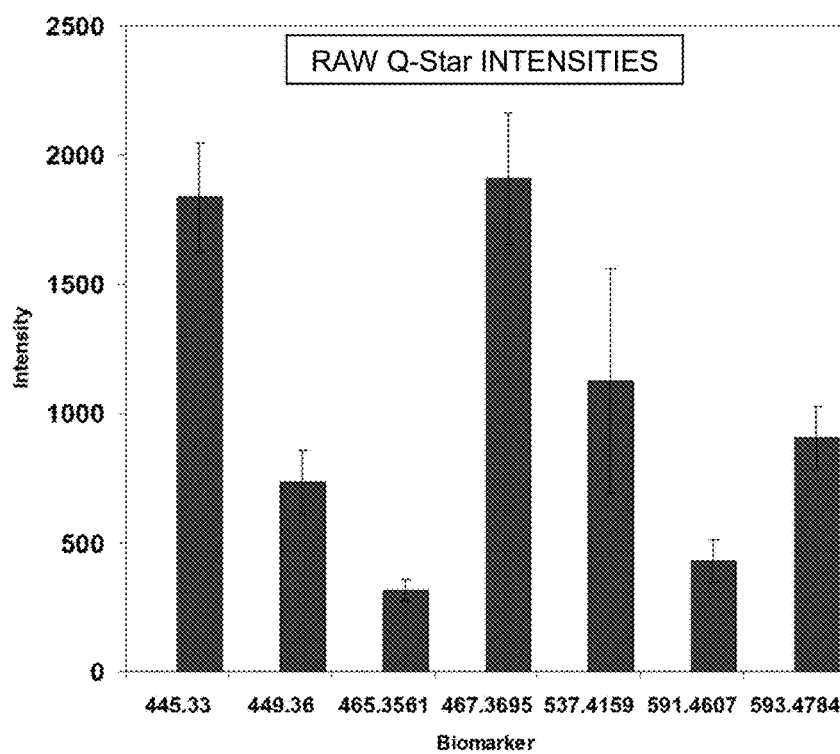

Averages of the seven markers as detected on the FTMS and Q-Star for normals and CRC patients are shown in FIG. 10A and FIG. 10B, respectively. With both platforms, a reproducible and consistent depletion of these molecules was observed in the CRC-positive population.

Figure 11:
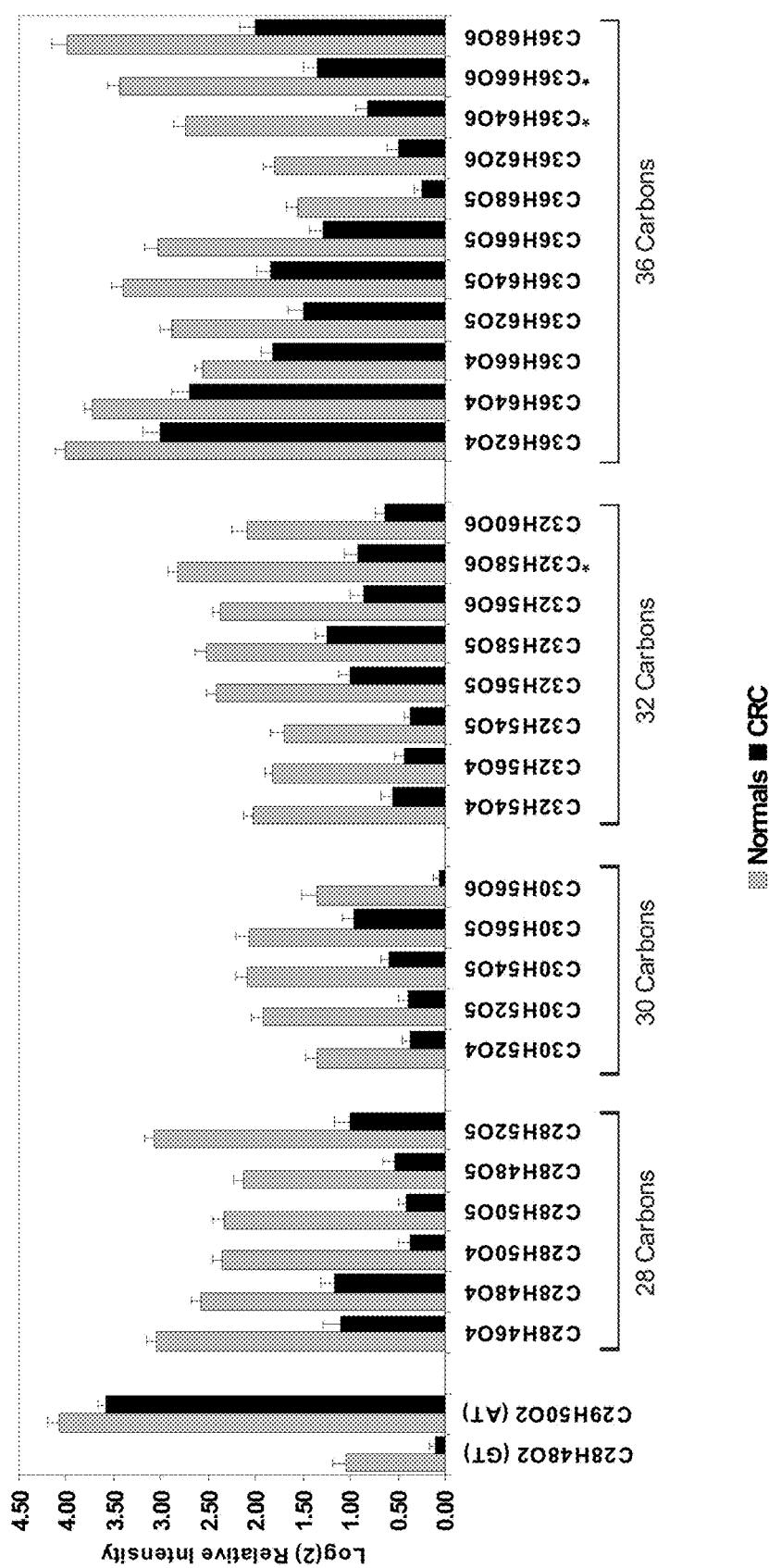
FIG. 11 shows a graph of 30 metabolites that are part of the vitamin E-like family as detected in the FTMS dataset. These can be broken into groups depending on the numbers of carbons they contain. The intensities of gamma (GT) and alpha tocopherol (AT) are also shown.

Although the PAM algorithm had selected seven features with "optimal" diagnostic performance, we re-examined the initial FTMS discovery data for metabolites which appeared to be related to these seven based on molecular formula, chemical properties and ionization information. We were able to identify over 30 molecules related to the seven PAM had selected which all showed decreased expression in the CRC patient cohort. These could further be categorized according to the carbon content, that is, either 28, 32, or 36 carbons (see FIG. 11). In addition, native alpha and gamma-tocopherol were identified and also showed decreased intensity in the CRC cohort (FIG. 11, GT and AT). Based on this information, we re-evaluated which molecules should be carried forward into a high-throughput screening method, and decided to use the six C28-containing molecules, as they consistently appeared to be the most robust discriminators between the two populations (CRC and normals).

Example 3

Structure Elucidation of the Primary Metabolite Biomarkers (NMR, FTIR and MSMS)

The principal characteristics that are normally used for the structural elucidation of novel metabolites are accurate mass and molecular formula determination, polarity, acid/base properties, NMR spectra, and MS/MS or MSn spectra. However, it would be obvious to one skilled in the art that other characteristics of the metabolites could be used in an attempt to determine its structure.

The molecular formulas of the nine preferred diagnostic markers were determined to be $C_{28}H_{46}O_4$, $C_{28}H_{48}O_4$, $C_{28}H_{50}O_4$, $C_{28}H_{48}O_5$, $C_{28}H_{50}O_5$, $C_{28}H_{52}O_5$, $C_{32}H_{58}O_6$, $C_{36}H_{64}O_6$, $C_{36}H_{66}O_6$ based on their accurate neutral mass, polarity, and ionization characteristics. These metabolites have been determined, according to the present invention to consist of a semi-saturated chroman ring and phytyl side chain and therefore consistent with vitamin E-related structures.

The extracts containing the metabolites of interest were subjected to reverse phase LC-MS using a C18 column and analysis by MS as described in the detailed methods above. The retention time for all said vitamin E-like biomarkers is approximately 16.5 minutes under these HPLC conditions.

The conditions of extraction also provide insights about the chemical properties of the biomarkers. All seven of the metabolite markers were extracted into an organic ethyl acetate fraction, indicating that these metabolites are non-polar under acidic condition. Furthermore, they were preferentially ionized in negative APCI mode indicating an acidic proton is present in the molecules.

The structure of a given molecule will dictate a specific fragmentation pattern under defined conditions that is specific for that molecule (equivalent to a person's fingerprint). Even slight changes to the molecule's structure can result in a different fragmentation pattern. In addition to providing a fingerprint of the molecule's identity, the fragments generated by CID can be used to gain insights about the structure of a molecule. MS/MS analysis was carried out on the ABI-QSTAR® XL with all parameters as previously mentioned using nitrogen as the collision gas at 5 psi and CE settings of −25, −35 and −50 volts.

The six metabolites identified as having the best diagnostic ability and suitability for HTS development were subject to MS/MS fragmentation using collision-induced dissociation (CID). The six were selected from the original nine to narrow the group to all C28-containing molecules and to molecules that could be all detected in the same analysis mode. FIG. 12, at Structures A to F, compares the structures of the six molecules to the gamma forms of tocopherol and tocotrienol. This figure can be referred to for the following detailed structural descriptions below.

Figure 20A:
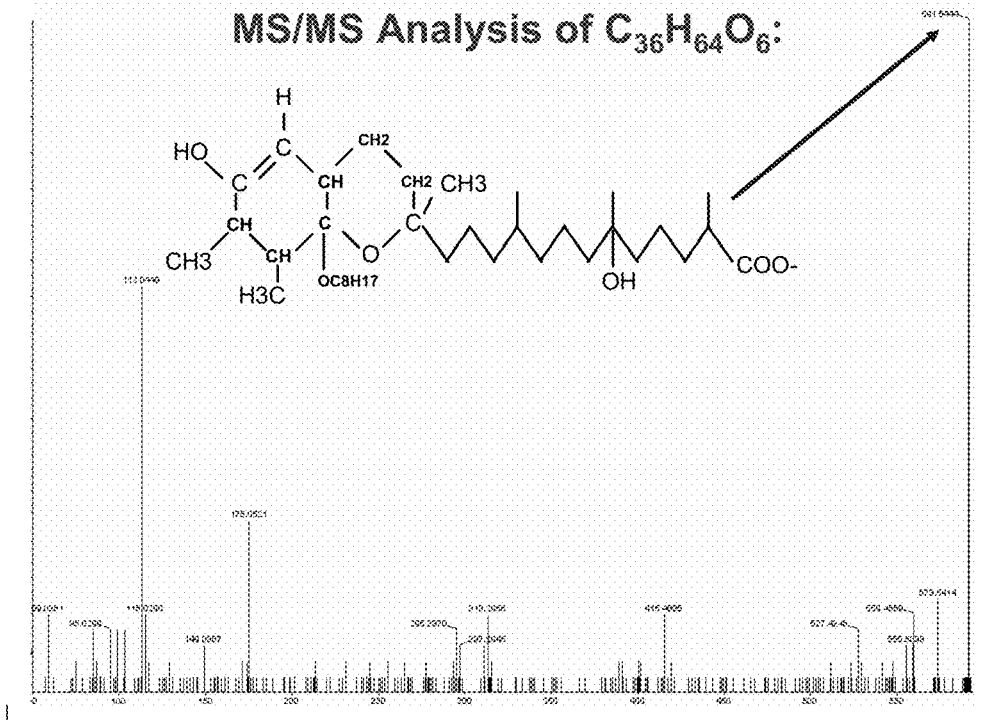
FIGS. 20A-20B show putative structures of key MS/MS fragments for neutral mass biomarker 592.4711 ($C_{36}H_{64}O_6$).
Figure 20B:
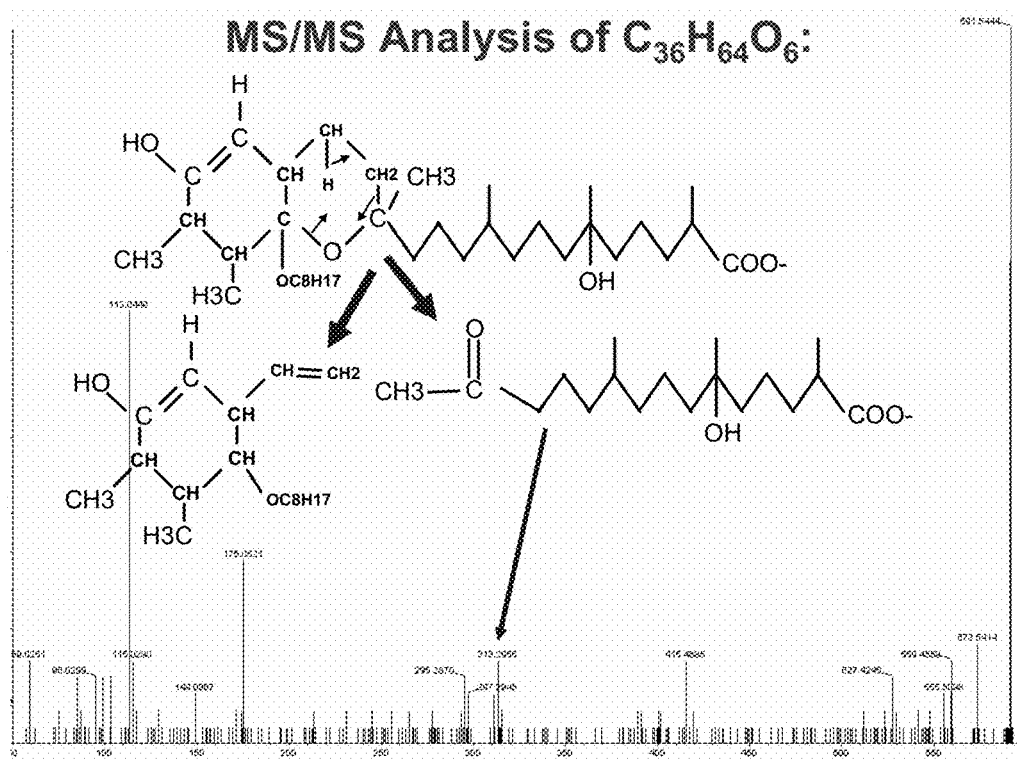
Figure 21A:
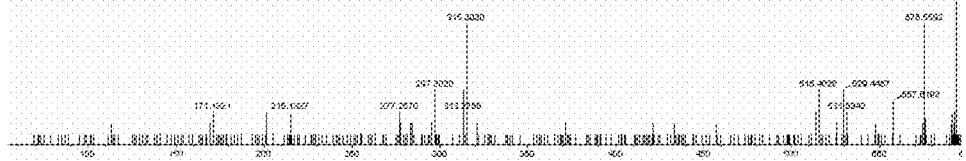
FIGS. 21A-21B show putative structures of key MS/MS fragments for neutral mass biomarker 594.4851 ($C_{36}H_{66}O6$).
Figure 21A:
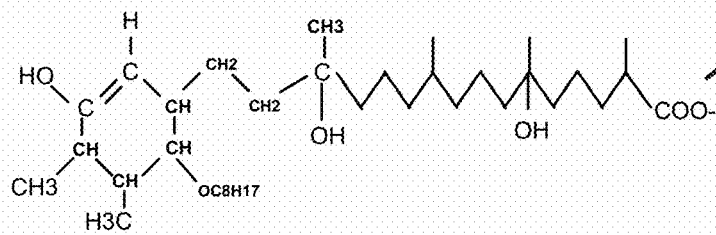
Figure 21A:
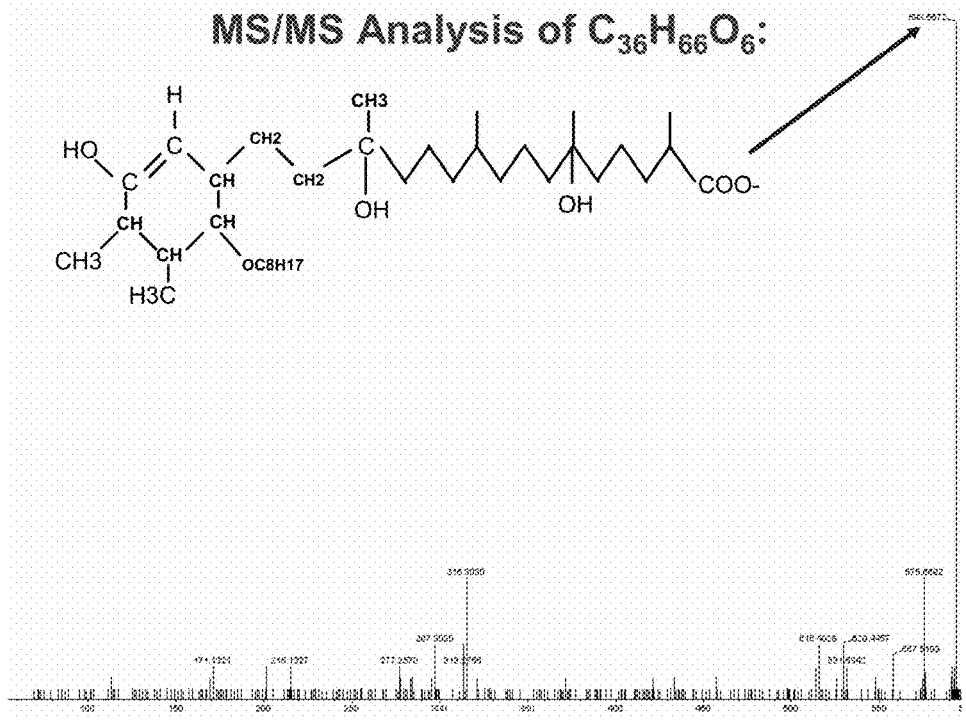
Figure 21B:
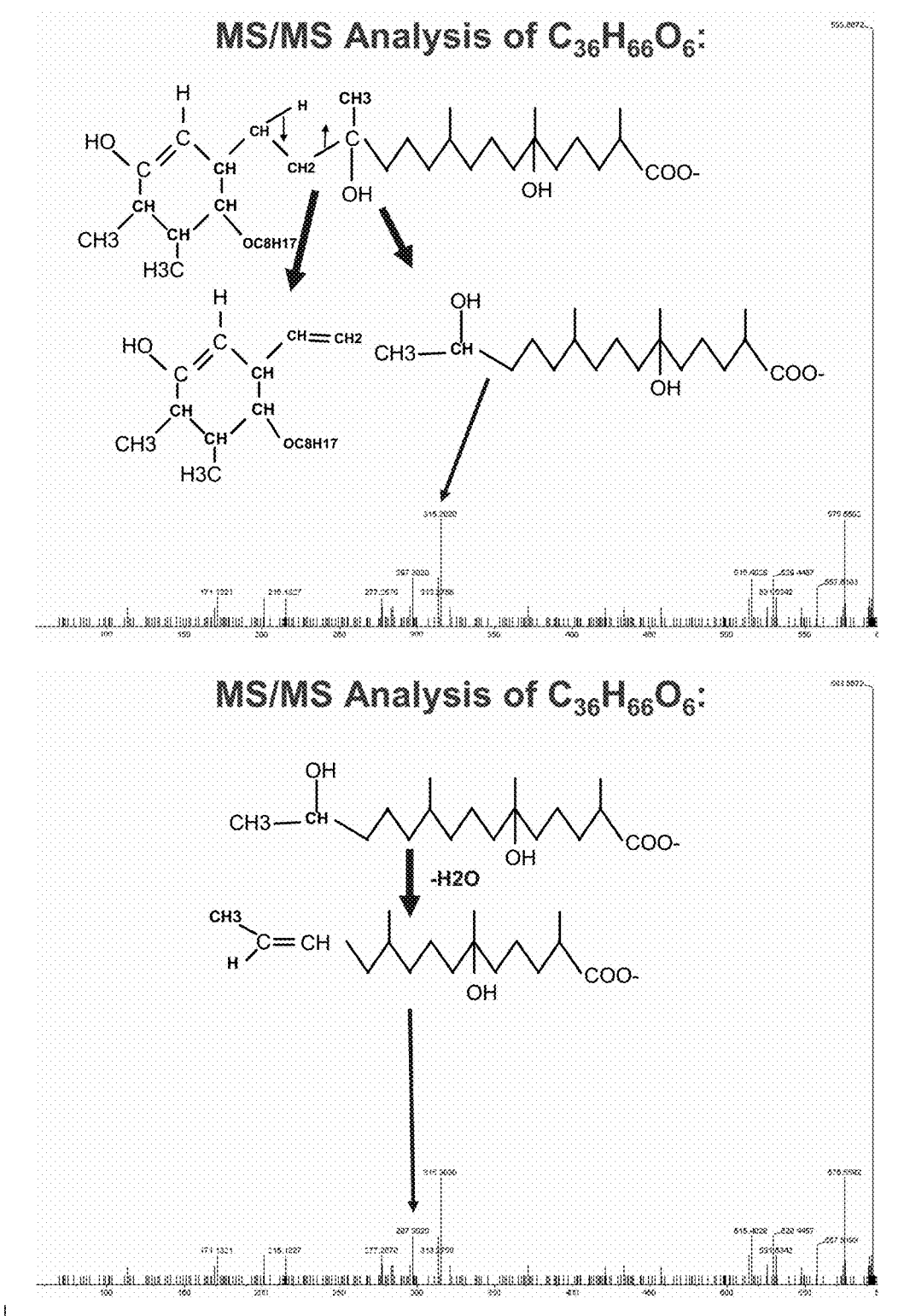
Figure 22:
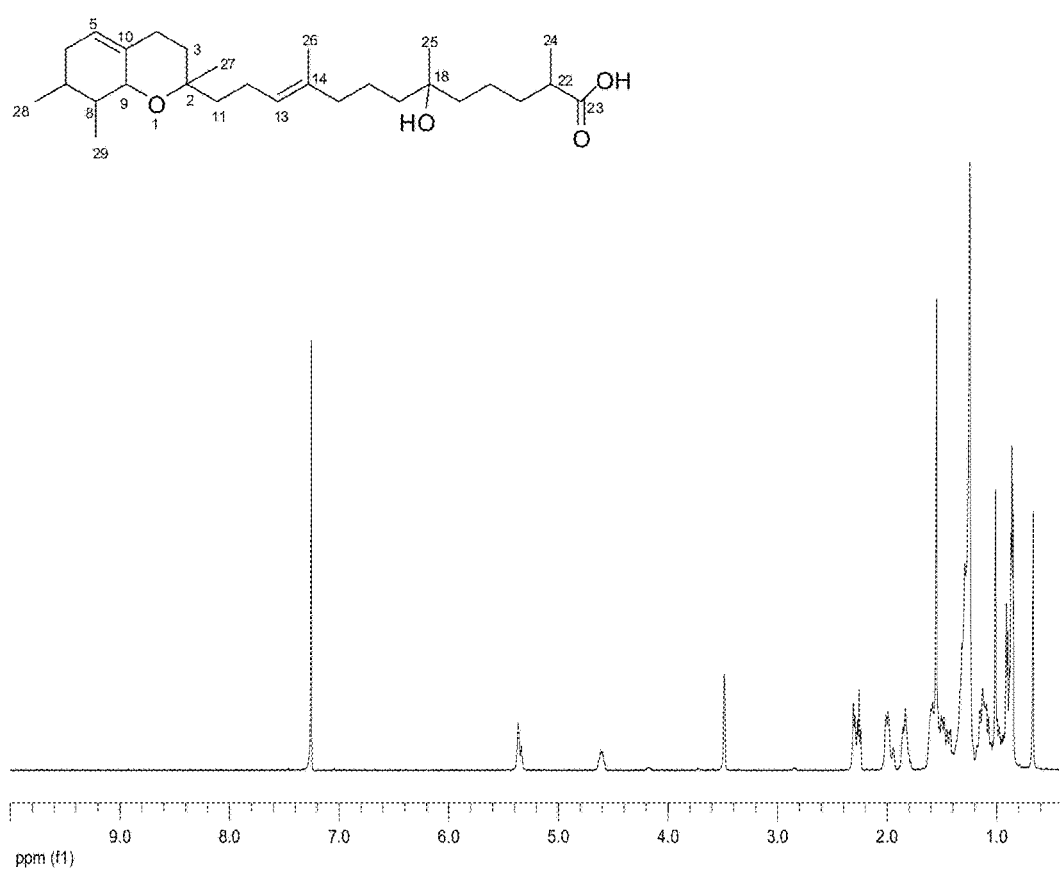
FIG. 22 shows $^1$H-NMR spectra of 448.3406 (C28H48O4)
Figure 23:
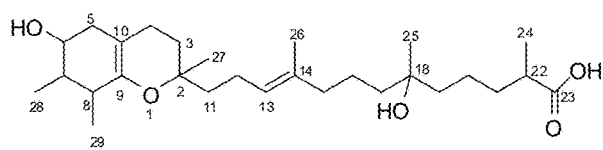
FIG. 23 shows $^1$H-NMR analysis of 464.3522 (C28H48O5)
Figure 23:
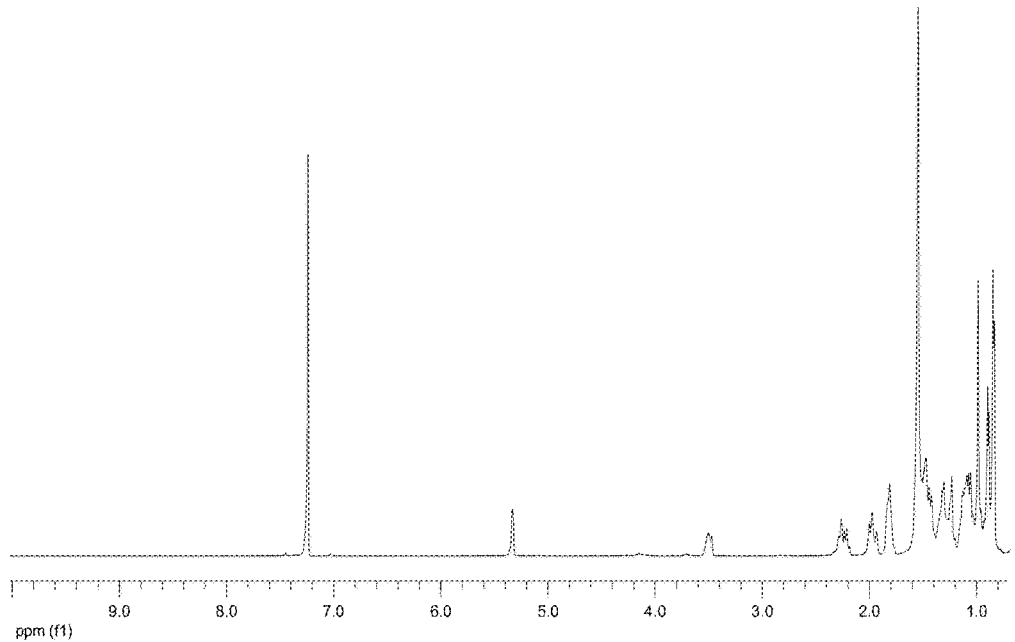
Figure 24:
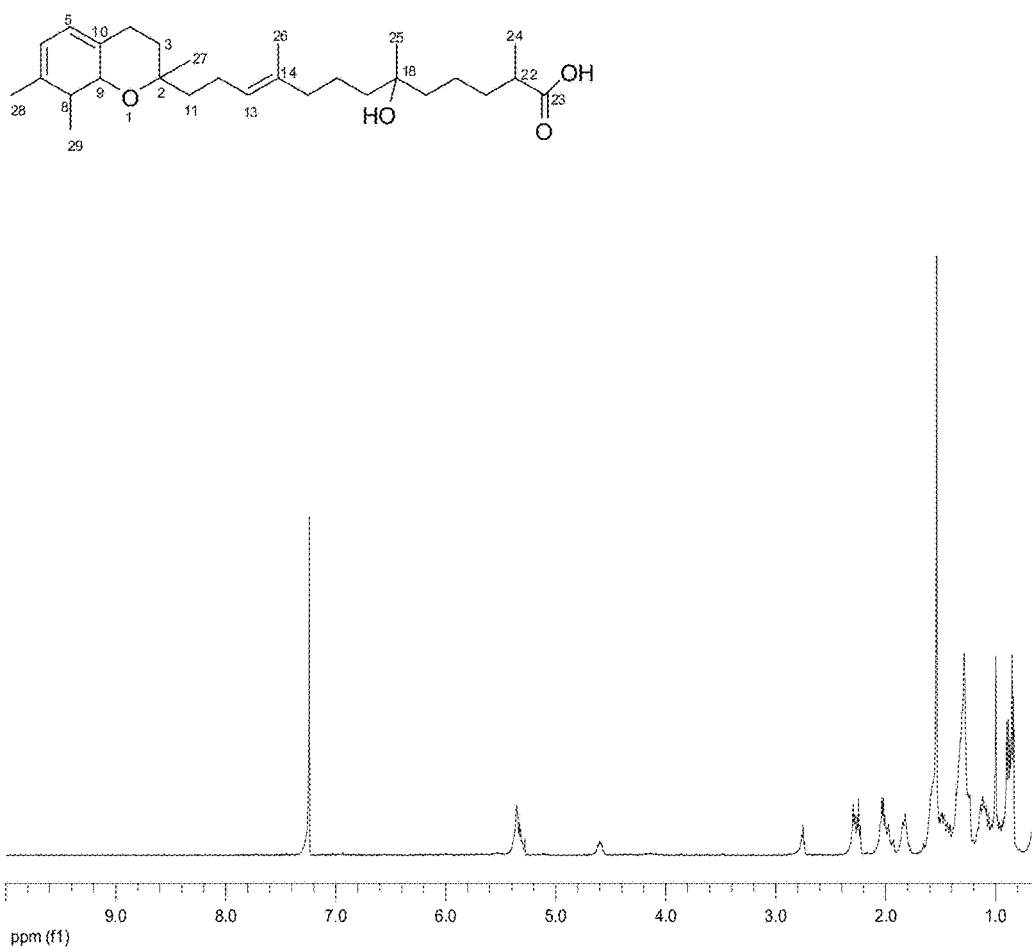
FIG. 24 shows $^1$H-NMR analysis of 446.3406 (C28H46O4)
Figure 25:
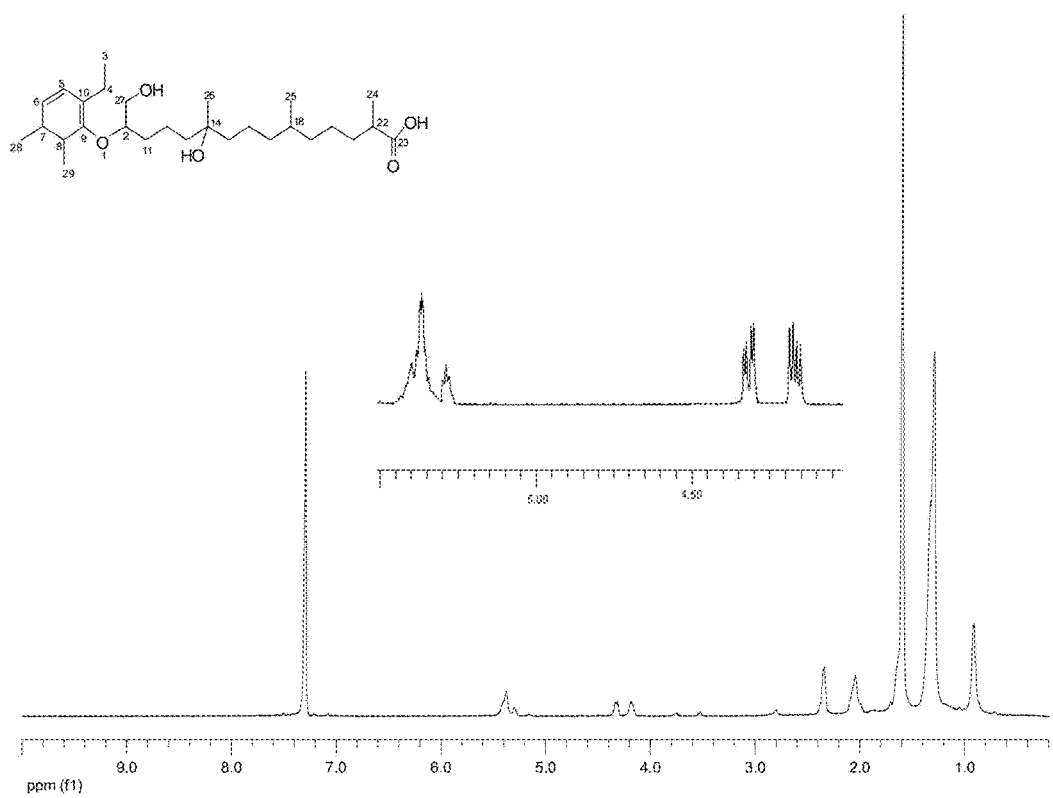
FIG. 25 shows $^1$H-NMR analysis of 466.3661 (C28H50O5)

Based upon the accurate mass MS/MS spectra, putative structures were assigned to each of the biomarkers. In summary, the collective interpretation of the MS/MS spectra of the biomarkers revealed that they all contain a carboxylic acid moiety (as evidenced by a loss of CO2) and at least one hydroxyl moiety (as evidenced by the loss of H2O). Furthermore all of the structures except the C28H46O4 produced a C18HxOy fragment where x≥31 and y≥2, suggestive of a highly saturated fatty acid side chain. This information is consistent with the C28 molecules being metabolites of gamma-tocopherol. The C32 and C36 biomarkers were subsequently hypothesized to be metabolic byproducts resulting from the reaction of gamma-tocopherol and the lipid peroxides of linoleic and oleic acid residues, respectively (FIGS. 19 to 21). The MS/MS spectra support this hypothesis. As would be obvious to someone skilled in the art, minor modifications (including, but not limited to, the location of a double bond, the location of a hydroxyl group, the stereo or chiral orientation of certain carbon atoms) would not distract significantly from the identity of the biomarkers as described. The assignment of the structures to fragments are shown in FIGS. 13 to 21, and listed in Tables 5 to 10 for six of the markers further characterized below. The masses reported for MS-MS results refer to the detected mass, and not the neutral mass. These are referred to as M-1 masses, and will appear to lack one Dalton in mass or a hydrogen within the formula relative to their neutral counterparts mentioned in the previous sections, because they are detected in a negative ionization mode on the mass spectrometer. However, M-1 masses represent the same molecules as the neutral counterparts. The subsequent NMR section refers to neutral masses.

Specifically, MS/MS data obtained in the negative ionization mode for each biomarker was individually analyzed for structural assignment, particularly the placement of functional groups. The MS/MS spectra of each biomarker showed peaks due to loss of water (M-18) and carbon dioxide (M-44). These stipulate the presence of free hydroxyl groups adjacent to a tertiary or secondary carbon molecule and a carboxylic acid group. Loss of the phytol chain fragment was also commonly observed but cleavage of the chain occurred at different places.

Figure 13:
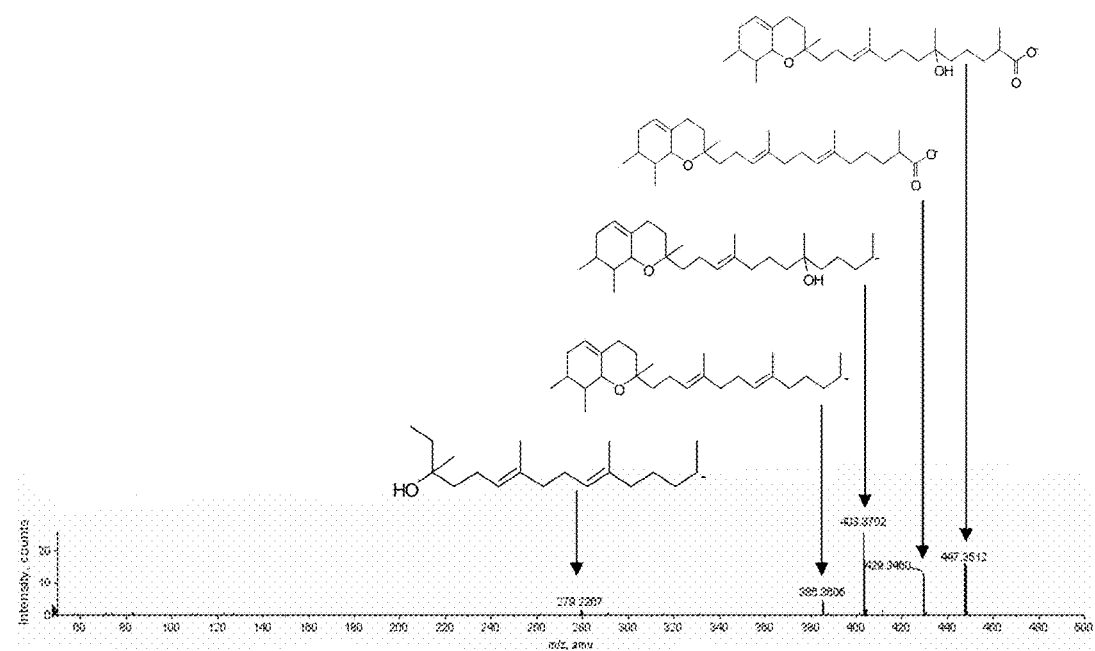
FIG. 13 shows the putative structures of key MS/MS fragments for neutral mass biomarker 448.3726 ($C_{28}H_{48}O_4$).

For $C_{28}H_{48}O_4$ (Table 5, FIG. 13; [M-H]$^-$: C28H47O4$^-$) an initial loss of water and carbon dioxide (m/z 385; $C_{27}H_{45}O$) is observed. Next fragment representing m/z 279 ($C_{19}H_{35}O$) is suggestive of a consequent chroman ring opening at O1-C9 and cleavage of the phytol chain at C10-C4 position.

Figure 14:
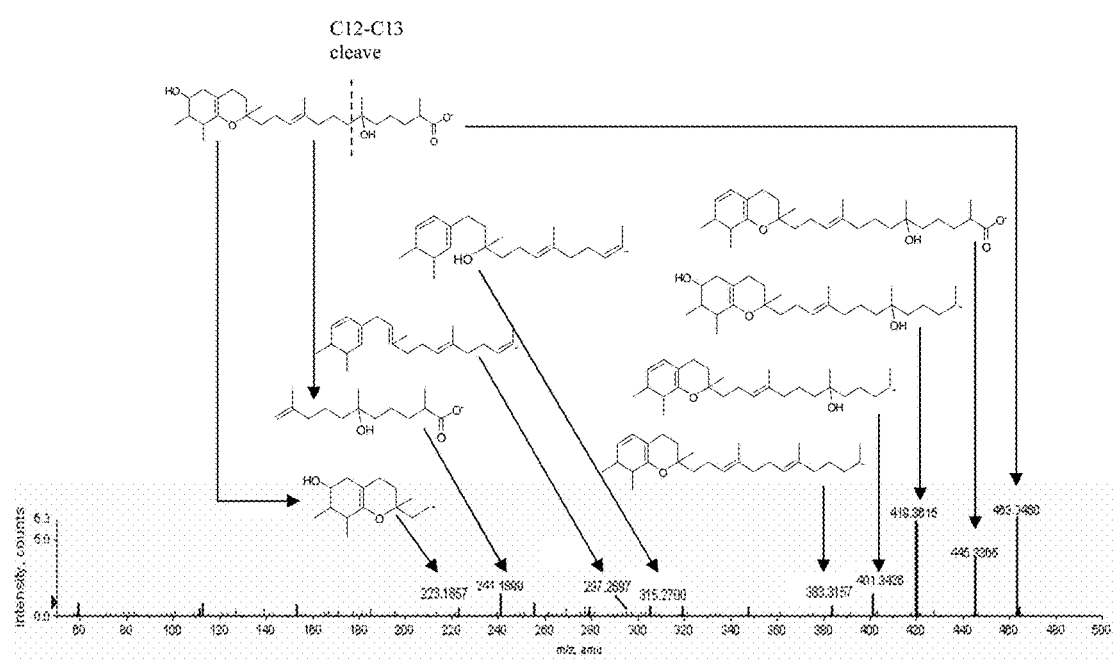
FIG. 14 shows the putative structures of key MS/MS fragments for neutral mass biomarker 464.3522 ($C_{28}H_{48}O_5$).

For $C_{28}H_{48}O_5$ (Table 6, FIG. 14; [M-H]$^-$: $C_{28}H_{47}O_5^-$), which possesses two free hydroxyl functionalities shows loss of two water molecules along with the regular carbon dioxide loss (m/z=383; $C_{27}H_{43}O$). Sequential ring opening at O1-C9 is indicative in here too, followed by the cleavage between C18-C19 generating a fragment of $C_{22}H_{35}O$ (m/z 315). Subsequent signal corresponding to m/z 297 ($C_{22}H_{33}$), representing a loss of a water molecule from the open ring fragment was also observed. Unlike in biomarker 3 (m/z 448.3726) the cleavage of the phytol chain takes place at C12-C13 where the signals for the two halves of the molecules, m/z 241 ($C_{14}H_{25}O_3$), 223 ($C_{14}H_{23}O_2$) were observed in the MS/MS spectra of C28H48O5. This particular fragmentation is a strong evidence for the distribution of the functional groups between the chroman ring and the phytol chain.

Figure 15:
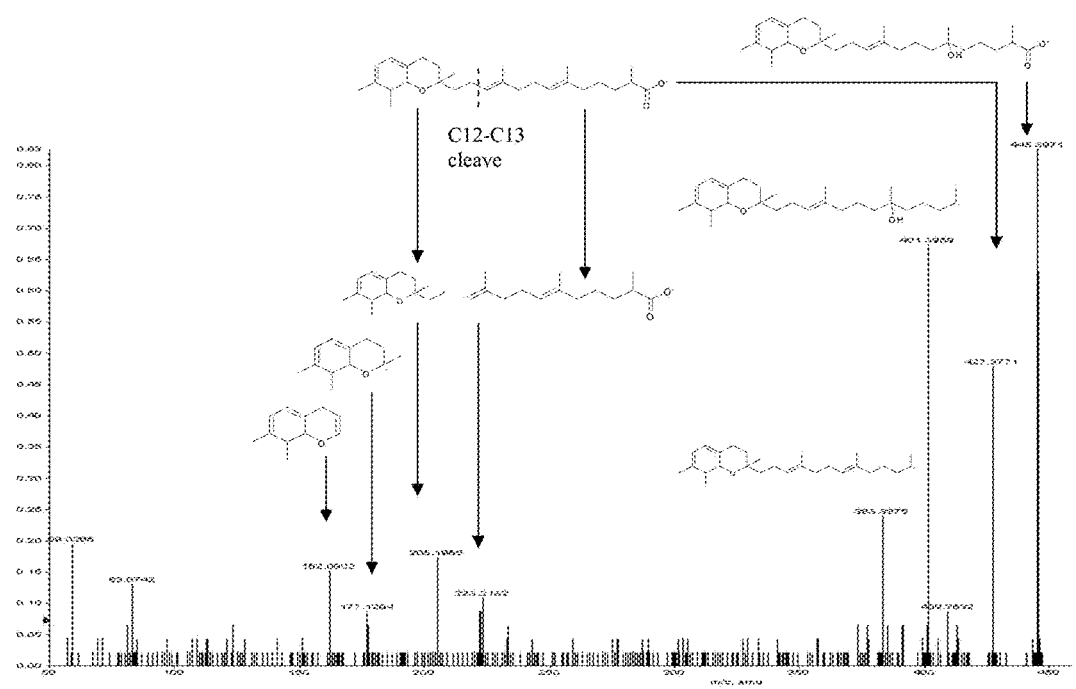
FIG. 15 shows the putative structures of key MS/MS fragments for neutral mass biomarker 446.3522 ($C_{28}H_{46}O_4$).

MS/MS spectrum of $C_{28}H_{46}O_4$ (Table 7, FIG. 15; [M-H]$^-$: $C_{28}H_{45}O_4^-$) exhibit a similar pattern to that of $C_{28}H_{48}O_5$. Loss of water (m/z 427; $C_{28}H_{43}O_3$) and carbon dioxide (m/z 401; $C_{27}H_{45}O_2$) observed to be both alternate and instant (m/z 383; $C_{27}H_{43}O$). Like in $C_{28}H_{48}O_5$ the cleavage of the phytol chain takes place at C12-C13, after an initial loss of water between C17-C18, generating a fragment of m/z 223 ($C_{14}H_{23}O_2$). The other counter fragment, $C_{14}H_{21}O$ (m/z 205) is also observed and is also representative as the parent ion of next two consecutive fragments, m/z 177 ($C_{12}H_{17}O$) and 162 ($C_{11}H_{14}O$) indicating losses of $C_2H_8$ and $CH_3$ respectively.

Figure 16:
FIG. 16 shows the putative structures of key MS/MS fragments for neutral mass biomarker 466.3661 ($C_{28}H_{50}O_5$).

Interestingly, in $C_{28}H_{50}O_5$ (Table 8, FIG. 16; [M-H]$^-$: $C_{28}H_{49}O_5^-$), in addition to the accustom losses of water (m/z 447; $C_{28}H_{47}O_4$) and carbon dioxide (m/z 421; $C_{26}H_{45}O_3$), loss of an ethanol fragment (m/z 433; $C_{27}H_{45}O_4$) followed by an ethylene fragment (m/z 405; $C_{26}H_{45}O_3$) is also detected. These observations signify the proposed ring opening at C2-C3 of the chroman ring and hydroxylation of the C27 methyl group, generating viable precursors for methanol and ethylene fragments. Several different fragments were observed due to the fragmentation of the phytol side chain. Cleavage at C18-C19 (m/z 349; $C_{22}H_{37}O_3$), cleavage at C1-C2 after an initial water loss between C18-C17 (m/z 297; $C_{18}H_{33}O_3$) followed by a loss of another water molecule (m/z 279; $C_{18}H_{31}O_2$) and cleavage at C15-C16 (m/z 185; C13H19O3) were among them. The anticipated fragmentation between C12-C13 were also observed as two counter molecular-ion halves, m/z 241 ($C_{15}H_{29}O_2$) and 223 ($C_{13}H_{19}O_3$).

Figure 17:
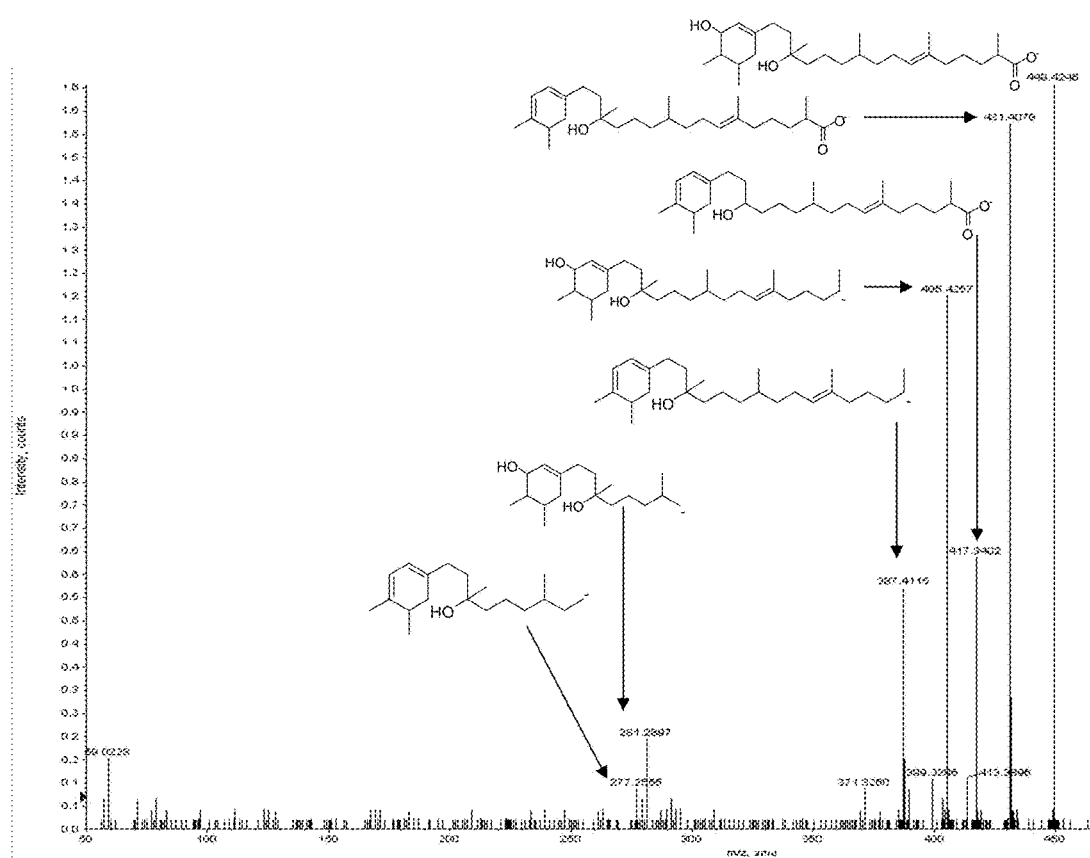
FIG. 17 shows putative structures of key MS/MS fragments for neutral mass biomarker 450.3726 ($C_{28}H_{50}O_4$).

The MS/MS spectrum of $C_{28}H_{50}O_4$ (Table 9, FIG. 17; [M-H]$^-$: $C_{28}H_{49}O_4^-$) also displayed the expected water and carbon dioxide losses (m/z 431; $C_{28}H_{49}O_4$, 405; $C_{27}H_{49}O_2$).

Similar to that of $C_{28}H_{48}O_5$ this showed a fragment due to the loss of two water molecules (m/z 413; $C_{28}H_{45}O_2$). This suggests the presence of two free hydroxyl groups in the structure. Cleavage of the phytol ring takes place at two positions, between C15-C16 (m/z 281; $C_{18}H_{33}O_2$) and between C16-C17 followed by a loss of water molecule (m/z 277; $C_{19}H_{33}O$). These fragments establish the absence of a hydroxyl group in the phytol chain and the unsaturation between C17-C18. The structure of biomarker 7 is assembled accordingly.

Figure 18:
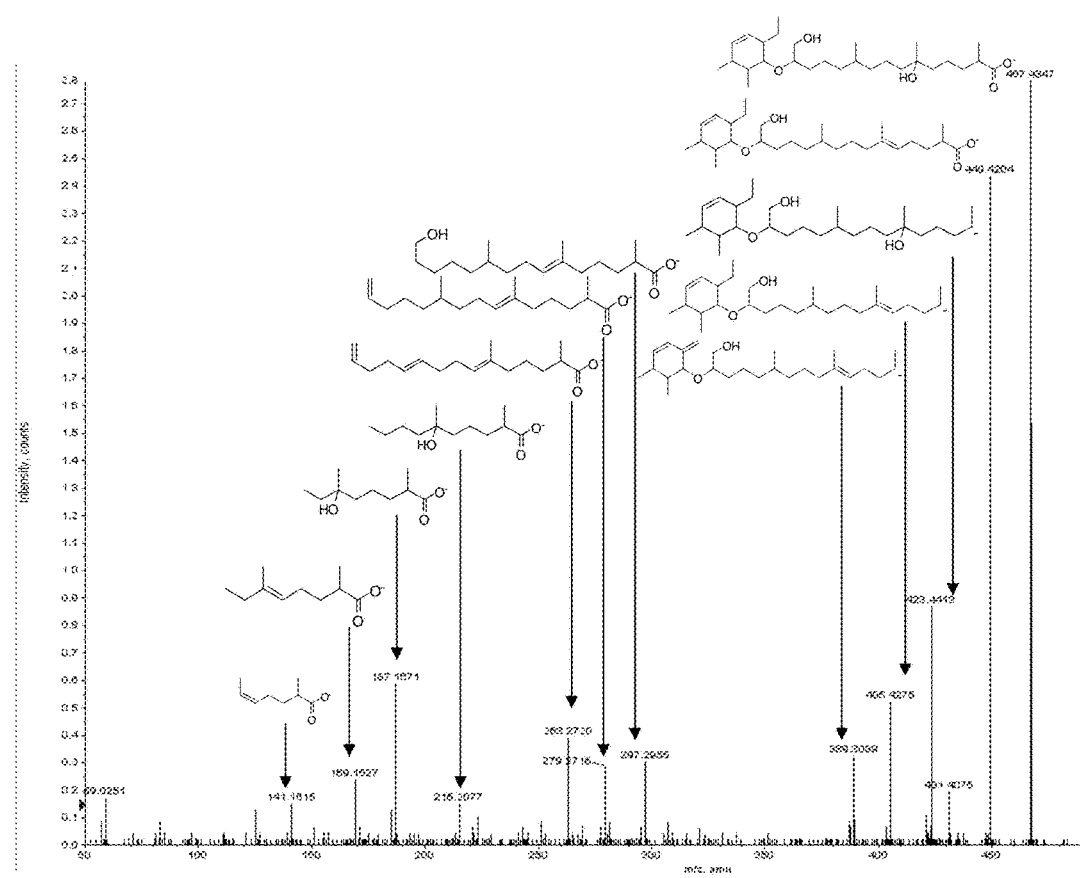
FIG. 18 shows putative structures of key MS/MS fragments for neutral mass biomarker 468.3840 ($C_{28}H_{52}O_5$).
Figure 19A:
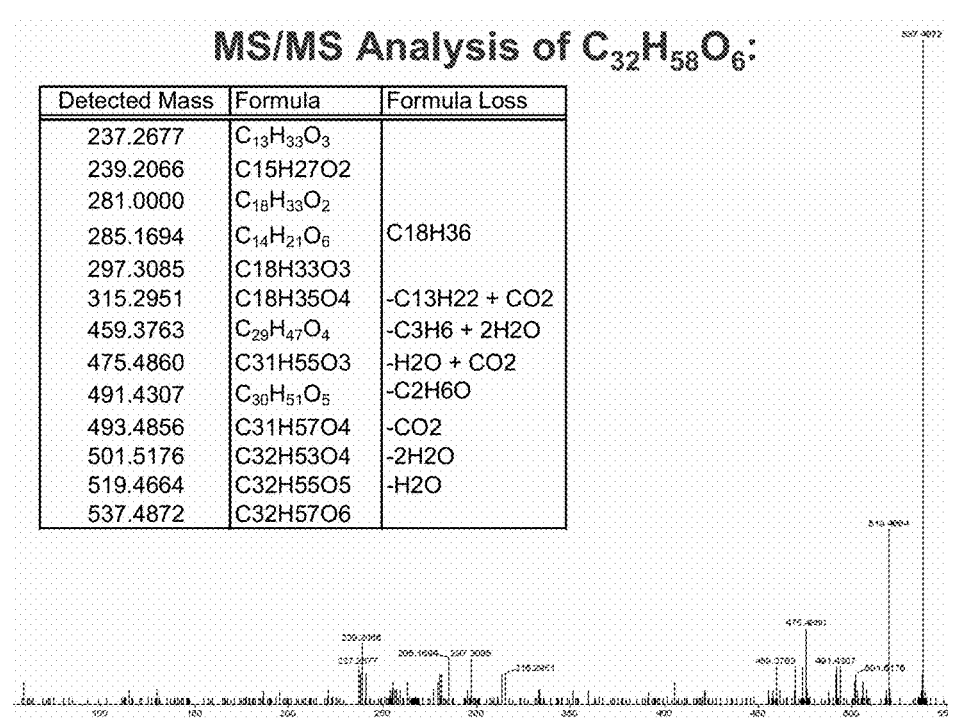
FIGS. 19A-19B show putative structures of key MS/MS fragments for neutral mass biomarker 538.4259 ($C_{32}H_{58}O6$).
Figure 19B:
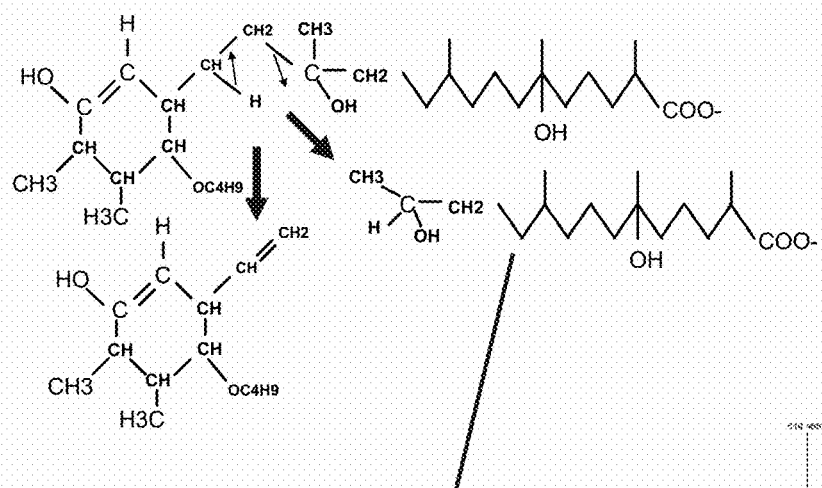
Figure 19B:
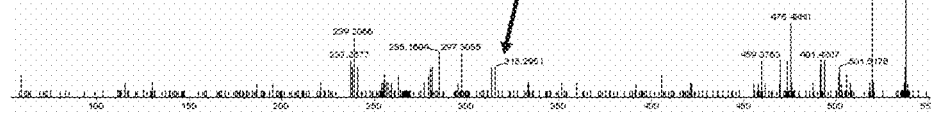
Figure 19B:
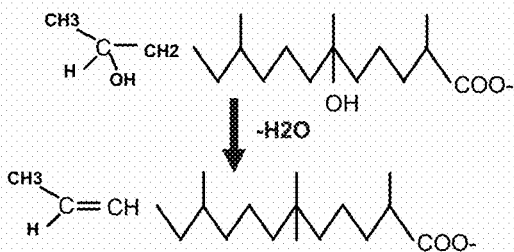
Figure 19B:
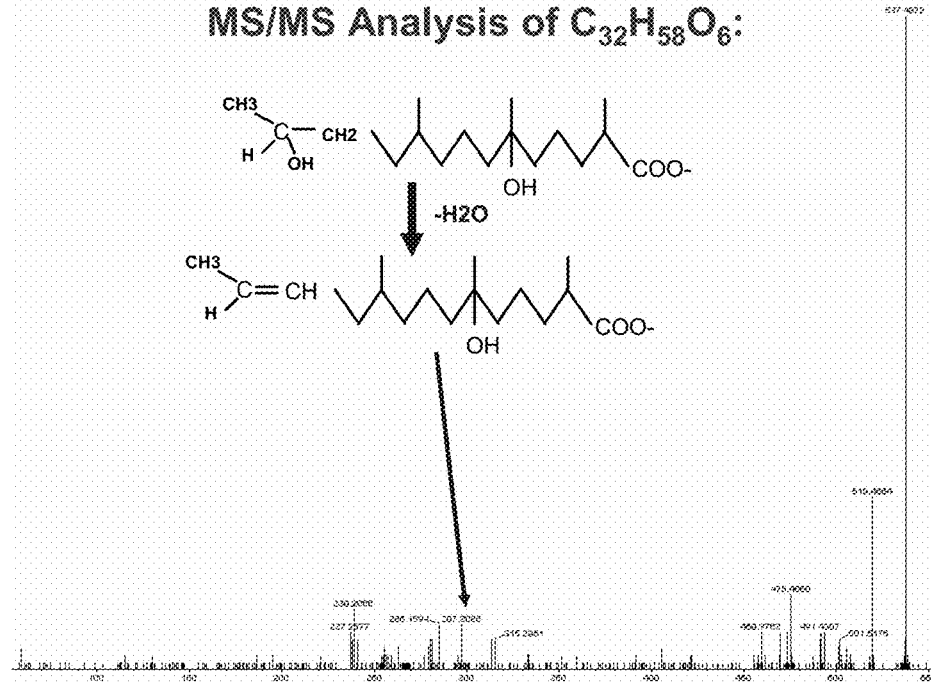

The MS/MS spectra of $C_{28}H_{52}O_5$ (Table 10, FIG. 18; [M-H]$^-$: $C_{28}H_{51}O_5{}^-$) indicated loss of two water molecules (m/z 431; $C_{28}H_{47}O_3$) and another fragment for a loss of water and a carbon dioxide molecules at the same time (m/z 405; $C_{27}H_{49}O_2$) suggesting for the presence of two free hydroxyl groups and a carbonyl functionality. Some of the fragments observed here are identical to that of $C_{28}H_{50}O_5$, of which the only difference from $C_{28}H_{52}O_5$ is an excess degree of unsaturation. Cleavage at C1-C2 after an initial water loss between C18-C17 (m/z 297; $C_{18}H_{33}O_3$) followed by a loss of another water molecule (m/z 279; $C_{18}H_{31}O_2$) were among them. Subsequent loss of a $CH_4$ from $C_{18}H_{31}O_2$ is represented by the molecular ion peak m/z 263 ($C_{17}H_{27}O_2$). The molecular ion peak of m/z 215 ($C_{12}H_{23}O_3$) is suggestive of a fragment of the phytol chain due to C13-C14 bond cleavage followed by a loss of $CH_3$. Fragment due to the cleavage of the phytol chain at C15-C16 (m/z 187; $C_{10}H_{19}O_3$) was observed as the parent ion for the next two consecutive fragments, resulted due to loss of a water molecule (m/z 169; $C_{10}H_{17}O_2$) and an ethylene fragment (m/z 141; $C_8H_{13}O_2$) respectively from $C_{10}H_{19}O_3$.

In addition to the six C28-containing molecules, MSMS analysis of the non C28 vitamin E-like molecules was also performed as shown in FIGS. 19 through 21. These C32 and C36 biomarkers thought to be metabolic byproducts resulting from the reaction of gamma-tocopherol and the lipid peroxides of linoleic and oleic acid residues, respectively. The MS/MS spectra support this hypothesis as shown in FIGS. 19 to 21.

For the NMR and FTIR methods, all chemicals and media were purchased from Sigma-Aldrich Canada Ltd., Oakville, ON. All solvents were HPLC grade. Analytical thin layer chromatography (TLC) was carried out on precoated silica gel TLC aluminum sheets (EM science, Kieselgel 60 $F_{254}$, 5×2 cm×0.2 mm). Compounds were visualized under UV light (254/366 nm) or placed in iodine vapor tank and by dipping the plates in a 5% aqueous (w/v) phosphomolybdic acid solution containing 1% (w/v) ceric sulfate and 4% (v/v) $H_2SO_4$, followed by heating. Preparative thin layer chromatography (prep TLC) was performed on silica gel plates (EM science, 60 $F_{254}$ 20×20 cm, 0.25 mm thickness). Compounds were visualized under UV light and in iodine. HPLC analysis were carried out with a high performance liquid chromatograph equipped with quaternary pump, automatic injector, degasser, and a Hypersil ODS column (5 μm particle size silica, 4.6 i.d×200 mm) and semi-prep column (5 μm particle size silica, 9.1 i.d×200 mm), with an inline filter. Mobile phase: linear gradient $H_2O$-MeOH to 100% MeOH in a 52 min period at a flow rate 1.0 ml/min.

NMR spectra were recorded on a Bruker Avance spectrometers; for $^1H$ (500 MHz), δ values were referenced to $CDCl_3$ ($CHCl_3$ at 7.24 ppm) and for $^{13}C$ NMR (125.8 MHz) referenced to $CDCl_3$ (77.23 ppm). High resolution (HR) mass spectra (MS) were recorded on Bruker apex 7T Fourier transform ion cyclotron resonance (FT-ICR) and QStar XL TOF mass spectrometers with atmospheric pressure chemical ionization (APCI) source in the negative mode. Fourier transform infrared (FT-IR) spectra were recorded on a Bio-Rad FTS-40 spectrometer. Spectra were measured by the diffuse reflectance method on samples dispersed in KBr.

A semi-purified pooled HPLC fraction (32 mg) of serum extracts which exhibited a mixture of gamma-tocopherol-like and gamma-tocotrienol-like compounds in $^1H$ NMR spectrum was purified by preparative TLC to yield the structures as shown in FIG. 12, Structures C (3, 3.6 mg), D (4, 2.5 mg), E (5, 3.4 mg), and F (6, 4.6 mg). We refer to these novel structures as gamma-tocoenoic acids in the following section.

The molecular formula of gamma-tocoenoic acid 3; FIG. 12, Structure C (3) was determined as $C_{28}H_{48}O_4$ (neutral) by HRAPCI-MS, possessing five degrees of unsaturation. The FTIR absorptions at 3315 (br) and 1741 $cm^{-1}$ suggested hydroxyl and carbonyl groups. Analysis of the $^1H$ and $^{13}C$ NMR spectroscopic data (Tables 11 and 12) indicated the presence of six methyl groups, four olefinic carbons and a long phytol chain as present in gamma-tocotrienol; FIG. 12, Structure B (2)[50, 51]. Analysis of the HMQC and HMBC data were instrumental in the assignment of the structure. The only carbonyl-like carbon present at $δ_C$ 173.8 (C-23) which displayed one long range correlation with a methine proton at $δ_H$ 2.24 (H-22) was confirmed as carboxylic acid functionality using the loss of carbon dioxide observed in its MS/MS spectra. Likewise, the carbon at $δ_C$ 74.2 (C-9) displayed correlations with a methylene proton at $δ_H$ 2.28 (H-4) which together with another methylene proton at $δ_H$ 2.28 (H-6) showed HMBC correlations with a $sp^2$ carbon at $δ_C$ 130.5 (C-10). These are indicative of a semi-saturated chroman ring system as present in gamma-tocotrienol (FIG. 12, Structure B). On the phytol side chain, long range correlations were observed between methyl protons at $δ_H$ 1.55 (H-26) and $sp^2$ carbon at $δ_C$ 123.2 (C-13), methylene protons around $δ_H$ 1.01 (H-12, H-15) and $sp^2$ carbon at $δ_C$ 140.2 (C-14), and methyl protons around $δ_H$ 0.91 (H-25) and the quaternary carbon at $δ_C$ 56.6 (C-18). The MS/MS spectral analysis confirms fragments due to a loss of water and carbon dioxide and ring opening at C9-O1 position followed by the loss of phytol side chain fragment (m/z 279; $C_{18}H_{31}O_2$). Hence, the structure of this gamma-tocoenoic acid was assigned as 3 (FIG. 12, Structure C).

Gamma-Tocoenoic acid 4; FIG. 12, Structure D (4) had a molecular formula of $C_{28}H_{48}O_5$ (HRAPCI-MS) indicating five degrees of unsaturation. The FTIR absorptions at 3437 (br) and 1743 $cm^{-1}$ suggested hydroxyl and carbonyl groups. The $^1H$ and $^{13}C$ NMR spectra were very similar to that of C28H48O4. The only difference included an additional hydroxy group, indicated by an additional $H_2O$ loss in the MS/MS fragmentations when compared to that of C28H48O4, which was assigned on C-6 considering the $^1H$-$^1H$ COS Y correlations of the methylene protons, H-5 ($δ_H$ 2.21-2.25) and H-7 (($δ_H$ 1.47-1.53), to the methine proton, H-6 ($δ_H$ 3.69-3.71). MS/MS spectral analysis also confirmed the presence of the carboxylic group indicative by the loss of $CO_2$ molecule and MS/MS fragments due to the cleavage between C12 and C13, $C_{14}H_{25}O_3$ (m/z 241) and $C_{14}H_{23}O_2$ (m/z 223), which further supports the assignment of the diene on the phytol side chain and hydroxylation on the chroman ring. Hence, the structure of gamma-tocoenoic acid 4 was assigned as shown in FIG. 12, Structure D.

Gamma-Tocoenoic acid 5; FIG. 12, Structure E (5) had a molecular formula of $C_{28}H_{46}O_4$ (HRAPCI-MS) indicating six degrees of unsaturation. The FTIR absorptions at 3125 (br) and 1736 $cm^{-1}$ suggested the presence of hydroxyl and carbonyl groups. The $^1H$ and $^{13}C$ NMR spectra were very similar to that of C28H48O4; the only difference was an additional double bond in the semi-saturated chroman ring system resulted by highly liable dehydration between C6 and C7. The MS/MS spectral analysis confirmed the presence of the carboxylic group, fragments due to water loss as well as the fragments due to the cleavage between C12 and C13, $C_{14}H_{23}O_2$ [m/z 223; ($C_{14}H_{25}O_3$—$H_2O$) and $C_{14}H_{21}O$ (m/z 205; $C_{14}H_{23}O_2$—$H_2O$) similar to those observed for C28H48O5. Hence, the structure of gamma-tocoenoic acid 5 was assigned as shown in FIG. 12, Structure E.

Gamma-Tocopheric acid 6 (FIG. 12, Structure F) had a molecular formula of $C_{28}H_{50}O_5$ (HRAPCI-MS) indicating four degrees of unsaturation. The FTIR absorptions at 3314 (br) and 1744 cm$^{-1}$ suggested hydroxyl and carbonyl groups. The $^1H$ and $^{13}C$ NMR spectra showed some similarities to that of C28H48O4 and C28H48O5 but there were some significant differences observed as well. The similarities include the presence of six methyl groups, four sp$^2$ hybridized carbons, and a carbonyl-like carbon at $\delta_C$ 174.1 (C-23), displaying long range correlation with a methine proton at $\delta_H$ 2.28 (H-22). The differences include the opening of the chroman ring system, with the $^1H$ NMR spectrum displaying a spin system containing two methylene protons at $\delta_H$ 4.27-4.29 (H-27a, dd, J=4.0, 12.0 Hz) and $\delta_H$ 4.04-4.14 (H-27b, dd, J=6.0, 12.0 Hz) coupled together and with a methine proton at $\delta_H$ 5.12 (H-2, m), established using $^1H$-$^1H$ COS Y and $^1H$-$^1H$ homonuclear decoupling experiments. In addition HMBC and $^1H$-$^1H$ COS Y of C28H50O5 did not exhibit the long range correlations between methyl protons and sp$^2$ carbon which was a common fact for the other tocotrienoic acids C28H48O4, C28H48O5 and C28H46O4, indicating the saturation of the phytol side chain, which confine this structure as a derivative of gamma-tocopheric acid. The MS/MS spectral analysis confirmed the presence of the carboxylic group, fragments due to water loss as well as the two common fragments as a consequence of the cleavage between C12 and C13, m/z 241 and 223. This suggests that despite the ring opening between C2 and C3 and the saturation of the phytol chain, the rest of the structural aspects are similar to those of other identified tocoenoic acids C28H48O4, C28H48O5 and C28H46O4. Hence, the structure of gamma-tocopheric acid was assigned as 6 of FIG. 12, Structure F.

The structures of the other two biomarkers that could not be isolated by prep TLC using the tested solvent systems, $C_{58}H_{50}O_4$ (7, FIG. 12, Structure G) and $C_{28}H_{52}O_5$ (8, FIG. 12, Structure H) were assembled by evaluating their MS/MS fragmentation data, as shown in 12, Structures G and H, respectively.

The metabolites were isolated from serum and the structure re-confirmed by NMR. A total of 200 mL of serum was extracted with ethyl acetate (500 mL, 3×), dried using the nitrogen evaporator and the extract reconstituted in 4 mL of methanol. The extract was subjected to LC/MS in fraction collection mode (100 μL injections, 40×) with fractions collected in 1 min windows for 52 mins. The expected metabolites, which eluted within 15-17 mins, were pooled and concentrated to dryness using the nitrogen evaporator (about 32 mg). The semi purified fraction which exhibited a mixture of tocopherol related compounds in $^1H$ NMR spectrum was subjected to prep TLC, developed with $CH_2Cl_2$—hexane (2:1) to yield gamma-tocoenoic acid 3 (3.6 mg) and gamma-tocoenoic acid 4 (2.5 mg). The remaining bands were combined (about 22 mg) and further applied to prep TLC using cyclohexane-$CH_2Cl_2$-EtOAc (35:5:1, for two times) to yield gamma-tocoenoic acid 5 (3.4 mg), gamma-tocopheric acid 6 (4.6 mg) and a fraction (6.6 mg) which turned out to be a mixture.

Gamma-Tocoenoic Acid 3

TLC $R_f$=0.81 (cyclohexane-$CH_2Cl_2$-EtOAc, 10:4:1); for $^1H$ and $^{13}C$ NMR spectra, see Tables 11 and 12; FTIR (cm$^{-1}$) 3315 (br), 2935, 2852, 1741, 1465, 1377, 1178, 726; HRAPCI-MS m/z: measured 447.3490 ([M-H]$^-$, calcd. 447.3480 for $C_{28}H_{47}O_4$). MS/MS m/z (relative intensity): 447 ([M-H]$^-$, 50%), 429 (45%), 403 (100%), 385 (20%), 279 (10%).

Gamma-Tocoenoic Acid 4

TLC $R_f$=0.21 (cyclohexane-$CH_2Cl_2$-EtOAc, 10:4:1); for $^1H$ and $^{13}C$ NMR spectra, see Tables 11 and 12; FTIR (cm$^{-1}$) 3347 (br), 2935, 2868, 1743, 1466, 1377, 1057, 958; HRAPCI-MS m/z: measured 463.3449 ([M-H]$^-$, calcd. 463.3429 for $C_{28}H_{47}O_5$); MS/MS m/z (relative intensity): 463 ([M-H]$^-$, 100%), 445 (50%), 419 (90%), 401 (25%), 241 (20%).

Gamma-Tocoenoic Acid 5

TLC $R_f$=0.79 (cyclohexane-$CH_2Cl_2$-EtOAc, 10:4:1, UV active spot); for $^1H$ and $^{13}C$ NMR spectra, see Tables 11 and 12; FTIR (cm$^{-1}$) 3125 (br), 2941, 2855, 1736, 1556, 1466, 1377, 1177, 1008, 773; HRAPCI-MS m/z: measured 445.3333 ([M-H]$^-$, calcd. 445.3323 for $C_{28}H_{45}O_4$). MS/MS m/z (relative intensity): 445 ([M-H]$^-$, 100%), 427 (60%), 401 (85%), 383 (40%), 223 (12%), 205 (20%), 177 (10%), 162 (18%).

Gamma-Tocopheric Acid 6

TLC $R_f$=0.62 (cyclohexane-$CH_2Cl_2$-EtOAc, 10:4:1, UV active spot); for $^1H$ and $^{13}C$ NMR spectra, see Tables 11 and 12; FTIR (cm$^{-1}$) 3314 (br), 2926, 2854, 1744, 1465, 1379, 1253, 1145, 722; HRAPCI-MS m/z: measured 465.3588 ([M-H]$^-$, calcd. 465.3585 for $C_{28}H_{49}O_5$). MS/MS m/z (relative intensity): 465 ([M-H]$^-$, 100%), 447 (50%), 421 (35%), 403 (20%), 349 (10%), 279 (18%).

Example 4

High-Throughput Screening (HTS) Method Development and Analysis of Independent Sample Set A high throughput analysis method was then developed for the six primary biomarkers discovered using the FTMS method and confirmed using the LC-MS method.

Serum samples are extracted as described for non-targeted FTMS analysis. The ethyl acetate organic fraction is used for the analysis of each sample. 15 uL of internal standard is added (1 ng/mL of (24-$^{13}C$)-Cholic Acid in methanol) to each sample aliquot of 120 uL ethyl acetate fraction for a total volume of 135 uL. The autosampler injects 100 uL of the sample by flow-injection analysis into the 4000QTRAP. The carrier solvent is 90% methanol:10% ethyl acetate, with a flow rate of 360 uL/min into the APCI source.

Figure 26:
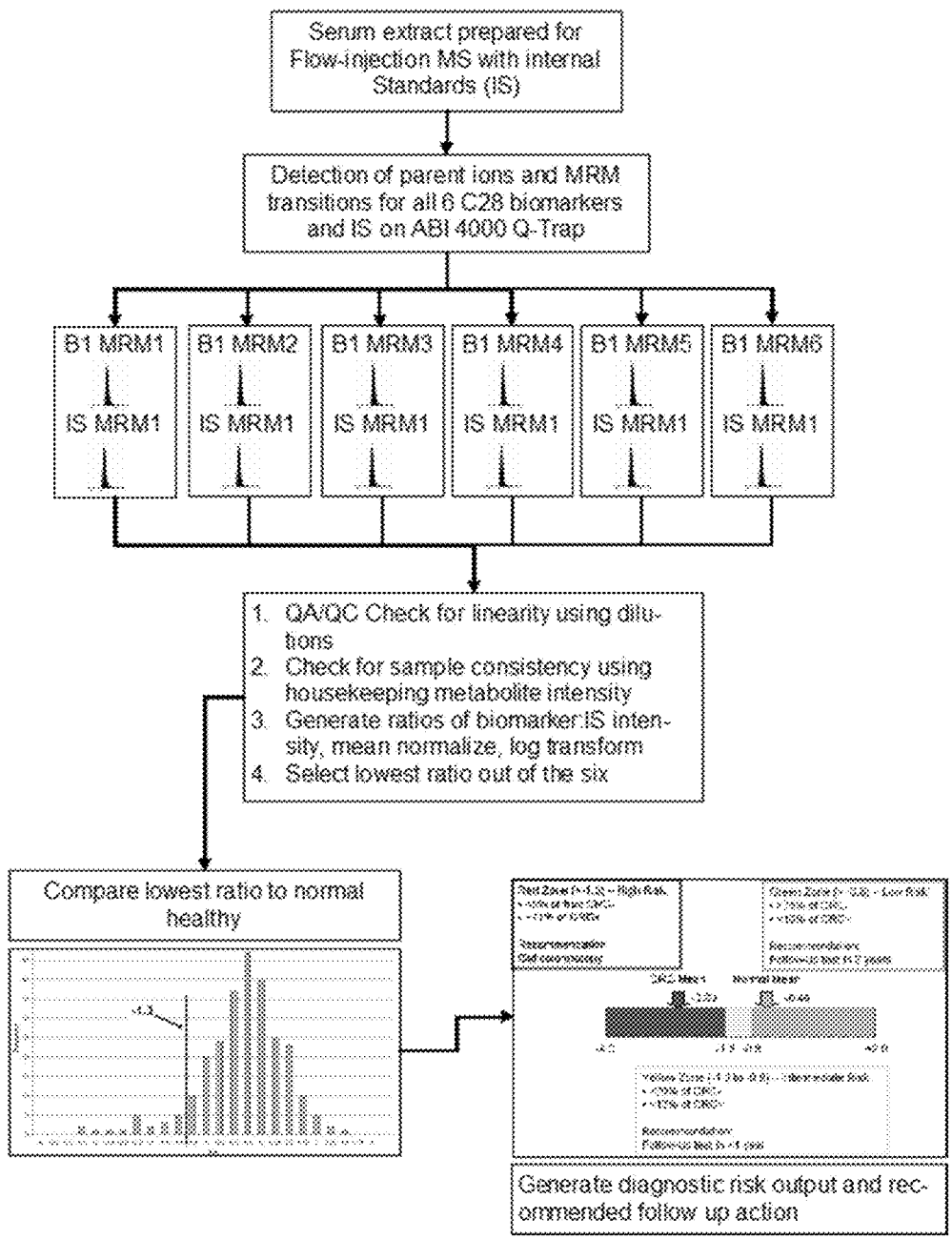
FIG. 26 shows a summary of the MS/MS high throughput screening method.
Figures 27A, 27B:
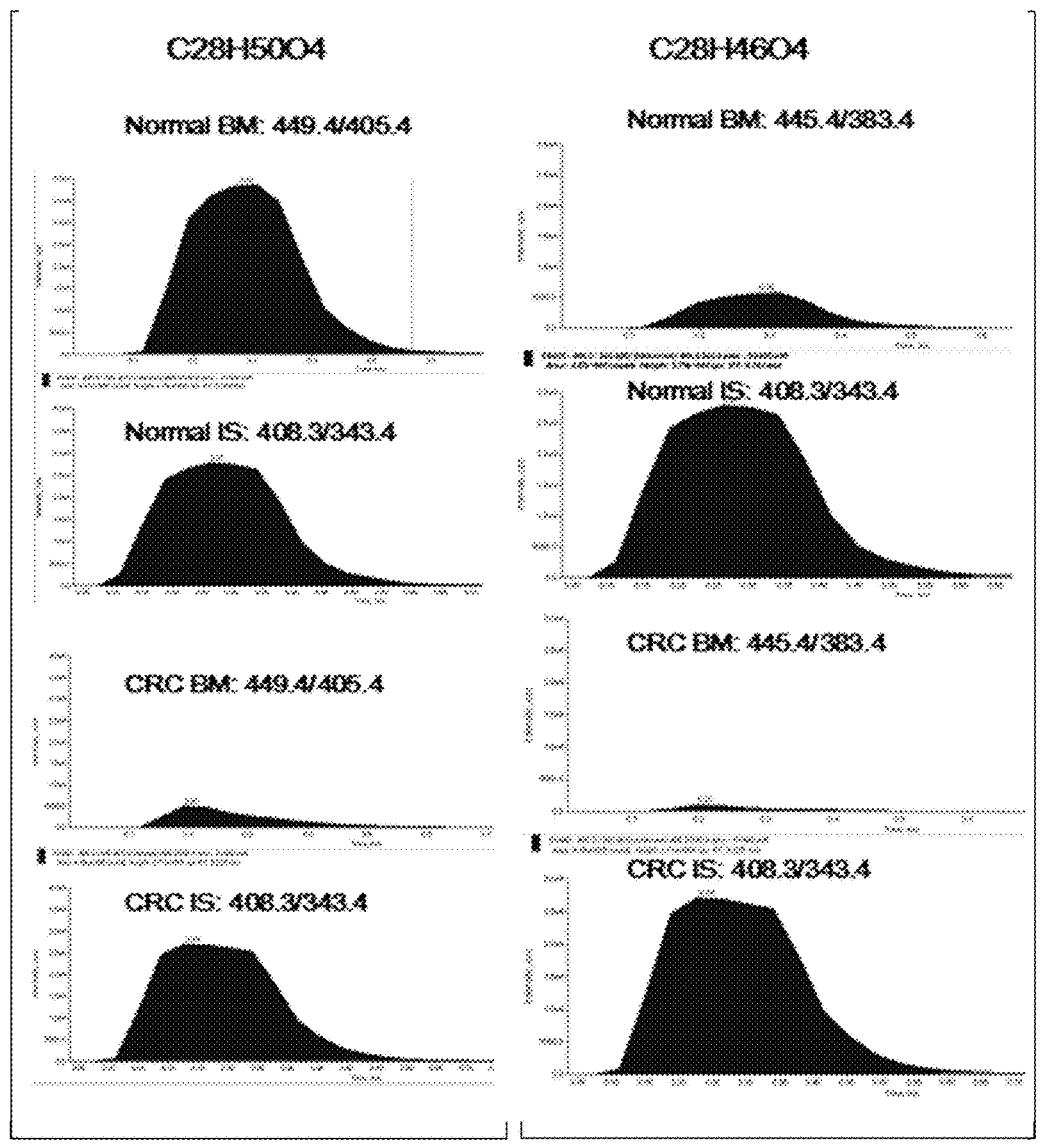
Figures 27E, 27F:
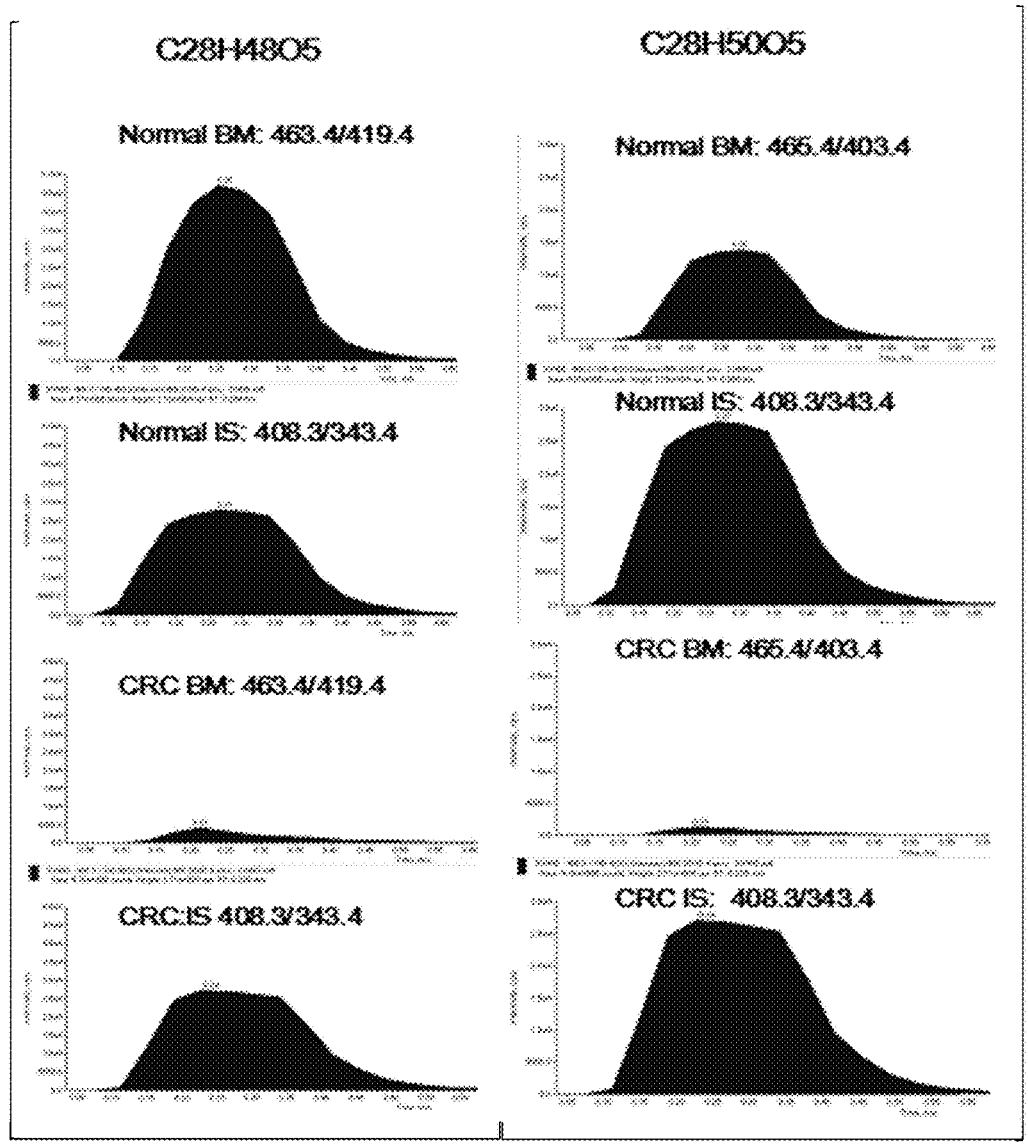
Figure 27G:
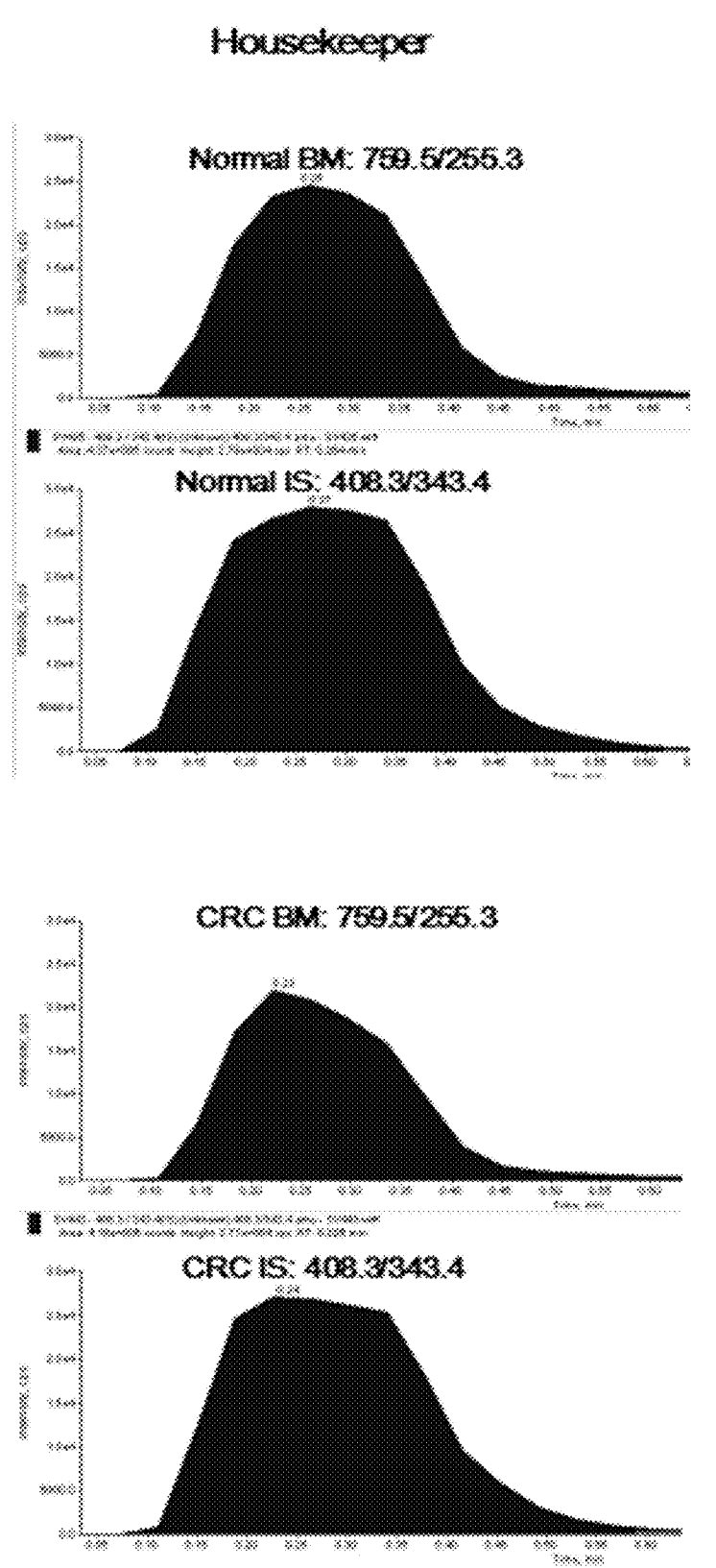

The MS/MS HTS method was developed on a quadrupole linear ion trap ABI 4000QTrap mass spectrometer equipped with a TurboV™ source with an APCI probe. The source gas parameters were as follows: CUR: 10.0, CAD: 6, NC: −3.0, TEM: 400, GS1: 15, interface heater on. "Compound" settings were as follows: entrance potential (EP): −10, and collision cell exit potential (CXP): −20.0. The method is based on the multiple reaction monitoring (MRM) of one parent ion transition for each metabolite, one transition for the endogenous housekeeper and a single transition for the internal standard. Each of the transitions is monitored for 250 ms for a total cycle time of 2.3 seconds. The total acquisition time per sample is approximately 1 min. A summary of the overall method is shown in FIG. 26. Briefly, the method measures the intensities of each of the six biomarker and internal standard (IS) transitions (as shown in FIGS. 27A to 27F), as well as a "housekeeping" biomarker transition (FIG. 27G) previously determined to be endogenously present in human serum. The housekeeping biomarker is a metabolite that was identified to not change with disease state, and should be detected in any correctly prepared serum sample. The objective of the "housekeeping" biomarker is therefore to ensure that samples collected from multiple sites are compatible with the HTS test. A patient score is then generated by determining the lowest mean-normalized log(2) transformed ratio of the six measured biomarker:IS transitions per patient. This value is then compared to a distribution of scores generated from normal individuals, and a CRC risk factor is assigned accordingly. We confirmed that the ABI 4000QTrap was capable of accurately measuring the transition peak areas using the method described above by plotting the peak area ratios of the biomarker transitions versus the internal standard transitions for each of the six biomarkers as well as the housekeeping metabolite (FIG. 26). In addition, the HTS method also incorporates a series of dilutions of reference serum material, which allows for the determination and assurance of instrument linearity. If the housekeeping metabolite is not detected, or the calibration curve has a $R^2$ value >0.98, then the sample run is considered a failure and the sample needs to be rerun.

Figure 28:
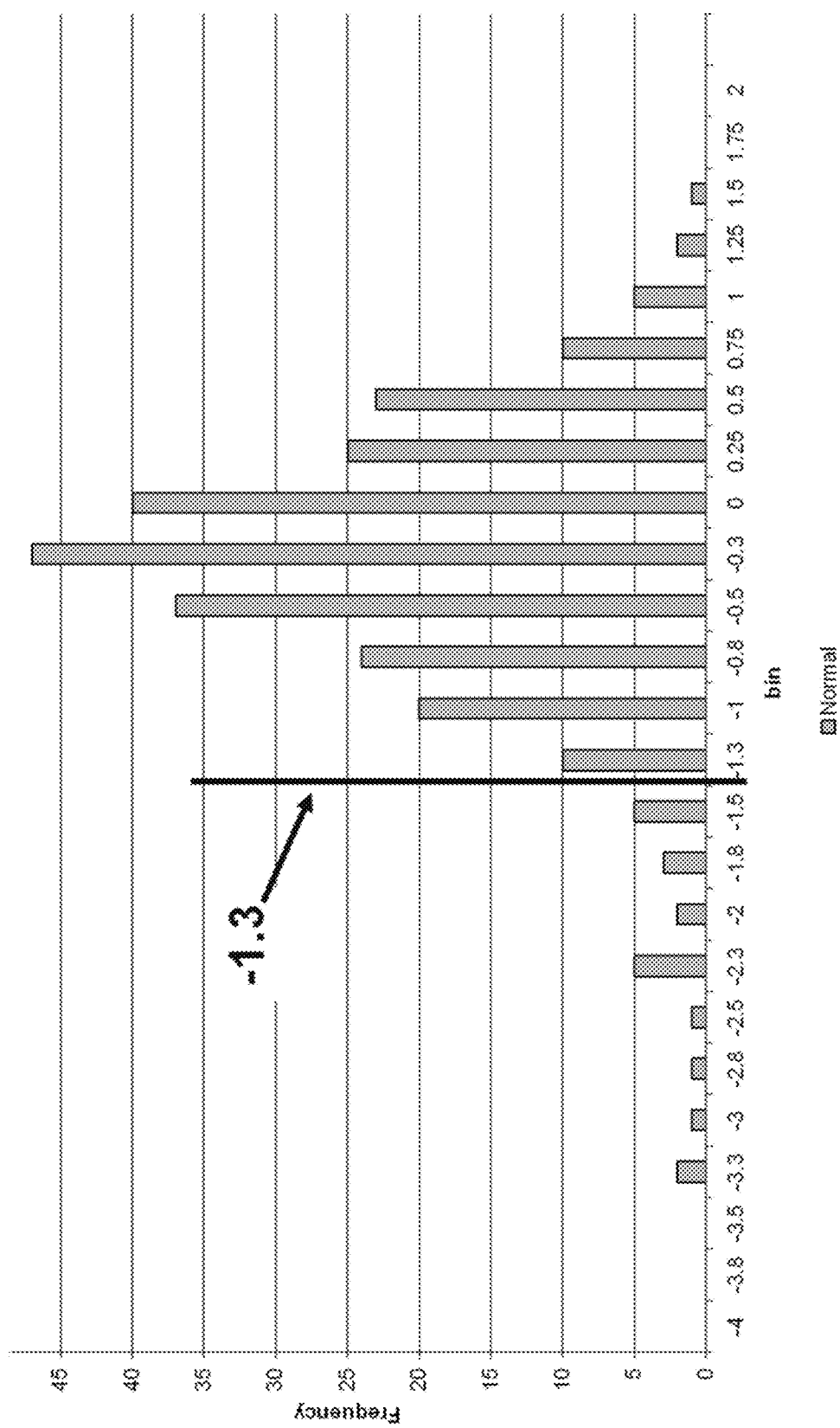
FIG. 28 shows the normal population distribution based on the final HTS output of 288 disease-free individuals. The −1.3 indicates the cutoff value selected as the point below which a person would be considered high risk for CRC (see FIG. 29).
Figure 29:
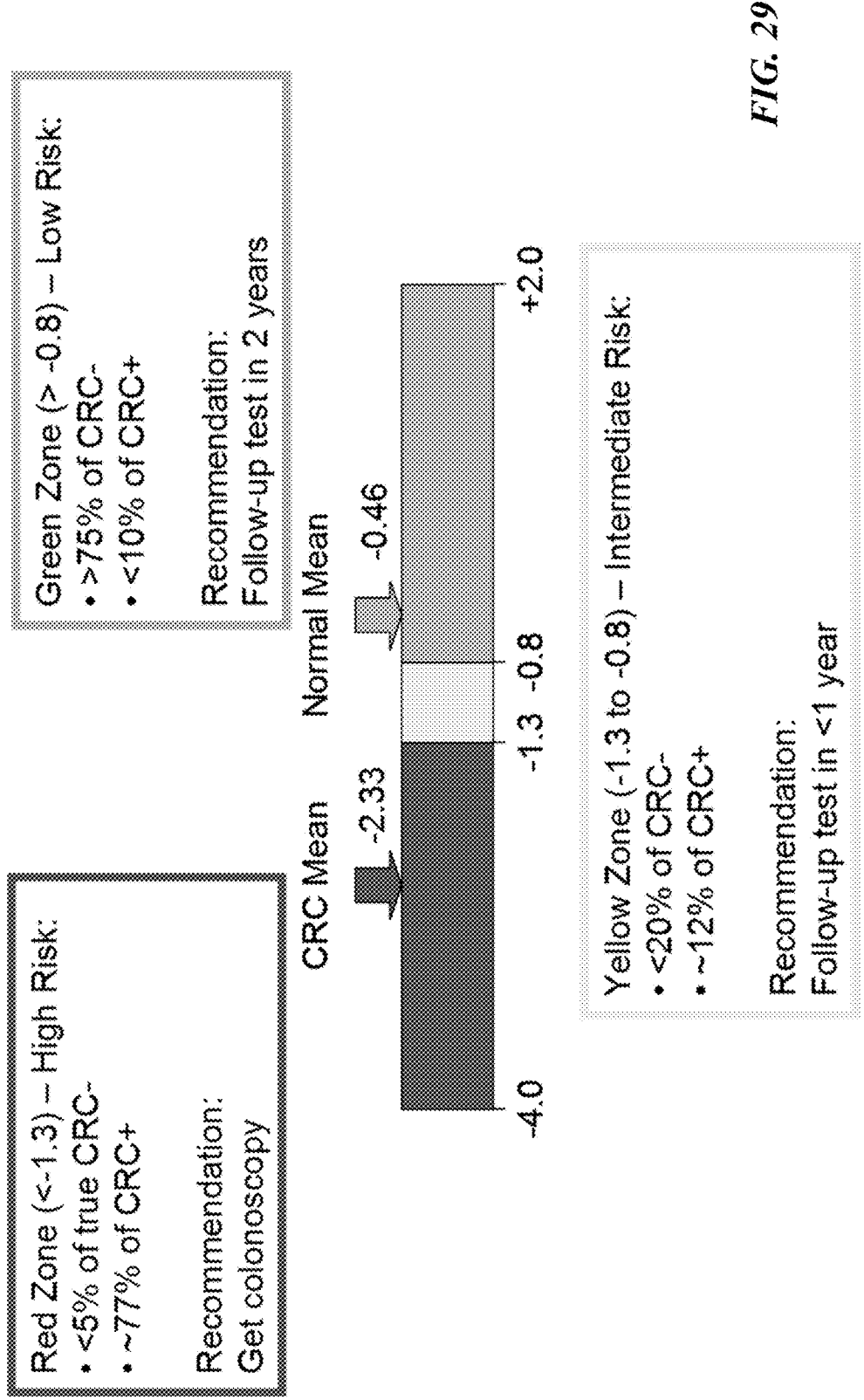
FIG. 29 shows the HTS diagnostic output. Cutoff ratios based on the distribution of normal subjects, as shown in FIG. 28, were selected as to achieve a specificity of 90.5%. This means that patient scores between −4 and −1.3 are high risk for CRC, scores between −1.3 and −0.8 are medium risk, and scores greater than −0.8 are low risk. The recommended courses of actions are shown.

To validate the initial discovery that said vitamin E-like molecules are associated with CRC, an independent set of samples comprising 186 CRC, 288 normals, 24 prostate cancer, 25 ovarian cancer, 30 renal cell carcinoma, 25 lung cancer and 20 breast cancer samples were analyzed using the HTS method described above. The results of this analysis are summarized in Tables 13A, which shows that the sensitivity of the method for CRC is approximately 78% when a cutoff ratio of −1.3 is used to determine who should be considered at high risk for the presence of CRC (see normal distribution in FIG. 28 and diagnostic output in FIG. 29). This result irrefutably verifies the decreased levels of these novel vitamin E-like molecules with the presence of colon cancer. However, here it was also determined that the cross-cancer comparison showed a sensitivity of 70% among the ovarian cancers, and 36 to 40% sensitivity for renal cell and lung cancer, respectively. These sensitivity values were selected based upon an 89% specificity cutoff for CRC (this equates to an approximate 5% false-positive rate, since the normal distribution, as shown in FIG. 28, was based upon individuals who were not confirmed to be disease-free via colonoscopy. It has been previously reported that up to 10% of the average to low-risk population is positive for high-grade dysplasia upon endoscopic examination, which were not accounted for in our distribution [52]. Although the non-CRC cancer sets were relatively small in numbers, the overlap of the test results with ovarian cancer is significant and therefore diagnosis of ovarian cancer was included in the claims. Ultimately, larger populations of non-CRC cancers will need to be tested to confirm these results.

We also used randomly selected subsets of normal and CRC-positive individuals to check for bias due to age, ethnicity, BMI and gender, and observed no significant differences in the levels of said biomarkers within any of these variable classes (Table 13B). In addition, we observed no bias towards patients grouped into either stage I/II or III/W (TNM) for CRC or to the presence or absence of polyps (Table 13B).

Example 5

Biological Interpretation of Metabolic Pathways Perturbed in CRC and OC

Based on the structural elucidation of the six biomarkers, and further investigation of the FTMS data, additional insights related to free radical formation and CRC were hypothesized.

Further investigation into putative tocopherol and tocotrienal metabolites revealed that both alpha and gamma-tocopherol concentrations in serum were observed to be significantly decreased in the CRC patient population (see FIG. 11). We calculated the alpha/gamma-tocopherol ratio to be 6.3, which is consistent with previously reported literature values. Particularly revealing was the observation that although serum alpha-tocopherol intensities were observed to be significantly higher than those of gamma, six metabolites with molecular formulas corresponding to omega-oxidized gamma-tocopherol/tocotrienol metabolites, which have never been reported in the literature, were observed in both the normals and in the CRC patients, whereas no omega-oxidized alpha-tocopherol metabolites were observed. These findings are consistent with the recent findings of Sontag and Parker [53], in which it was shown that the formation of omega COOH was over 50× greater for gamma-tocopherol than alpha-tocopherol in human hepatic HepG2 cells. This omega carboxylation event and subsequent metabolism of tocopherols to various hydroxychromanols has also been observed for tocotrienols [17]. It is believed that the reason that these metabolites were not discovered by Sontag and Parker [53] or by Birringer et al. [17] is that the omega-oxidation mechanisms described by these scientists were performed on non-modified alpha- and gamma-tocopherol/tocotrienol metabolites. Our results indicate that the omega-oxidation occurs either after gamma-tocopherol/tocotrienol has reacted with free radicals, presumably in colon/ovarian epithelial cells, or simultaneously in colon/ovarian epithelial cells.

A number of other metabolites that were observed as decreasing in CRC had molecular formulas similar to those putatively identified as gamma-tocopherol or gamma-tocotrienol-related. These metabolites fell into three broad categories based on the number of carbon molecules, specifically whether they had 30, 32, or 36 carbons (FIG. 11). It was subsequently hypothesized that these metabolites are derived from reactions between gamma-tocopherol and per-oxy radicals from linolenic, linoleic, and oleic acid lipid residues (described below). These metabolic derivatives of gamma-tocopherol/tocotrienol undergo subsequent omega oxidation via P450 during first pass metabolism in the liver.

Figure 36A:
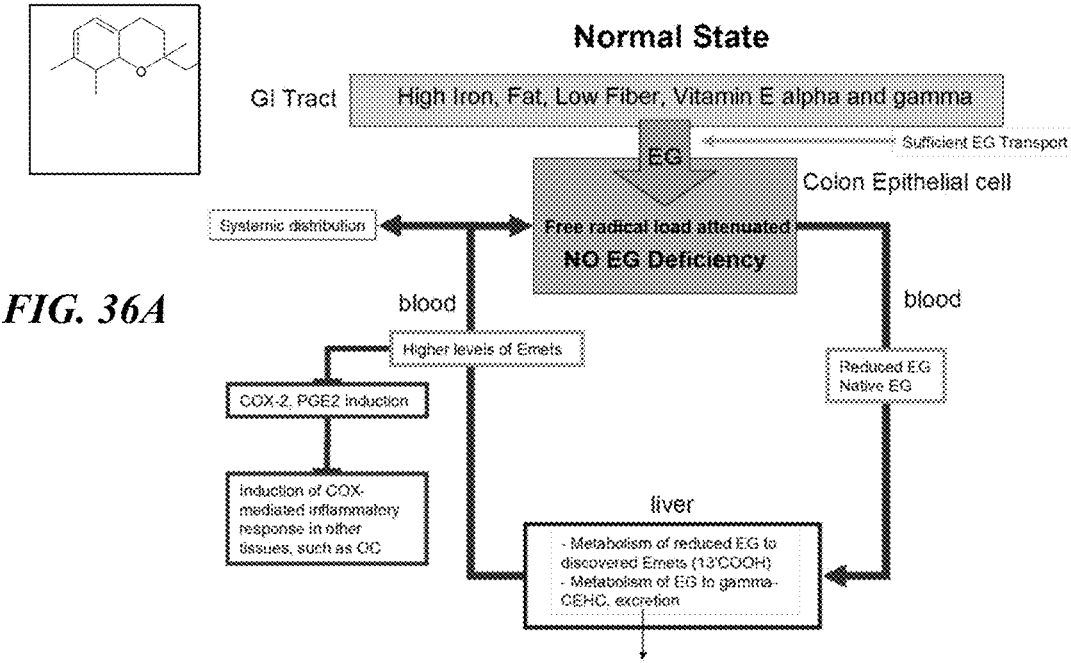
FIGS. 36A-36B show a hypothesis for the role of vitamin E and related metabolites in a normal state (FIG. 36A) and in CRC and OC (FIG. 36B).
Figure 36B:
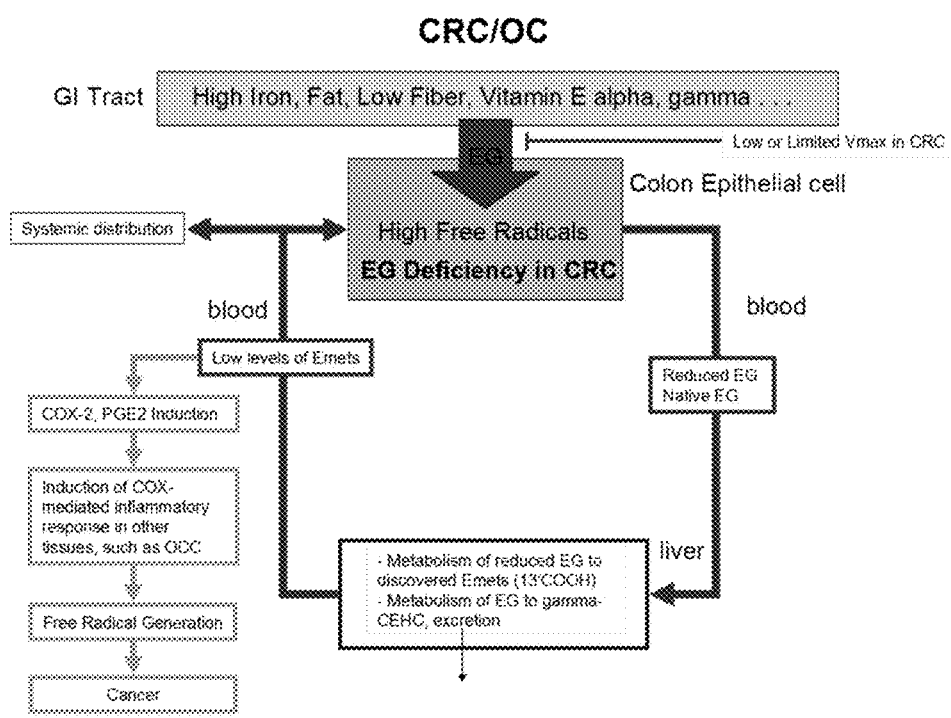

Not wishing to be bound by any particular theory, the present invention discloses a hypothesis (FIG. 36) implicating the role of vitamin E and related metabolites in the establishment and progression of CRC and OC by contemplating that the decreased levels of specific fatty acids, vitamin E isoforms, and related metabolites are not the result of a simple dietary deficiency, but rather an impairment in the colonic epithelial uptake of vitamin E and related molecules. This impairment represents a rate-limiting step for the sufficient provision of antioxidant capacity under normal or elevated oxidative stress loads. In this model, the initiating event for the development of CRC or OC is a lack of vitamin E gamma in colonic epithelial cells. Assuming an equal diet in two individuals, the person with attenuated vitamin E transport into colonic epithelia cells will have elevated free radicals. This then becomes directly proportional to the decreased serum vitamin E metabolites as described in this application. However, the hypothesis also contemplates that the resulting reduced levels of omega-COOH metabolites in the serum will have a negative inhibition effect on the prostaglandin biosynthetic pathway, due to a decreased competitive inhibitory effect on arachidonic acid, as mentioned previously in this application. We hypothesize that the resulting activation of the prostaglandin pathway is implicated in the development of other cancers, particularly ovarian, of epithelial origin. We also contemplate the further activation of the COX pathway in CRC via this mechanism, which may explain the well-established role of non-steroidal anti-inflammatory drugs (NSAIDS) as preventive agents in CRC and other cancers.

These findings are significant regarding treatment strategies of CRC and OC. In both of these diseases, inflammation is a risk factor. Gamma-tocopherol and gamma-carboxyethyl hydroxychromanol (CEHC) has been shown to decrease arachadonic mediated inflammation. The delay in activity of gamma-tocopherol indicates that gamma-tocopherol may be a precursor to the actual biologically active molecule. The discovery of multiple omega COOH gamma-tocopherol/tocotrienol metabolites suggest that these are endogenous anti-inflammatory agents and that a decrease in these metabolites may result in or be indicative of inflammation associated with CRC and OC.

Free radicals have long been thought to play a role in the etiology of colon cancer [36], [54], [55]. In this application, we present for the first time an integrated hypothesis that indicates that CRC is associated with chronic hyperoxidative stress and that gamma-tocopherol has unique anti-oxidant properties that are important for maintaining a healthy oxidative state in colon and ovarian epithelial cells. Although [56] mention the anti-oxidant properties of gamma-tocopherol, these properties are assumed to be equivalent to those of alpha-tocopherol. The present invention identifies unique metabolites that indicate that gamma-tocopherol/trienol or related metabolites may have unique lipid radical scavenging mechanisms. The high degree of selectivity of these findings to CRC and OC versus other cancers (Table 13)—in combination with previous reports showing a preferential uptake of gamma-tocopherol into colon epithelial cells, higher concentrations of gamma-tocopherol versus alpha-tocopherol in colon epithelial cells, increased bioactivity of trienols versus tocopherols, and an increased turn-over of gamma-tocopherol versus alpha-tocopherol—is strong evidence supporting the hypothesis that gamma-tocopherol/trienol-related processes are selectively involved in epithelial cell homeostasis.

It has been well established that antioxidants are consumed over the course of their function and that this function operates in real time; that is, excess antioxidant capacity on one day does not make up for deficient antioxidant capacity on another day. Apart from relatively minor recycling mechanisms, antioxidants have a limited capacity and shelf life and, once they are used up, oxidation reactions proceed unchecked. For this reason, the selection of antioxidant molecules that are capable of neutralizing multiple free radical molecules would be biologically favored. A mechanism whereby a single gamma-tocopherol/tocotrienol molecule can neutralize up to six free radical molecules is proposed and supported by the analytical data and previous literature surrounding free radical propagation.

Figure 30A:
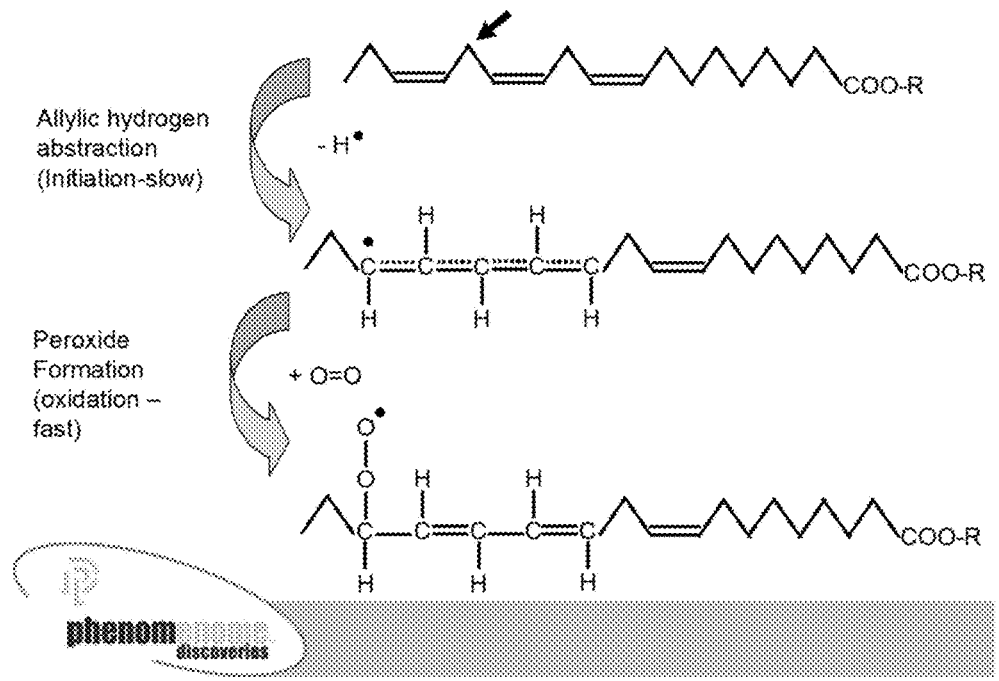
FIGS. 30A-30D show the Gamma-tocopherol/tocotrienol neutralization of lipid peroxidation. The figures show the auto-oxidation of an unsaturated fatty acid (FIG. 30A), the stabilization of peroxyl radical by gamma-tocopherol (FIG. 30B), the reaction with a peroxly radical by gamma-tocopherol radical (FIG. 30C) and the two semi-stable peroxides formed by gamma-tocopherol (FIG. 30D).

The process of lipid oxidation has been extensively studied. FIG. 30 illustrates the process of auto-oxidation of an unsaturated fatty acid (linolenic acid is used as an example). Briefly, a hydrogen radical is abstracted from a hydrocarbon molecule (FIG. 30A). This abstraction, mediated by light, heat, irradiation, metal ions, or radicals, is heavily favored in unsaturated hydrocarbons versus saturated hydrocarbons. In biological systems the formation of peroxide is the initiating step (FIG. 30A). The peroxide radical can then be either a) stabilized by gamma-tocopherol-hydroxide (FIG. 30B) or b) it can react with a gamma-tocopherol peroxide radical (FIG. 30C), in both cases forming semi-stable peroxides. The two peroxides are then converted to a hydroxide radical through the iron-catalyzed Fenton reaction [36] or in an iron-independent fashion through nitric oxide [57], [58]. Although gamma-tocopherol has been shown to be superior to alpha-tocopherol in detoxifying nitrogen dioxide in vitro [59], the in vivo study of Stone et al [60] clearly demonstrated that in rats fed either a high or low gamma-/alpha-tocopherol ratio diet, ratios of ~2:1 and 1:18, respectively, with either the recommended daily amount of iron or an eight-fold enriched diet, the increased iron was observed to significantly decrease gamma-tocopherol levels in colonocytes (32%) and plasma (18%) and alpha-tocopherol levels in colonocytes (22%). The increased iron had no effect on either alpha- or gamma-tocopherol concentrations in either the liver or feces. The iron concentration in the gastrointestinal tract is substantially higher in the colon relative to the small intestine. It has been estimated that iron concentrations in the colon are greater than 10 times those found in other tissues [36]. Therefore, free radical formation in the colon is most likely an iron-catalyzed event.

The hydroxyl radical abstracts a hydrogen radical to form a stable molecule of water and leaves behind a lipid radical. All tocopherols and tocotrienols can neutralize these hydroxyl radicals, thereby preventing lipid free radical formation. However, once a lipid radical is formed, the activity of an antioxidant is related to its ability to be co-localized with the lipid radical. It has been shown that the vitamin E isoforms contain the optimal phytyl side chain length for incorporation into lipid membranes, making these molecules ideal for scavenging lipid radicals from membranes.

Figure 30B:
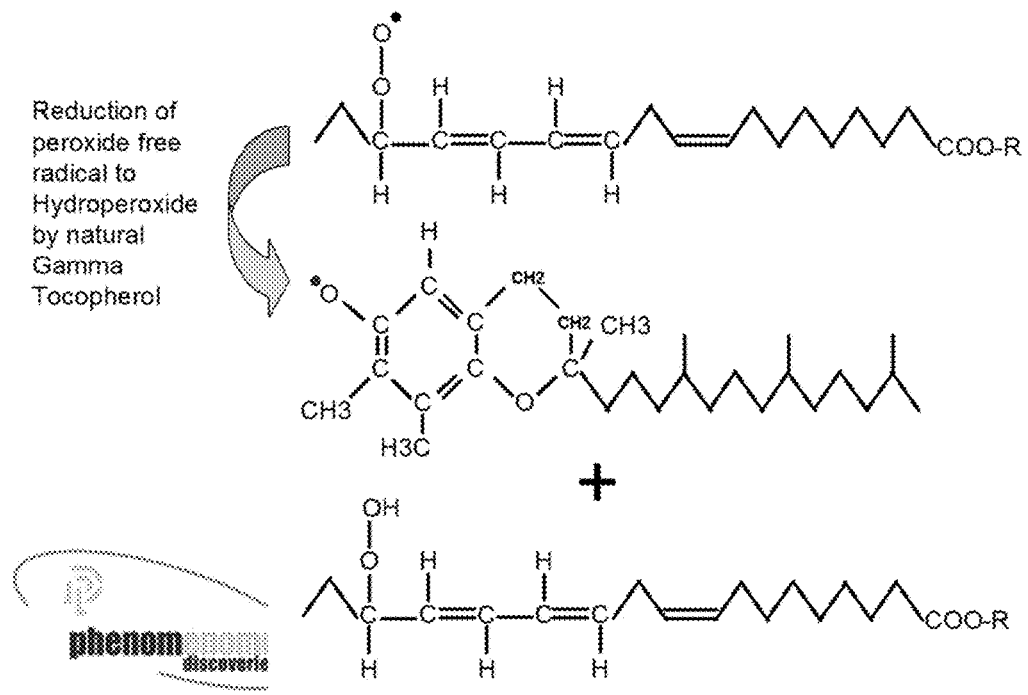
Figure 30C:
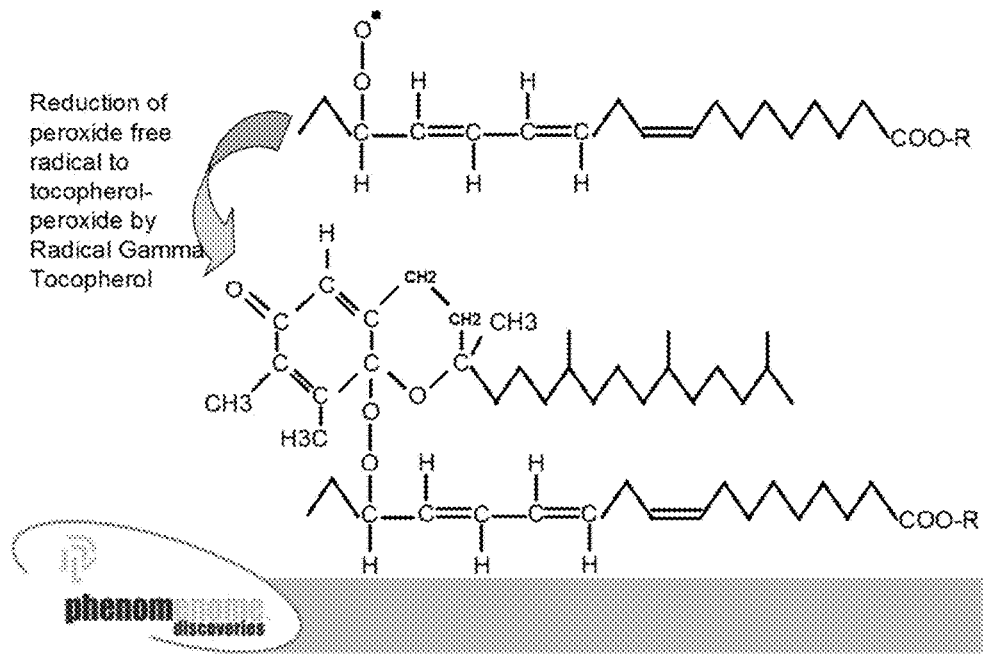
Figure 30D:
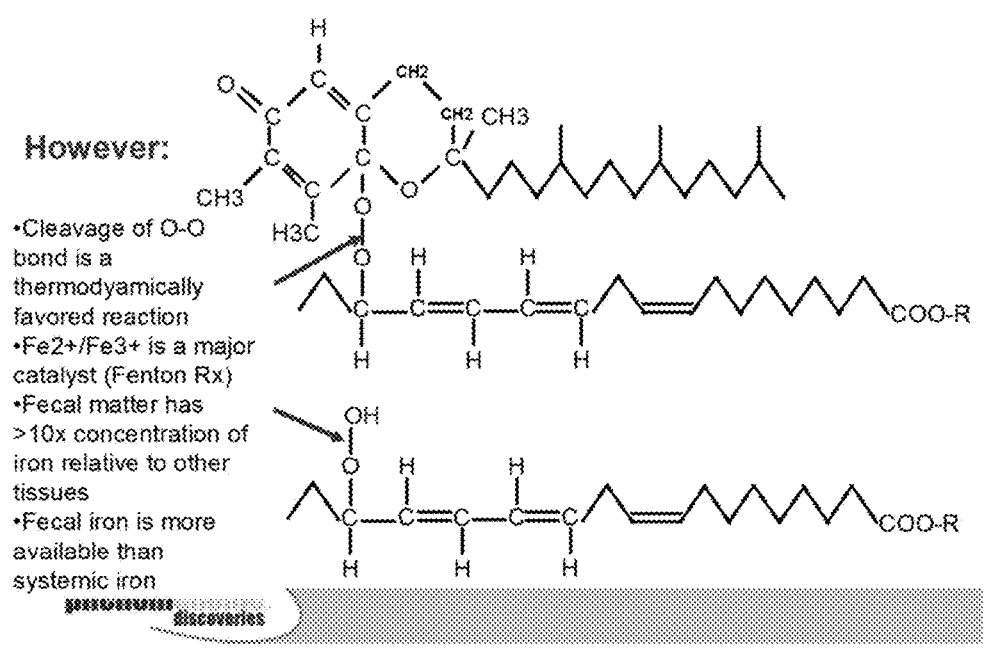

Lipid free radicals that are not scavenged readily react with oxygen to form a lipid peroxide radical (FIG. 30A). Tocopherols/tocotrienols can donate a hydrogen radical to a lipid peroxide, resulting in the formation of a tocopherol/tocotrienol radical that is stabilized by the chromanin ring structure and a resulting lipid hydroperoxide (FIG. 30B). Under normal conditions, free radical propagation is arrested at this step. The tocopherol/tocotrienol radical is capable of reacting with a second lipid peroxide radical to form a tocopherol/tocotrienol peroxide, which is an even electron molecule (FIG. 30C). Although hydro/alkyl peroxide molecules are not free radicals, the O—O bond is high energy, the breakdown of which is energetically favored (FIG. 30D). The two most potent catalysts known to facilitate the breakdown of hydroperoxides are copper and iron. As has been mentioned previously in this application, the large intestine is a particularly concentrated source of iron. Therefore, these hydroperoxides can be broken down into a hydroxyl radical and a lipid oxide radical, thereby restarting the free radical propagation sequence. Like a free lipid hydroperoxide, the tocopherol/tocotrienol peroxide is presumed to be sensitive to breakdown in the presence of iron or copper.

Figure 31A:
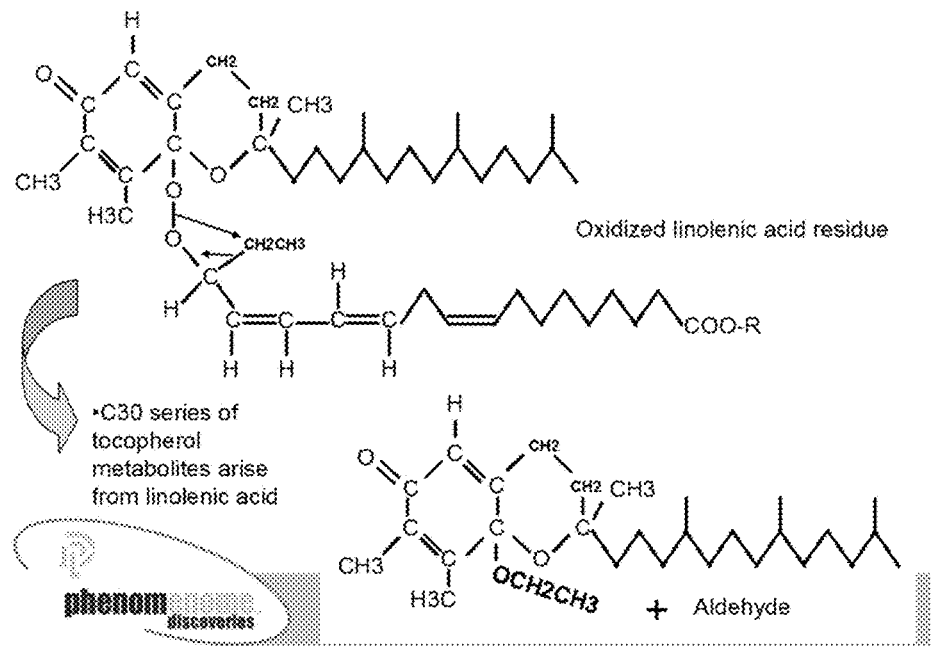
FIGS. 31A-31C show the internal degradation of gamma-tocopherol peroxide in the presence of iron.
Figure 31B:
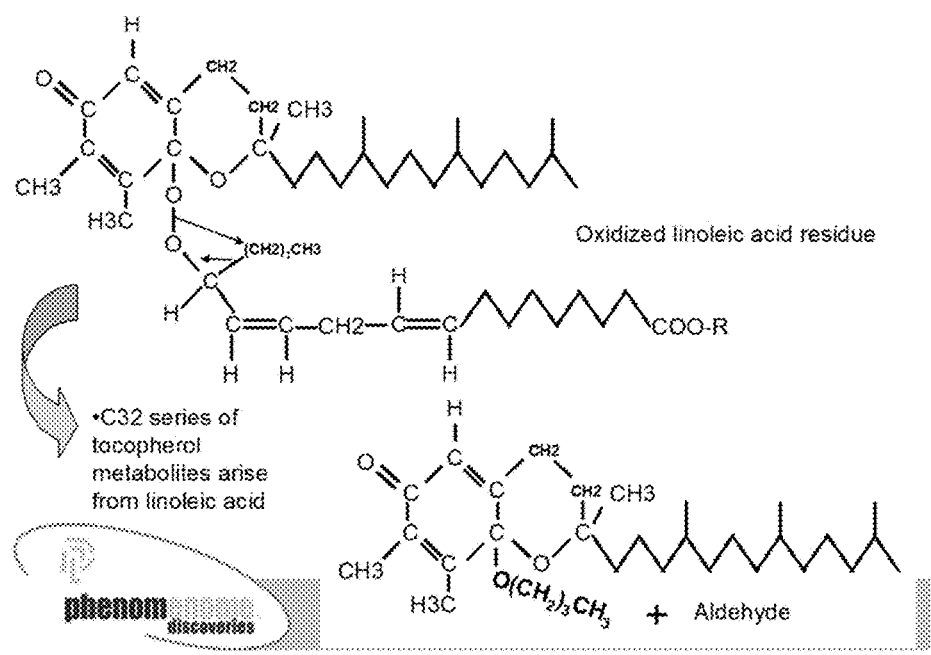
Figure 31C:
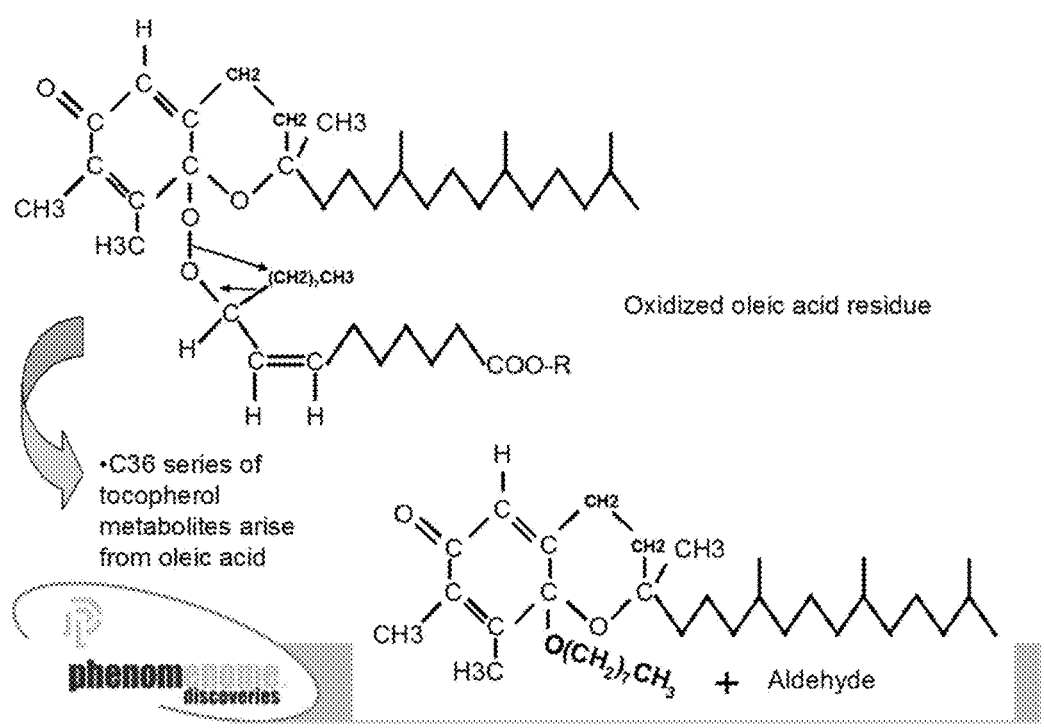
Figure 32:
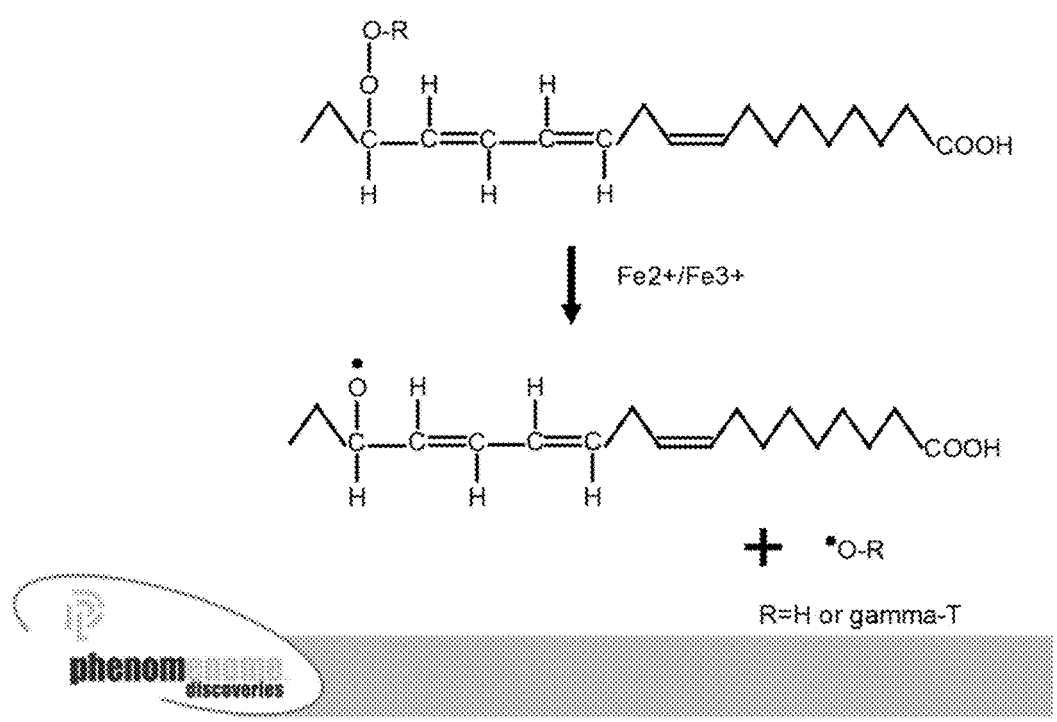
FIG. 32 shows the hydroperoxide degradation in the presence of iron.
Figure 33A:
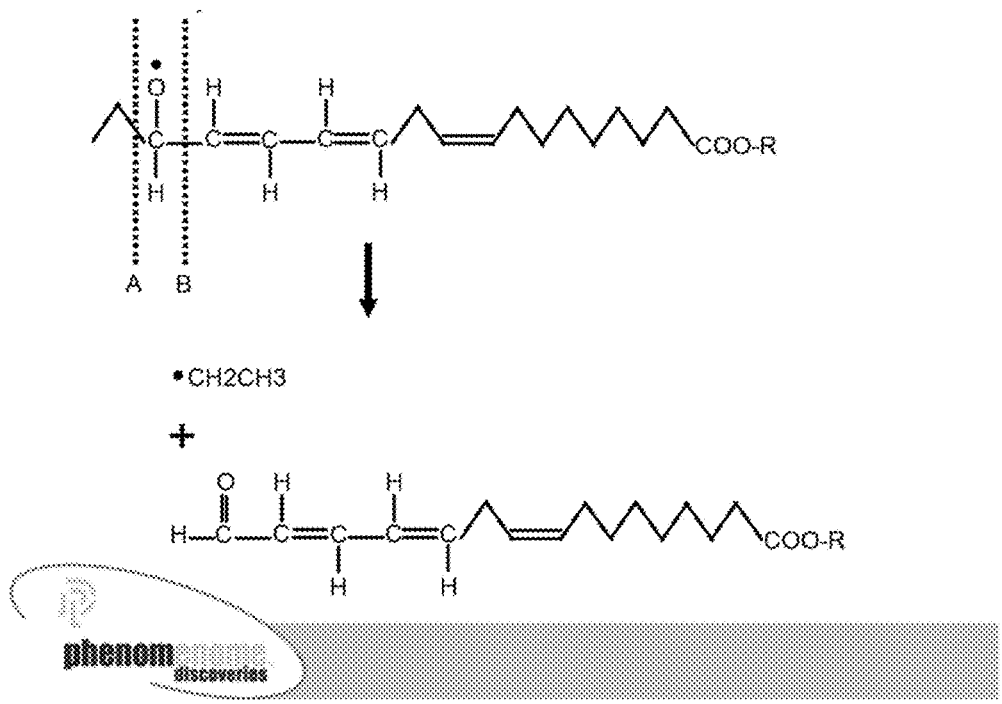
FIGS. 33A-33B show the spontaneous break down of free radicals.
Figure 33B:
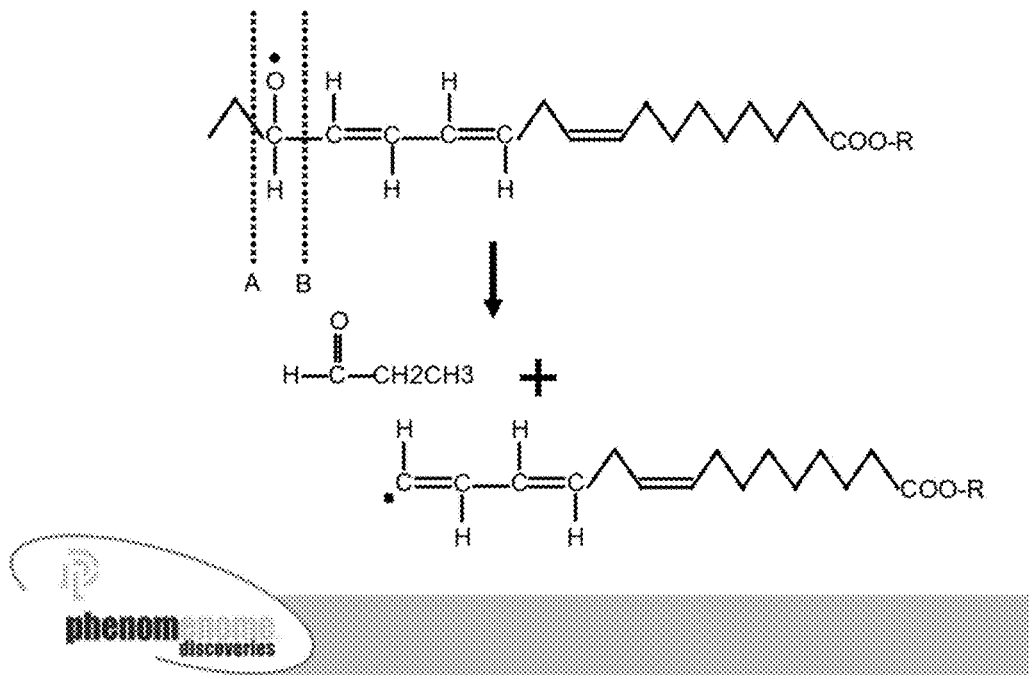
Figure 34A:
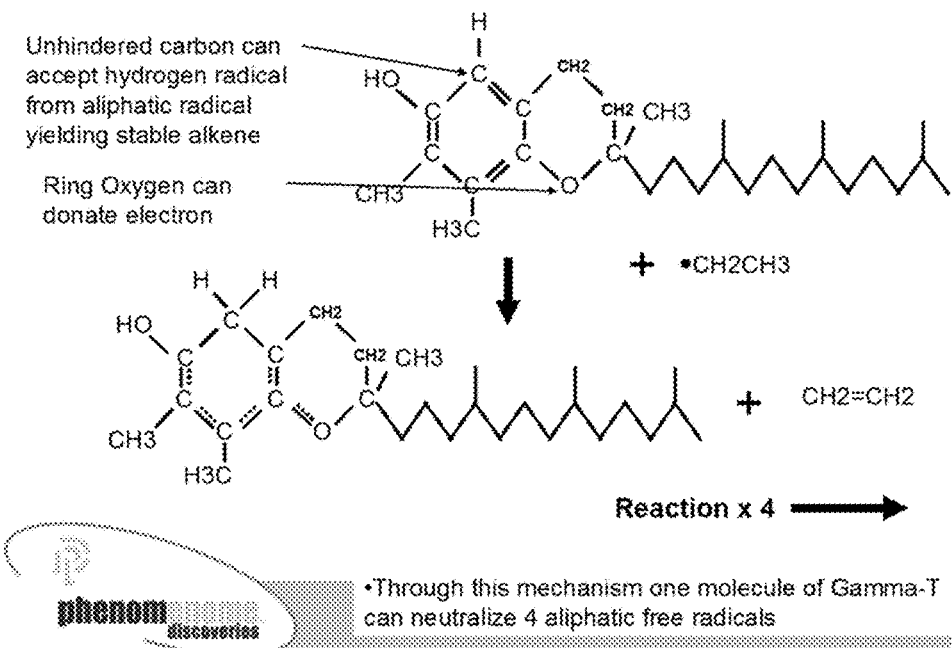
FIGS. 34A-34B show that gamma-tocopherol can neutralize the free alkane radical. The unhindered aromatic ring structure of gamma-tocopherol/tocotrienol can accept a hydrogen radical from the radical alkane, resulting in a ring-stabilized tocopherol/tocotrienol radical and a stable alkene (FIG. 34A). This hydrogen radical acceptance reaction can occur four times, reducing the ring structure to a single double bond (FIG. 34B).
Figure 34B:
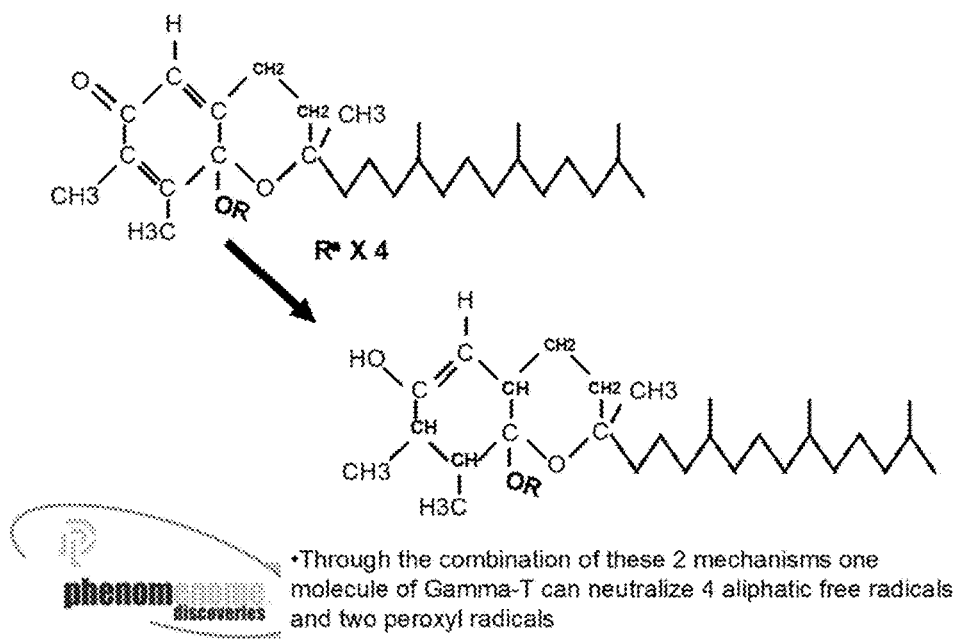

The present invention proposes a novel mechanism for the internal degradation of this peroxide into a stable tocopherol/tocotrienol alkyl ether and lipid aldehyde. The proposed reaction creates two thermodynamically stable products. It is proposed that the peroxides formed from three primary unsaturated fatty acid residues present in endogenous lipids—linolenic, linoleic, and oleic acid—are neutralized by tocopherols/tocotrienols by this mechanism (FIG. 31A to C). This mechanism appears to be selective for gamma-tocopherol, and is supported by the observation that C30, C32, and C36, byproducts of gamma-tocopherol but not alpha-tocopherol, are formed in humans. There is no such mechanism to create stable products from the degradation of the initial hydroperoxide, generated from the reaction of the neutral tocopherol/tocotrienol degraded in the presence of iron (FIGS. 32A-32B). This reaction creates a hydroxyl radical and a lipid oxide radical, and therefore needs to be neutralized by classical means. The lipid oxide radical can spontaneously degrade to an aldehyde and a radical alkane or alkene (FIG. 33). We propose an additional mechanism whereby tocopherol/tocotrienols can neutralize the resultant free radical alkane. We propose that the unhindered aromatic ring structure of gamma-tocopherol/tocotrienol can accept a hydrogen radical from the radical alkane, resulting in a ring-stabilized tocopherol/tocotrienol radical and a stable alkene (FIG. 34). Through this mechanism gamma-tocopherol/tocotrienol would be capable of neutralizing up to six alkane radicals. This hypothesis is supported by the observation of gamma-tocopherol metabolites, wherein the aromatic ring is reduced to a single double bond. It therefore appears that gamma-tocopherol can accept a maximum of four hydrogen radicals (FIGS. 34A-B). As a result of these two mechanisms, one molecule of gamma-tocopherol/tocotrienol would be capable of neutralizing six free radicals.

Figure 35:
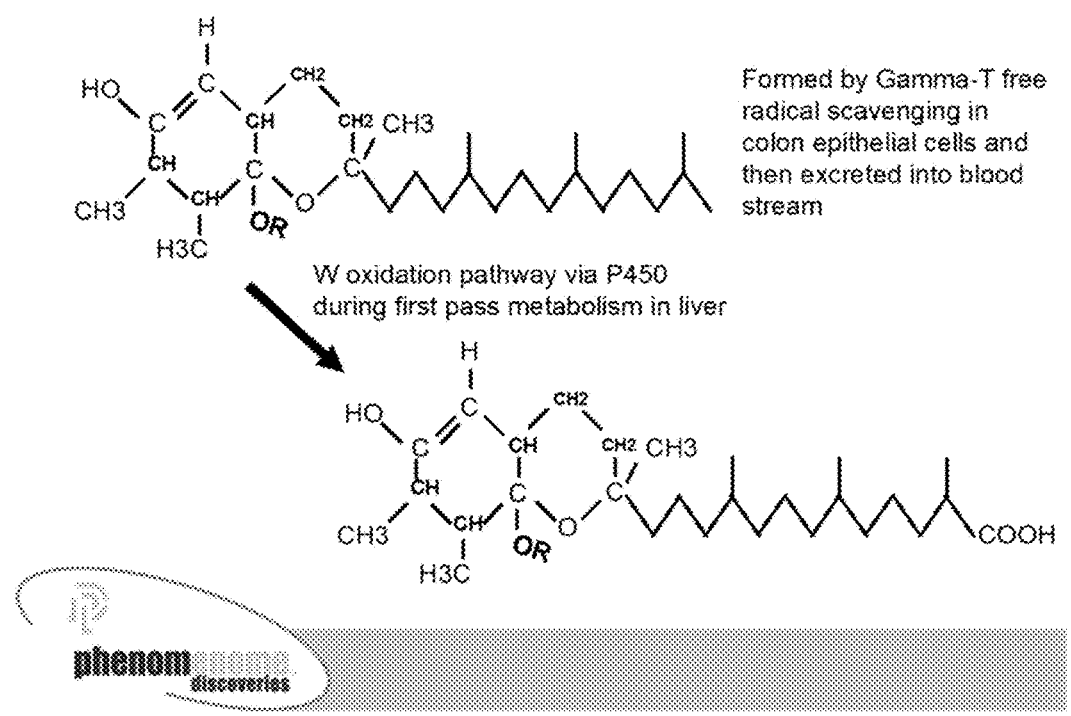
FIG. 35 shows the omega carboxylation resulting from liver P450 metabolism.

As discussed previously, the gamma-tocopherol-related metabolite that results from these proposed mechanisms undergoes w-oxidation via a P450 reaction during first pass metabolism in the liver (FIG. 35).

REFERENCES

1. Boyle, P. and M. E. Leon, *Epidemiology of colorectal cancer*. Br Med Bull, 2002. 64: p. 1-25.
2. Ahlquist, D. A., et al., *Fecal blood levels in health and disease. A study using HemoQuant*. N Engl J Med, 1985. 312(22): p. 1422-8.
3. Winawer, S., et al., *Colorectal cancer screening and surveillance: clinical guidelines and rationale-Update based on new evidence*. Gastroenterology, 2003. 124(2): p. 544-60.
4. Rex, D. K., et al., *Colorectal cancer prevention 2000: screening recommendations of the American College of Gastroenterology*. American College of Gastroenterology. Am J Gastroenterol, 2000. 95(4): p. 868-77.
5. Hixson, L. J., et al., *Prospective study of the frequency and size distribution of polyps missed by colonoscopy*. J Natl Cancer Inst, 1990. 82(22): p. 1769-72.
6. Lidofsky, S., *Detection and prevention of colon cancer: colonoscopy, virtual colonoscopy, and DNA stool tests*. Med Health R I, 2005. 88(3): p. 82-5.
7. Davies, R. J., R. Miller, and N. Coleman, *Colorectal cancer screening: prospects for molecular stool analysis*. Nat Rev Cancer, 2005. 5(3): p. 199-209.
8. *Screening for ovarian cancer: recommendation statement*. Ann Fam Med, 2004. 2(3): p. 260-2.
9. Chu, C. S. and S. C. Rubin, *Screening for ovarian cancer in the general population*. Best Pract Res Clin Obstet Gynaecol, 2005.
10. Hanna, L and M. Adams, *Prevention of ovarian cancer*. Best Pract Res Clin Obstet Gynaecol, 2005.
11. Rosenthal, A and I. Jacobs, *Familial ovarian cancer screening*. Best Pract Res Clin Obstet Gynaecol, 2005.
12. Cook, M. G. and P. McNamara, *Effect of dietary vitamin E on dimethylhydrazine-induced colonic tumors in mice*. Cancer Res, 1980. 40(4): p. 1329-31.
13. Coulter, I. D., et al., *Antioxidants vitamin C and vitamin e for the prevention and treatment of cancer*. J Gen Intern Med, 2006. 21(7): p. 735-44.
14. Theriault, A., et al., *Tocotrienol: a review of its therapeutic potential*. Clin Biochem, 1999. 32(5): p. 309-19.
15. Serbinova, E., et al., *Free radical recycling and inframembrane mobility in the antioxidant properties of alpha-tocopherol and alpha-tocotrienol*. Free Radic Biol Med, 1991. 10(5): p. 263-75.
16. Lee, B. L., A. L. New, and C. N. Ong, *Simultaneous determination of tocotrienols, tocopherols, retinol, and major carotenoids in human plasma*. Clin Chem, 2003. 49(12): p. 2056-66.
17. Birringer, M., et al., *Identities and differences in the metabolism of tocotrienols and tocopherols in HepG2 cells*. J Nutr, 2002. 132(10): p. 3113-8.
18. Bieri, J. G. and R. P. Evans, *Gamma tocopherol: metabolism, biological activity and significance in human vitamin E nutrition*. Am J Clin Nutr, 1974. 27(9): p. 980-6.
19. Traber, M. G., *Determinants of plasma vitamin E concentrations*. Free Radic Biol Med, 1994. 16(2): p. 229-39.
20. Princen, H. M., et al., *Supplementation with low doses of vitamin E protects LDL from lipid peroxidation in men and women*. Arterioscler Thromb Vasc Biol, 1995. 15(3): p. 325-33.
21. Schaffer, S., W. E. Muller, and G. P. Eckert, *Tocotrienols: constitutional effects in aging and disease*. J Nutr, 2005. 135(2): p. 151-4.
22. Winidhofer-Roob, B. M., M. A. van't Hof, and D. H. Shmerling, *Reference values for plasma concentrations of vitamin E and A and carotenoids in a Swiss population from infancy to adulthood, adjusted for seasonal influences*. Clin Chem, 1997. 43(1): p. 146-53.
23. Qureshi, A. A., et al., *Lowering of serum cholesterol in hypercholesterolemic humans by tocotrienols (palmvitee)*. Am J Clin Nutr, 1991. 53(4 Suppl): p. 1021S-1026S.
24. Qureshi, A. A., et al., *Novel tocotrienols of rice bran suppress cholesterogenesis in hereditary hypercholesterolemic swine*. J Nutr, 2001. 131(2): p. 223-30.
25. Sen, C. K., S. Khanna, and S. Roy, *Tocotrienols: Vitamin E beyond tocopherols*. Life Sci, 2006. 78(18): p. 2088-98.
26. Khanna, S, et al., *Molecular basis of vitamin E action: tocotrienol modulates 12-lipoxygenase, a key mediator of glutamate-induced neurodegeneration*. J Biol Chem, 2003. 278(44): p. 43508-15.
27. Qureshi, A. A., et al., *Synergistic effect of tocotrienol-rich fraction (TRF(25)) of rice bran and lovastatin on lipid parameters in hypercholesterolemic humans*. J Nutr Biochem, 2001. 12(6): p. 318-329.
28. Adachi, H. and N. Ishii, *Effects of tocotrienols on life span and protein carbonylation in Caenorhabditis elegans*. J Gerontol A Biol Sci Med Sci, 2000. 55(6): p. B280-5.
29. Nesaretnam, K, et al., *Effect of tocotrienols on the growth of a human breast cancer cell line in culture*. Lipids, 1995. 30(12): p. 1139-43.
30. McIntyre, B. S., et al., *Antiproliferative and apoptotic effects of tocopherols and tocotrienols on normal mouse mammary epithelial cells*. Lipids, 2000. 35(2): p. 171-80.
31. Jiang, Q. and B. N. Ames, *Gamma-tocopherol, but not alpha-tocopherol, decreases proinflammatory eicosanoids and inflammation damage in rats*. Faseb J, 2003. 17(8): p. 816-22.

32. Jiang, Q., et al., *gamma-tocopherol and its major metabolite, in contrast to alpha-tocopherol, inhibit cyclooxygenase activity in macrophages and epithelial cells*. Proc Natl Acad Sci USA, 2000. 97(21): p. 11494-9.
33. Tran, K. and A C Chan, *Comparative uptake of alpha- and gamma-tocopherol by human endothelial cells*. Lipids, 1992. 27(1): p. 38-41.
34. Nair, P. P., et al., *Uptake and distribution of carotenoids, retinol, and tocopherols in human colonic epithelial cells in vivo*. Cancer Epidemiol Biomarkers Prev, 1996. 5(11): p. 913-6.
35. Ingles, S. A., et al., *Plasma tocopherol and prevalence of colorectal adenomas in a multiethnic population*. Cancer Res, 1998. 58(4): p. 661-6.
36. Babbs, C. F., *Free radicals and the etiology of colon cancer*. Free Radic Biol Med, 1990. 8(2): p. 191-200.
37. Reboul, E., et al., *Scavenger receptor class B type I (SR-BI) is involved in vitamin E transport across the enterocyte*. J Biol Chem, 2006. 281(8): p. 4739-45.
38. Reo, N. V., *NMR-based metabolomics*. Drug Chem Toxicol, 2002. 25(4): p. 375-82.
39. Fiehn, O., et al., *Metabolite profiling for plant functional genomics*. Nat Biotechnol, 2000. 18(11): p. 1157-61.
40. Hirai, M. Y., et al., *Integration of transcriptomics and metabolomics for understanding of global responses to nutritional stresses in Arabidopsis thaliana*. Proc Natl Acad Sci USA, 2004. 101(27): p. 10205-10.
41. Roessner, U., et al., *Metabolic profiling allows comprehensive phenotyping of genetically or environmentally modified plant systems*. Plant Cell, 2001. 13(1): p. 11-29.
42. Castrillo, J. I., et al., *An optimized protocol for metabolome analysis in yeast using direct infusion electrospray mass spectrometry*. Phytochemistry, 2003. 62(6): p. 929-37.
43. Fiehn, O., *Metabolomics—the link between genotypes and phenotypes*. Plant Mol Biol, 2002. 48(1-2): p. 155-71.
44. Aharoni, A., et al., *Nontargeted metabolome analysis by use of Fourier Transform Ion Cyclotron Mass Spectrometry*. Omics, 2002. 6(3): p. 217-34.
45. Hirai, M. Y., et al., *Elucidation of gene-to-gene and metabolite-to-gene networks in arabidopsis by integration of metabolomics and transcriptomics*. J Biol Chem, 2005. 280(27): p. 25590-5.
46. Murch, S. J., et al., *A metabolomic analysis of medicinal diversity in Huang-qin (Scutellaria baicalensis Georgi) genotypes: discovery of novel compounds*. Plant Cell Rep, 2004. 23(6): p. 419-25.
47. Tohge, T., et al., *Functional genomics by integrated analysis of metabolome and transcriptome of Arabidopsis plants over-expressing an MYB transcription factor*. Plant J, 2005. 42(2): p. 218-35.
48. Tibshirani, R., et al., *Diagnosis of multiple cancer types by shrunken centroids of gene expression*. Proc Natl Acad Sci USA, 2002. 99(10): p. 6567-72.
49. Wu, B., et al., *Comparison of statistical methods for classification of ovarian cancer using mass spectrometry data*. Bioinformatics, 2003. 19(13): p. 1636-43.
50. Pearce, B. C., et al., *Hypocholesterolemic activity of synthetic and natural tocotrienols*. J Med Chem, 1992. 35(20): p. 3595-606.
51. Han, N. M., et al., *Isolation of palm tocols using supercritical fluid chromatography*. J Chromatogr Sci, 2004. 42(10): p. 536-9.
52. Collins, J. F. et al., *Accuracy of screening for fecal occult blood on a single stool sample obtained by digital rectal examination: a comparison with recommended sampling practice*. Ann Intern Med, 2005. 142(2): p. 81-5.
53. Sontag, T. J. and R. S. Parker, *Cytochrome P450 omega-hydroxylase pathway of tocopherol catabolism. Novel mechanism of regulation of vitamin E status*. J Biol Chem, 2002. 277(28): p. 25290-6.
54. Blakeborough, M. H., R. W. Owen, and R. F. Bilton, *Free radical generating mechanisms in the colon: their role in the induction and promotion of colorectal cancer?* Free Radic Res Commun, 1989. 6(6): p. 359-67.
55. Graf, E. and J. W. Eaton, *Dietary suppression of colonic cancer. Fiber or phytate?* Cancer, 1985. 56(4): p. 717-8.
56. Campbell, S., et al., *Development of gamma (gamma)-tocopherol as a colorectal cancer chemopreventive agent*. Crit Rev Oncol Hematol, 2003. 47(3): p. 249-59.
57. Rubbo, H., et al., *Nitric oxide regulation of superoxide and peroxynitrite-dependent lipid peroxidation. Formation of novel nitrogen-containing oxidized lipid derivatives*. J Biol Chem, 1994. 269(42): p. 26066-75.
58. Radi, R., et al., *Peroxynitrite-induced membrane lipid peroxidation: the cytotoxic potential of superoxide and nitric oxide*. Arch Biochem Biophys, 1991. 288(2): p. 481-7.
59. Cooney, R. V., et al., *Gamma-tocopherol detoxification of nitrogen dioxide: superiority to alpha-tocopherol*. Proc Natl Acad Sci USA, 1993. 90(5): p. 1771-5.
60. Stone, W. L., et al., *The influence of dietary iron and tocopherols on oxidative stress and ras-p21 levels in the colon*. Cancer Detect Prev, 2002. 26(1): p. 78-84.

All citations are hereby incorporated by reference.

The present invention has been described with regard to one or more embodiments. However, it will be apparent to persons skilled in the art that a number of variations and modifications can be made without departing from the scope of the invention.

TABLE 1

CRC Staging and Survival Statistics

| STAGE | TNM | GROUP | GROUP | DUKE'S | Prognosis |
|---|---|---|---|---|---|
| Stage I | T1 | N0 | M0 | Duke's A | 5 year survival >90% |
| | T2 | N0 | M0 | | |
| Stage II | T3 | N0 | M0 | Duke's B | 5 year survival 70-85% |
| | T4 | N0 | M0 | | 5 year survival 55-65% |
| Stage III | any T | N1 | M0 | Duke's C | 5 year survival 45-55% |
| | any T | N2, N3 | M0 | | 5 year survival 20-30% |
| Stage IV | any T | any N | M1 (distant) | Duke's D | 5 year survival <5% |

T = tumor;
N = node involvement;
M = metastasis

TABLE 2

Comparison of current CRC screening tests (modified from Davies et al)

| Test | Sensitivity | Specificity | Cost | Whole Colon | Non-invasive | advantages | disadvantages |
|---|---|---|---|---|---|---|---|
| Fecal occult blood test | Moderate to low | Moderate | Low | Yes | Yes | No bowel preparation, can be combined with flexible sigmoidoscopy to improve detection | Repeat samples needed, dietary and drug restrictions required |
| Digital rectal examination | Low | Low | Low | No | No | Simple to perform | Patient discomfort |
| Flexible sigmoidoscopy | Moderate to high | High | Moderate | No | No | Allows removal of precancerous lesions | Patient discomfort, bowel prepration needed, risk of bowel perforation and bleeding, trained personnel needed, data from randomized trials still pending |
| Barium enema | Moderate | Moderate to high | Moderate | Yes | No | Lower risk of bowel performation than endoscopic screening | Patient discomfort, bowel preparation needed, trained personnel needed |
| Colonoscopy | High | High | High | Yes | No | Allows removal of precancerous polyps, evidence of reduced cancer incidence after polyp removal | Patient discomfort, bowel preparation needed, risk of bowel perforation and bleeding, mortality of 1-3/10000, intravenous sedation required, highly trained personnel needed, no randomized control trials |
| Virtual Colonoscopy | High | High | High | Yes | Yes | Speed, no sedation needed, extracolonic and pelvic organs can be imaged, high patient acceptability | Patient discomfort, bowel prepatation required, high radiation dose, trained personnel needed, high inter-observer variability, limited specificity, unknown sensitivity for flat adenomas |
| Cellular markers | Moderate to high | Moderate to high | Unknown | Yes | Yes | Single stool sample adequate, no bowel preparation required, specimens transportable, potential high patient acceptability | Research stage of development, assay might be time-consuming, lack of technology for large-scale use |
| DNA markers | Moderate to low | Moderate to high | Unknown | Yes | Yes | Single stool sample adequate, no bowel preparation required, specimens transportable, potential high patient acceptability | Research stage of development, time-consuming assay, lack of large-scale technology |
| Serum Metabolite Panel* | High | High | Low | Yes | Yes | Single serum sample required, specimens transportable, high patient acceptability, portability and potentially simple integration of assay into conventional clinical chemistry labs, quick turnaround time, very low cost, potential detection of risk prior to full CRC onset | Validation trials still in progress, lack of appropriate clinical action for high-risk individuals not showing detectable adenomas or CRC. |

*As described in this application

TABLE 3

Accurate neutral mass features differing between CRC and normal serum ($p < 0.05$, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 450.3726 | 1204 | 2.367 | 0.145 | 0.335 | 0.149 | 7.072 | 2.31E−24 |
| 466.3661 | 1204 | 2.338 | 0.157 | 0.386 | 0.136 | 6.052 | 8.16E−23 |
| 499.9401 | 1202 | 2.454 | 0.196 | 0.254 | 0.144 | 9.673 | 2.16E−21 |
| 468.384 | 1204 | 3.078 | 0.139 | 1.062 | 0.201 | 2.899 | 8.85E−21 |
| 592.4711 | 1204 | 2.769 | 0.159 | 0.794 | 0.189 | 3.487 | 1.54E−19 |

TABLE 3-continued

Accurate neutral mass features differing between CRC and normal serum (p < 0.05, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 538.4259 | 1204 | 2.843 | 0.131 | 1.000 | 0.199 | 2.842 | 3.04E-19 |
| 502.405 | 1204 | 2.060 | 0.115 | 0.553 | 0.171 | 3.729 | 6.10E-18 |
| 594.4851 | 1204 | 3.471 | 0.169 | 1.406 | 0.225 | 2.469 | 7.92E-18 |
| 464.3522 | 1204 | 2.122 | 0.142 | 0.528 | 0.160 | 4.019 | 9.72E-18 |
| 446.3406 | 1204 | 3.044 | 0.141 | 1.137 | 0.226 | 2.678 | 1.19E-17 |
| 594.4876 | 1202 | 2.602 | 0.175 | 0.814 | 0.166 | 3.196 | 2.89E-17 |
| 777.5285 | 1201 | 3.664 | 0.087 | 2.750 | 0.092 | 1.332 | 8.33E-17 |
| 492.3829 | 1204 | 1.937 | 0.159 | 0.399 | 0.141 | 4.850 | 1.46E-16 |
| 504.4189 | 1204 | 1.835 | 0.142 | 0.424 | 0.146 | 4.328 | 5.17E-16 |
| 536.4108 | 1204 | 2.371 | 0.119 | 0.894 | 0.191 | 2.652 | 9.64E-16 |
| 801.5542 | 1202 | 3.194 | 0.119 | 2.084 | 0.108 | 1.532 | 1.21E-15 |
| 795.5182 | 1101 | 2.286 | 0.130 | 1.025 | 0.133 | 2.231 | 1.89E-15 |
| 616.4672 | 1201 | 1.818 | 0.169 | 0.361 | 0.123 | 5.036 | 2.01E-15 |
| 595.4896 | 1204 | 2.249 | 0.191 | 0.534 | 0.162 | 4.209 | 2.62E-15 |
| 783.5777 | 1101 | 5.534 | 0.096 | 4.543 | 0.119 | 1.218 | 5.59E-15 |
| 808.5794 | 1101 | 4.104 | 0.077 | 3.296 | 0.100 | 1.245 | 7.83E-15 |
| 802.5576 | 1202 | 1.954 | 0.113 | 0.812 | 0.140 | 2.407 | 1.49E-14 |
| 576.4766 | 1202 | 1.763 | 0.154 | 0.428 | 0.133 | 4.117 | 1.55E-14 |
| 494.3977 | 1204 | 2.110 | 0.168 | 0.630 | 0.152 | 3.348 | 1.70E-14 |
| 577.4798 | 1204 | 2.055 | 0.169 | 0.519 | 0.167 | 3.960 | 1.79E-14 |
| 580.5092 | 1204 | 1.593 | 0.158 | 0.277 | 0.120 | 5.758 | 1.81E-14 |
| 520.3353 | 1101 | 1.969 | 0.103 | 0.897 | 0.137 | 2.195 | 2.03E-14 |
| 784.5809 | 1101 | 4.467 | 0.099 | 3.480 | 0.122 | 1.284 | 2.04E-14 |
| 520.4144 | 1204 | 2.424 | 0.124 | 1.065 | 0.183 | 2.276 | 2.49E-14 |
| 755.5466 | 1101 | 2.161 | 0.115 | 1.175 | 0.099 | 1.838 | 2.81E-14 |
| 807.5761 | 1101 | 5.086 | 0.077 | 4.315 | 0.098 | 1.179 | 4.13E-14 |
| 829.5604 | 1101 | 2.570 | 0.087 | 1.559 | 0.144 | 1.648 | 4.96E-14 |
| 756.5498 | 1201 | 2.630 | 0.095 | 1.815 | 0.086 | 1.449 | 5.34E-14 |
| 519.3318 | 1101 | 3.772 | 0.113 | 2.595 | 0.157 | 1.454 | 5.48E-14 |
| 448.3563 | 1204 | 2.591 | 0.136 | 1.218 | 0.181 | 2.127 | 7.47E-14 |
| 590.4597 | 1204 | 1.815 | 0.155 | 0.467 | 0.153 | 3.883 | 1.13E-13 |
| 595.4925 | 1202 | 1.382 | 0.172 | 0.130 | 0.083 | 10.667 | 1.33E-13 |
| 755.5463 | 1201 | 3.794 | 0.096 | 3.047 | 0.072 | 1.245 | 2.47E-13 |
| 541.3138 | 1101 | 3.841 | 0.114 | 2.663 | 0.168 | 1.442 | 3.35E-13 |
| 542.317 | 1101 | 2.075 | 0.127 | 0.887 | 0.157 | 2.338 | 3.53E-13 |
| 576.4771 | 1204 | 3.435 | 0.154 | 1.899 | 0.218 | 1.809 | 5.17E-13 |
| 579.4963 | 1204 | 1.842 | 0.180 | 0.437 | 0.146 | 4.213 | 6.58E-13 |
| 574.463 | 1202 | 1.571 | 0.158 | 0.302 | 0.141 | 5.206 | 7.17E-13 |
| 574.4607 | 1204 | 2.939 | 0.144 | 1.485 | 0.214 | 1.979 | 9.40E-13 |
| 771.5778 | 1201 | 2.571 | 0.081 | 1.793 | 0.111 | 1.434 | 1.11E-12 |
| 779.5445 | 1101 | 5.753 | 0.106 | 4.896 | 0.103 | 1.175 | 1.68E-12 |
| 446.3406 | 1202 | 1.122 | 0.151 | 0.117 | 0.064 | 9.622 | 2.41E-12 |
| 597.5068 | 1202 | 1.653 | 0.195 | 0.294 | 0.114 | 5.628 | 2.57E-12 |
| 780.5475 | 1101 | 4.747 | 0.107 | 3.896 | 0.103 | 1.218 | 2.96E-12 |
| 518.3976 | 1204 | 1.666 | 0.184 | 0.330 | 0.135 | 5.050 | 3.35E-12 |
| 578.4931 | 1204 | 3.080 | 0.187 | 1.378 | 0.248 | 2.236 | 4.49E-12 |
| 592.4701 | 1202 | 1.058 | 0.159 | 0.048 | 0.049 | 21.965 | 5.41E-12 |
| 596.5029 | 1204 | 4.054 | 0.227 | 2.121 | 0.271 | 1.911 | 7.71E-12 |
| 817.5827 | 1202 | 1.929 | 0.102 | 1.010 | 0.136 | 1.909 | 8.34E-12 |
| 821.5337 | 1201 | 3.796 | 0.056 | 3.240 | 0.090 | 1.171 | 1.27E-11 |
| 597.5076 | 1204 | 2.845 | 0.225 | 1.098 | 0.228 | 2.592 | 1.66E-11 |
| 783.5778 | 1201 | 6.912 | 0.074 | 6.326 | 0.079 | 1.093 | 1.76E-11 |
| 854.5885 | 1202 | 4.322 | 0.101 | 3.409 | 0.143 | 1.268 | 2.42E-11 |
| 447.3433 | 1204 | 1.153 | 0.166 | 0.110 | 0.076 | 10.525 | 3.19E-11 |
| 596.5048 | 1202 | 3.032 | 0.236 | 1.328 | 0.208 | 2.284 | 3.26E-11 |
| 593.4742 | 1204 | 1.199 | 0.179 | 0.081 | 0.080 | 14.774 | 3.39E-11 |
| 829.5599 | 1201 | 5.678 | 0.059 | 5.099 | 0.098 | 1.114 | 3.50E-11 |
| 758.5657 | 1101 | 5.811 | 0.113 | 4.987 | 0.103 | 1.165 | 3.50E-11 |
| 757.5627 | 1101 | 6.813 | 0.117 | 5.975 | 0.104 | 1.140 | 4.68E-11 |
| 784.5811 | 1201 | 5.761 | 0.070 | 5.207 | 0.080 | 1.106 | 5.54E-11 |
| 484.3786 | 1204 | 1.065 | 0.184 | 0.000 | 0.000 | 1.065 | 5.91E-11 |
| 830.5883 | 1202 | 5.281 | 0.114 | 4.428 | 0.115 | 1.193 | 6.19E-11 |
| 853.5845 | 1202 | 5.306 | 0.107 | 4.402 | 0.141 | 1.205 | 6.49E-11 |
| 575.4635 | 1204 | 1.675 | 0.172 | 0.435 | 0.162 | 3.849 | 8.15E-11 |
| 512.4086 | 1204 | 1.346 | 0.218 | 0.063 | 0.062 | 21.466 | 8.16E-11 |
| 452.3876 | 1204 | 0.921 | 0.152 | 0.030 | 0.042 | 30.716 | 8.35E-11 |
| 476.3873 | 1204 | 1.353 | 0.139 | 0.356 | 0.130 | 3.804 | 9.08E-11 |
| 786.5965 | 1101 | 5.014 | 0.090 | 4.330 | 0.097 | 1.158 | 9.66E-11 |
| 830.5632 | 1201 | 4.686 | 0.057 | 4.113 | 0.102 | 1.139 | 1.03E-10 |
| 533.2881 | 1101 | 2.090 | 0.121 | 1.045 | 0.172 | 1.999 | 1.21E-10 |
| 785.5932 | 1101 | 6.079 | 0.089 | 5.404 | 0.097 | 1.125 | 1.28E-10 |
| 829.5846 | 1202 | 6.510 | 0.132 | 5.584 | 0.121 | 1.166 | 1.51E-10 |
| 522.4313 | 1204 | 2.524 | 0.140 | 1.335 | 0.195 | 1.891 | 1.54E-10 |

TABLE 3-continued

Accurate neutral mass features differing between CRC and normal serum (p < 0.05, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 540.4404 | 1202 | 1.289 | 0.166 | 0.245 | 0.104 | 5.265 | 1.87E-10 |
| 469.3865 | 1204 | 1.006 | 0.169 | 0.045 | 0.045 | 22.354 | 2.06E-10 |
| 850.7049 | 1203 | 2.885 | 0.147 | 1.574 | 0.226 | 1.833 | 2.13E-10 |
| 449.3614 | 1204 | 1.189 | 0.160 | 0.211 | 0.098 | 5.629 | 4.32E-10 |
| 540.4397 | 1204 | 2.096 | 0.216 | 0.710 | 0.169 | 2.951 | 5.41E-10 |
| 596.4796 | 1203 | 3.393 | 0.157 | 2.200 | 0.193 | 1.542 | 6.64E-10 |
| 618.4831 | 1201 | 1.939 | 0.207 | 0.629 | 0.159 | 3.083 | 7.03E-10 |
| 312.0014 | 1101 | 1.381 | 0.211 | 2.718 | 0.164 | 0.508 | 7.54E-10 |
| 440.3529 | 1204 | 1.169 | 0.173 | 0.166 | 0.094 | 7.058 | 1.08E-09 |
| 467.3718 | 1204 | 0.950 | 0.163 | 0.067 | 0.054 | 14.116 | 1.59E-09 |
| 822.537 | 1201 | 2.677 | 0.069 | 2.133 | 0.096 | 1.255 | 1.72E-09 |
| 578.4903 | 1202 | 1.141 | 0.171 | 0.182 | 0.088 | 6.270 | 2.17E-09 |
| 339.9965 | 1101 | 2.070 | 0.228 | 3.376 | 0.133 | 0.613 | 2.35E-09 |
| 558.4665 | 1202 | 2.384 | 0.145 | 1.060 | 0.264 | 2.250 | 3.15E-09 |
| 382.1081 | 1101 | 0.233 | 0.094 | 1.105 | 0.176 | 0.211 | 3.79E-09 |
| 599.5006 | 1203 | 5.116 | 0.137 | 4.193 | 0.150 | 1.220 | 5.59E-09 |
| 803.5446 | 1101 | 4.329 | 0.111 | 3.539 | 0.139 | 1.223 | 6.60E-09 |
| 831.5762 | 1101 | 3.397 | 0.080 | 2.792 | 0.112 | 1.217 | 6.92E-09 |
| 804.5477 | 1101 | 3.349 | 0.114 | 2.551 | 0.141 | 1.313 | 9.08E-09 |
| 598.4963 | 1203 | 6.342 | 0.142 | 5.413 | 0.153 | 1.172 | 1.03E-08 |
| 797.5338 | 1201 | 3.695 | 0.071 | 4.125 | 0.065 | 0.896 | 1.36E-08 |
| 416.3666 | 1204 | 0.987 | 0.175 | 0.079 | 0.080 | 12.444 | 1.39E-08 |
| 826.5569 | 1202 | 2.314 | 0.139 | 1.360 | 0.173 | 1.702 | 1.64E-08 |
| 761.5844 | 1201 | 3.463 | 0.078 | 3.926 | 0.073 | 0.882 | 2.56E-08 |
| 879.7421 | 1203 | 4.626 | 0.167 | 3.620 | 0.167 | 1.278 | 3.85E-08 |
| 597.4839 | 1203 | 2.015 | 0.179 | 0.922 | 0.185 | 2.186 | 4.01E-08 |
| 878.7384 | 1203 | 5.443 | 0.166 | 4.437 | 0.169 | 1.227 | 4.16E-08 |
| 851.7098 | 1203 | 2.239 | 0.170 | 1.100 | 0.215 | 2.035 | 4.28E-08 |
| 519.332 | 1201 | 2.979 | 0.072 | 2.485 | 0.096 | 1.199 | 4.91E-08 |
| 868.7532 | 1203 | 2.234 | 0.153 | 1.193 | 0.203 | 1.873 | 5.20E-08 |
| 810.5967 | 1101 | 4.041 | 0.081 | 3.445 | 0.124 | 1.173 | 5.66E-08 |
| 824.6891 | 1203 | 2.054 | 0.201 | 0.854 | 0.205 | 2.405 | 6.37E-08 |
| 809.5934 | 1101 | 5.021 | 0.083 | 4.443 | 0.118 | 1.130 | 7.39E-08 |
| 853.7241 | 1203 | 4.663 | 0.150 | 3.698 | 0.183 | 1.261 | 7.75E-08 |
| 852.7206 | 1203 | 5.373 | 0.149 | 4.411 | 0.184 | 1.218 | 7.85E-08 |
| 798.537 | 1201 | 2.627 | 0.067 | 3.017 | 0.066 | 0.871 | 8.85E-08 |
| 496.4164 | 1204 | 2.089 | 0.186 | 1.019 | 0.179 | 2.050 | 9.50E-08 |
| 858.6852 | 1202 | 2.103 | 0.096 | 2.673 | 0.101 | 0.787 | 1.12E-07 |
| 558.4659 | 1204 | 4.053 | 0.131 | 3.023 | 0.235 | 1.341 | 1.50E-07 |
| 563.595 | 1102 | 0.875 | 0.130 | 1.657 | 0.147 | 0.528 | 1.67E-07 |
| 832.5797 | 1101 | 2.426 | 0.082 | 1.855 | 0.123 | 1.308 | 1.89E-07 |
| 795.5179 | 1201 | 5.214 | 0.062 | 4.861 | 0.063 | 1.073 | 2.02E-07 |
| 782.5653 | 1101 | 5.050 | 0.102 | 4.437 | 0.118 | 1.138 | 2.09E-07 |
| 760.5811 | 1201 | 5.562 | 0.082 | 6.013 | 0.077 | 0.925 | 2.10E-07 |
| 559.4695 | 1204 | 2.709 | 0.123 | 1.698 | 0.240 | 1.596 | 2.11E-07 |
| 779.5439 | 1201 | 8.173 | 0.068 | 7.796 | 0.065 | 1.048 | 2.17E-07 |
| 560.4796 | 1203 | 3.168 | 0.104 | 2.532 | 0.126 | 1.251 | 2.63E-07 |
| 877.7266 | 1203 | 2.795 | 0.194 | 1.591 | 0.244 | 1.756 | 2.74E-07 |
| 825.5533 | 1202 | 3.304 | 0.152 | 2.461 | 0.153 | 1.343 | 3.25E-07 |
| 183.066 | 1101 | 3.212 | 0.092 | 2.455 | 0.185 | 1.308 | 3.33E-07 |
| 758.5654 | 1201 | 7.099 | 0.085 | 6.647 | 0.077 | 1.068 | 3.36E-07 |
| 290.0628 | 1101 | 1.143 | 0.256 | 0.032 | 0.045 | 36.180 | 3.39E-07 |
| 541.3139 | 1201 | 2.953 | 0.076 | 2.495 | 0.094 | 1.184 | 4.09E-07 |
| 565.3391 | 1202 | 7.189 | 0.115 | 6.499 | 0.139 | 1.106 | 4.17E-07 |
| 796.5213 | 1201 | 4.064 | 0.062 | 3.723 | 0.063 | 1.091 | 4.87E-07 |
| 440.2897 | 1201 | 0.000 | 0.000 | 0.776 | 0.226 | 0.000 | 5.04E-07 |
| 845.5341 | 1201 | 2.938 | 0.063 | 2.518 | 0.095 | 1.167 | 5.07E-07 |
| 781.5619 | 1101 | 6.005 | 0.103 | 5.417 | 0.116 | 1.109 | 5.33E-07 |
| 847.5937 | 1202 | 1.831 | 0.157 | 0.979 | 0.157 | 1.869 | 5.47E-07 |
| 422.3404 | 1204 | 0.642 | 0.144 | 0.025 | 0.036 | 25.237 | 5.47E-07 |
| 495.4022 | 1204 | 0.753 | 0.166 | 0.042 | 0.041 | 18.100 | 5.47E-07 |
| 202.0453 | 1101 | 3.261 | 0.222 | 4.340 | 0.158 | 0.751 | 5.70E-07 |
| 803.5676 | 1202 | 8.206 | 0.144 | 7.440 | 0.137 | 1.103 | 5.76E-07 |
| 804.5711 | 1202 | 6.699 | 0.135 | 6.008 | 0.118 | 1.115 | 6.58E-07 |
| 544.4483 | 1203 | 2.547 | 0.142 | 1.728 | 0.168 | 1.474 | 7.19E-07 |
| 561.5983 | 1102 | 1.422 | 0.132 | 2.159 | 0.145 | 0.658 | 7.20E-07 |
| 560.4831 | 1204 | 3.752 | 0.107 | 2.718 | 0.276 | 1.380 | 7.41E-07 |
| 648.3846 | 1101 | 0.378 | 0.102 | 1.014 | 0.141 | 0.372 | 7.73E-07 |
| 218.0369 | 1102 | 1.332 | 0.196 | 2.429 | 0.221 | 0.548 | 8.72E-07 |
| 827.7087 | 1203 | 3.409 | 0.166 | 2.410 | 0.217 | 1.415 | 9.04E-07 |
| 807.5759 | 1201 | 7.358 | 0.050 | 7.060 | 0.065 | 1.042 | 9.23E-07 |
| 826.7047 | 1203 | 4.145 | 0.171 | 3.170 | 0.203 | 1.307 | 9.68E-07 |
| 757.5619 | 1201 | 8.087 | 0.100 | 7.586 | 0.085 | 1.066 | 9.71E-07 |

TABLE 3-continued

Accurate neutral mass features differing between CRC and normal serum (p < 0.05, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 566.3433 | 1202 | 5.332 | 0.101 | 4.739 | 0.127 | 1.125 | 9.98E−07 |
| 805.5616 | 1101 | 4.724 | 0.081 | 4.184 | 0.128 | 1.129 | 1.03E−06 |
| 586.4957 | 1203 | 2.208 | 0.109 | 1.500 | 0.165 | 1.471 | 1.03E−06 |
| 244.056 | 1101 | 1.789 | 0.174 | 2.644 | 0.143 | 0.677 | 1.16E−06 |
| 276.2093 | 1204 | 3.348 | 0.103 | 2.797 | 0.109 | 1.197 | 1.29E−06 |
| 428.3651 | 1201 | 3.186 | 0.070 | 2.766 | 0.095 | 1.152 | 1.33E−06 |
| 744.496 | 1204 | 3.432 | 0.077 | 2.882 | 0.139 | 1.191 | 1.43E−06 |
| 541.4432 | 1204 | 0.842 | 0.183 | 0.079 | 0.064 | 10.679 | 1.59E−06 |
| 823.5494 | 1201 | 3.978 | 0.068 | 3.612 | 0.075 | 1.101 | 1.68E−06 |
| 673.6198 | 1204 | 3.299 | 0.093 | 3.737 | 0.072 | 0.883 | 1.82E−06 |
| 798.6741 | 1203 | 1.579 | 0.205 | 0.598 | 0.171 | 2.641 | 2.06E−06 |
| 521.3476 | 1101 | 3.429 | 0.100 | 2.753 | 0.170 | 1.246 | 2.07E−06 |
| 543.3292 | 1101 | 3.593 | 0.101 | 2.921 | 0.168 | 1.230 | 2.09E−06 |
| 780.5473 | 1201 | 7.108 | 0.059 | 6.801 | 0.062 | 1.045 | 2.15E−06 |
| 743.5483 | 1204 | 3.857 | 0.086 | 3.407 | 0.092 | 1.132 | 2.20E−06 |
| 429.3743 | 1204 | 2.242 | 0.123 | 1.618 | 0.122 | 1.386 | 2.27E−06 |
| 560.4816 | 1202 | 1.965 | 0.128 | 1.002 | 0.257 | 1.962 | 2.46E−06 |
| 744.5537 | 1204 | 2.960 | 0.084 | 2.515 | 0.094 | 1.177 | 2.71E−06 |
| 561.4869 | 1204 | 2.350 | 0.125 | 1.372 | 0.267 | 1.713 | 2.92E−06 |
| 763.5146 | 1201 | 1.401 | 0.131 | 2.052 | 0.128 | 0.683 | 3.11E−06 |
| 555.3103 | 1102 | 1.936 | 0.126 | 1.230 | 0.162 | 1.574 | 3.19E−06 |
| 260.2136 | 1203 | 1.742 | 0.129 | 1.080 | 0.139 | 1.614 | 3.40E−06 |
| 876.7228 | 1203 | 3.508 | 0.201 | 2.521 | 0.193 | 1.391 | 3.42E−06 |
| 524.3666 | 1101 | 1.671 | 0.122 | 0.952 | 0.173 | 1.756 | 3.43E−06 |
| 268.132 | 1204 | 0.908 | 0.144 | 0.260 | 0.108 | 3.497 | 3.98E−06 |
| 661.6227 | 1204 | 3.016 | 0.105 | 2.518 | 0.095 | 1.198 | 4.47E−06 |
| 727.5563 | 1204 | 2.134 | 0.134 | 1.335 | 0.197 | 1.598 | 4.49E−06 |
| 648.5862 | 1203 | 4.067 | 0.086 | 3.589 | 0.113 | 1.133 | 4.80E−06 |
| 758.5096 | 1204 | 2.677 | 0.091 | 2.168 | 0.121 | 1.235 | 4.82E−06 |
| 808.5793 | 1201 | 6.244 | 0.044 | 5.985 | 0.064 | 1.043 | 5.15E−06 |
| 827.5684 | 1202 | 7.255 | 0.139 | 6.530 | 0.166 | 1.111 | 6.33E−06 |
| 828.5726 | 1202 | 6.015 | 0.126 | 5.362 | 0.148 | 1.122 | 6.54E−06 |
| 570.4649 | 1203 | 2.474 | 0.125 | 1.717 | 0.196 | 1.440 | 6.59E−06 |
| 562.4993 | 1204 | 2.569 | 0.118 | 1.839 | 0.192 | 1.397 | 7.02E−06 |
| 392.2932 | 1204 | 2.106 | 0.201 | 0.988 | 0.275 | 2.132 | 7.35E−06 |
| 688.4688 | 1204 | 3.330 | 0.077 | 2.947 | 0.086 | 1.130 | 8.09E−06 |
| 264.2453 | 1203 | 2.851 | 0.098 | 3.278 | 0.076 | 0.870 | 8.41E−06 |
| 559.4698 | 1202 | 1.156 | 0.147 | 0.399 | 0.178 | 2.901 | 9.51E−06 |
| 743.5463 | 1201 | 2.075 | 0.091 | 1.610 | 0.109 | 1.289 | 9.72E−06 |
| 806.5648 | 1101 | 3.768 | 0.084 | 3.275 | 0.130 | 1.151 | 1.05E−05 |
| 565.3398 | 1102 | 3.209 | 0.122 | 2.559 | 0.161 | 1.254 | 1.11E−05 |
| 545.3451 | 1101 | 3.523 | 0.117 | 2.811 | 0.193 | 1.253 | 1.13E−05 |
| 630.4874 | 1204 | 3.273 | 0.195 | 2.306 | 0.224 | 1.420 | 1.14E−05 |
| 523.3633 | 1101 | 3.385 | 0.107 | 2.713 | 0.186 | 1.248 | 1.23E−05 |
| 310.2881 | 1204 | 2.825 | 0.124 | 3.408 | 0.127 | 0.829 | 1.27E−05 |
| 832.6026 | 1202 | 5.437 | 0.119 | 4.898 | 0.111 | 1.110 | 1.33E−05 |
| 880.7535 | 1203 | 6.327 | 0.159 | 5.592 | 0.157 | 1.131 | 1.34E−05 |
| 426.3714 | 1204 | 0.671 | 0.138 | 0.125 | 0.079 | 5.380 | 1.38E−05 |
| 216.0399 | 1102 | 2.911 | 0.205 | 3.930 | 0.242 | 0.741 | 1.41E−05 |
| 793.5987 | 1101 | 2.239 | 0.084 | 1.808 | 0.106 | 1.238 | 1.45E−05 |
| 638.4885 | 1201 | 1.839 | 0.165 | 1.096 | 0.160 | 1.678 | 1.80E−05 |
| 222.0699 | 1202 | 2.486 | 0.203 | 1.492 | 0.239 | 1.666 | 1.82E−05 |
| 257.8107 | 1101 | 2.777 | 0.068 | 3.098 | 0.075 | 0.897 | 1.95E−05 |
| 881.7573 | 1203 | 5.629 | 0.157 | 4.925 | 0.153 | 1.143 | 1.96E−05 |
| 749.541 | 1204 | 2.884 | 0.097 | 2.271 | 0.178 | 1.270 | 1.99E−05 |
| 831.5991 | 1202 | 6.714 | 0.146 | 6.084 | 0.128 | 1.104 | 2.03E−05 |
| 805.5832 | 1102 | 2.664 | 0.094 | 3.152 | 0.126 | 0.845 | 2.06E−05 |
| 550.4605 | 1204 | 1.671 | 0.170 | 0.881 | 0.182 | 1.897 | 2.10E−05 |
| 759.5777 | 1201 | 6.723 | 0.089 | 7.100 | 0.074 | 0.947 | 2.22E−05 |
| 802.5317 | 1102 | 2.811 | 0.137 | 2.206 | 0.132 | 1.274 | 2.39E−05 |
| 253.8165 | 1101 | 3.252 | 0.073 | 3.571 | 0.068 | 0.911 | 2.41E−05 |
| 692.5571 | 1204 | 2.642 | 0.103 | 3.179 | 0.144 | 0.831 | 2.76E−05 |
| 606.415 | 1202 | 0.784 | 0.212 | 0.044 | 0.043 | 17.964 | 2.84E−05 |
| 801.5283 | 1201 | 3.911 | 0.133 | 3.339 | 0.122 | 1.172 | 2.85E−05 |
| 649.5893 | 1203 | 3.030 | 0.096 | 2.517 | 0.141 | 1.204 | 2.93E−05 |
| 430.3817 | 1204 | 4.158 | 0.157 | 3.535 | 0.113 | 1.176 | 3.22E−05 |
| 546.3482 | 1101 | 1.930 | 0.121 | 1.292 | 0.176 | 1.494 | 3.51E−05 |
| 738.5445 | 1102 | 1.368 | 0.100 | 1.857 | 0.127 | 0.737 | 3.54E−05 |
| 188.0491 | 1102 | 1.405 | 0.256 | 0.448 | 0.145 | 3.134 | 3.68E−05 |
| 336.2664 | 1203 | 3.612 | 0.099 | 3.191 | 0.091 | 1.132 | 3.72E−05 |
| 553.3853 | 1201 | 0.133 | 0.067 | 0.907 | 0.268 | 0.146 | 3.76E−05 |
| 263.8453 | 1101 | 2.545 | 0.083 | 2.912 | 0.087 | 0.874 | 4.05E−05 |
| 255.8136 | 1101 | 3.727 | 0.071 | 4.031 | 0.069 | 0.925 | 4.14E−05 |

TABLE 3-continued

Accurate neutral mass features differing between CRC and normal serum (p < 0.05, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 731.491 | 1204 | 3.147 | 0.123 | 2.568 | 0.148 | 1.225 | 4.16E−05 |
| 855.7394 | 1203 | 6.558 | 0.154 | 5.877 | 0.161 | 1.116 | 4.23E−05 |
| 824.5528 | 1201 | 2.869 | 0.069 | 2.566 | 0.071 | 1.118 | 4.35E−05 |
| 772.5279 | 1204 | 2.216 | 0.107 | 1.624 | 0.172 | 1.364 | 4.42E−05 |
| 785.5933 | 1201 | 7.132 | 0.070 | 6.820 | 0.075 | 1.046 | 4.47E−05 |
| 278.2251 | 1204 | 5.577 | 0.108 | 5.109 | 0.109 | 1.091 | 4.78E−05 |
| 566.4556 | 1204 | 0.666 | 0.155 | 0.110 | 0.076 | 6.046 | 5.03E−05 |
| 759.5154 | 1204 | 2.271 | 0.119 | 1.671 | 0.167 | 1.359 | 5.36E−05 |
| 854.7356 | 1203 | 7.289 | 0.158 | 6.609 | 0.162 | 1.103 | 5.37E−05 |
| 763.5147 | 1202 | 1.289 | 0.148 | 1.919 | 0.147 | 0.672 | 5.37E−05 |
| 812.6124 | 1101 | 2.277 | 0.089 | 1.827 | 0.126 | 1.246 | 5.55E−05 |
| 495.3318 | 1101 | 5.159 | 0.100 | 4.604 | 0.166 | 1.121 | 5.75E−05 |
| 249.9647 | 1101 | 2.274 | 0.161 | 1.511 | 0.204 | 1.505 | 5.79E−05 |
| 568.3559 | 1201 | 0.018 | 0.025 | 0.535 | 0.191 | 0.034 | 6.01E−05 |
| 799.6776 | 1203 | 0.955 | 0.193 | 0.251 | 0.118 | 3.804 | 6.53E−05 |
| 563.396 | 1204 | 0.996 | 0.197 | 0.259 | 0.135 | 3.845 | 6.61E−05 |
| 748.572 | 1102 | 2.381 | 0.107 | 2.886 | 0.138 | 0.825 | 6.91E−05 |
| 518.3171 | 1101 | 3.505 | 0.112 | 2.935 | 0.165 | 1.194 | 6.94E−05 |
| 279.2286 | 1204 | 3.300 | 0.109 | 2.824 | 0.120 | 1.168 | 7.10E−05 |
| 517.3137 | 1101 | 5.483 | 0.113 | 4.913 | 0.165 | 1.116 | 7.11E−05 |
| 496.3352 | 1101 | 3.327 | 0.108 | 2.766 | 0.165 | 1.203 | 7.26E−05 |
| 431.3856 | 1204 | 2.686 | 0.149 | 2.064 | 0.149 | 1.302 | 7.78E−05 |
| 328.2412 | 1204 | 3.467 | 0.149 | 4.078 | 0.143 | 0.850 | 7.97E−05 |
| 408.2547 | 1201 | 0.447 | 0.130 | 1.096 | 0.190 | 0.408 | 8.53E−05 |
| 631.491 | 1204 | 2.071 | 0.211 | 1.175 | 0.224 | 1.762 | 8.68E−05 |
| 283.26 | 1204 | 7.010 | 0.124 | 7.515 | 0.120 | 0.933 | 9.26E−05 |
| 277.886 | 1101 | 3.032 | 0.058 | 3.288 | 0.068 | 0.922 | 9.60E−05 |
| 274.1936 | 1204 | 1.684 | 0.110 | 1.169 | 0.146 | 1.441 | 9.97E−05 |
| 536.4799 | 1203 | 2.866 | 0.226 | 1.889 | 0.256 | 1.517 | 1.02E−04 |
| 452.2381 | 1201 | 2.521 | 0.064 | 2.273 | 0.055 | 1.109 | 1.04E−04 |
| 788.6128 | 1201 | 2.826 | 0.070 | 3.175 | 0.105 | 0.890 | 1.06E−04 |
| 767.583 | 1101 | 2.301 | 0.088 | 1.881 | 0.122 | 1.223 | 1.08E−04 |
| 855.6004 | 1202 | 6.120 | 0.134 | 5.526 | 0.161 | 1.107 | 1.10E−04 |
| 282.257 | 1204 | 9.595 | 0.130 | 10.114 | 0.124 | 0.949 | 1.12E−04 |
| 542.47 | 1203 | 1.218 | 0.174 | 0.532 | 0.162 | 2.291 | 1.21E−04 |
| 856.6045 | 1202 | 5.073 | 0.122 | 4.531 | 0.149 | 1.119 | 1.21E−04 |
| 771.5806 | 1204 | 2.315 | 0.089 | 1.836 | 0.153 | 1.261 | 1.24E−04 |
| 494.434 | 1203 | 2.948 | 0.346 | 1.559 | 0.339 | 1.891 | 1.24E−04 |
| 786.5967 | 1201 | 6.015 | 0.065 | 5.735 | 0.075 | 1.049 | 1.30E−04 |
| 568.4729 | 1204 | 1.088 | 0.191 | 0.398 | 0.137 | 2.733 | 1.35E−04 |
| 855.5756 | 1201 | 3.881 | 0.094 | 4.328 | 0.134 | 0.897 | 1.38E−04 |
| 859.7708 | 1203 | 5.116 | 0.170 | 5.728 | 0.122 | 0.893 | 1.40E−04 |
| 519.4376 | 1203 | 0.921 | 0.221 | 0.179 | 0.112 | 5.145 | 1.44E−04 |
| 326.2197 | 1201 | 2.476 | 0.355 | 3.915 | 0.368 | 0.633 | 1.47E−04 |
| 338.2823 | 1203 | 4.938 | 0.078 | 5.268 | 0.090 | 0.937 | 1.51E−04 |
| 694.573 | 1204 | 1.900 | 0.163 | 2.530 | 0.151 | 0.751 | 1.56E−04 |
| 352.2296 | 1201 | 0.691 | 0.197 | 1.581 | 0.260 | 0.437 | 1.61E−04 |
| 259.9417 | 1101 | 2.617 | 0.136 | 1.986 | 0.191 | 1.318 | 1.81E−04 |
| 749.5757 | 1102 | 1.277 | 0.136 | 1.823 | 0.144 | 0.700 | 1.86E−04 |
| 226.0687 | 1102 | 1.303 | 0.192 | 2.053 | 0.194 | 0.635 | 2.18E−04 |
| 748.5726 | 1202 | 3.195 | 0.104 | 3.585 | 0.095 | 0.891 | 2.19E−04 |
| 217.9126 | 1101 | 2.667 | 0.133 | 3.135 | 0.098 | 0.851 | 2.24E−04 |
| 745.4986 | 1204 | 2.011 | 0.166 | 1.294 | 0.212 | 1.555 | 2.36E−04 |
| 495.4373 | 1203 | 1.699 | 0.297 | 0.620 | 0.254 | 2.738 | 2.54E−04 |
| 215.9154 | 1101 | 4.225 | 0.094 | 4.601 | 0.103 | 0.918 | 2.55E−04 |
| 843.518 | 1201 | 3.089 | 0.094 | 3.477 | 0.111 | 0.889 | 2.62E−04 |
| 194.0802 | 1203 | 0.635 | 0.201 | 0.029 | 0.041 | 21.815 | 2.66E−04 |
| 285.1365 | 1201 | 1.200 | 0.277 | 0.260 | 0.189 | 4.614 | 2.72E−04 |
| 552.3819 | 1201 | 0.921 | 0.175 | 1.952 | 0.372 | 0.472 | 2.95E−04 |
| 750.5441 | 1204 | 1.757 | 0.149 | 1.130 | 0.188 | 1.555 | 2.98E−04 |
| 329.2441 | 1204 | 1.195 | 0.176 | 1.860 | 0.174 | 0.642 | 2.99E−04 |
| 803.5441 | 1201 | 7.309 | 0.075 | 6.986 | 0.100 | 1.046 | 3.13E−04 |
| 829.586 | 1102 | 2.482 | 0.112 | 1.983 | 0.158 | 1.251 | 3.21E−04 |
| 870.7694 | 1203 | 2.133 | 0.152 | 1.468 | 0.208 | 1.453 | 3.23E−04 |
| 530.3997 | 1201 | 0.063 | 0.043 | 0.568 | 0.208 | 0.111 | 3.72E−04 |
| 819.5628 | 1202 | 1.666 | 0.185 | 0.998 | 0.174 | 1.670 | 4.06E−04 |
| 691.1955 | 1102 | 1.840 | 0.082 | 2.128 | 0.071 | 0.865 | 4.06E−04 |
| 853.5599 | 1201 | 2.536 | 0.090 | 2.159 | 0.117 | 1.174 | 4.08E−04 |
| 466.4018 | 1203 | 1.299 | 0.308 | 0.270 | 0.225 | 4.807 | 4.09E−04 |
| 856.5788 | 1201 | 2.843 | 0.108 | 3.299 | 0.145 | 0.862 | 4.29E−04 |
| 625.5165 | 1203 | 2.293 | 0.074 | 1.852 | 0.168 | 1.238 | 4.58E−04 |
| 751.5554 | 1204 | 3.149 | 0.107 | 2.612 | 0.193 | 1.206 | 4.98E−04 |
| 537.4829 | 1203 | 1.394 | 0.228 | 0.591 | 0.219 | 2.360 | 6.17E−04 |

TABLE 3-continued

Accurate neutral mass features differing between CRC and normal serum (p < 0.05, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 469.3608 | 1201 | 2.840 | 0.087 | 2.517 | 0.096 | 1.128 | 6.56E-04 |
| 750.5397 | 1202 | 1.844 | 0.076 | 1.385 | 0.182 | 1.331 | 6.92E-04 |
| 217.0698 | 1202 | 0.000 | 0.000 | 0.533 | 0.239 | 0.000 | 6.92E-04 |
| 805.5605 | 1201 | 7.202 | 0.053 | 6.978 | 0.076 | 1.032 | 7.15E-04 |
| 724.5494 | 1201 | 2.164 | 0.152 | 2.644 | 0.108 | 0.818 | 7.29E-04 |
| 752.5577 | 1204 | 2.057 | 0.132 | 1.473 | 0.208 | 1.397 | 7.56E-04 |
| 642.5195 | 1201 | 2.218 | 0.124 | 2.644 | 0.118 | 0.839 | 7.85E-04 |
| 205.8866 | 1101 | 2.131 | 0.163 | 2.642 | 0.119 | 0.807 | 8.48E-04 |
| 328.2604 | 1202 | 2.681 | 0.229 | 3.545 | 0.276 | 0.756 | 8.54E-04 |
| 577.5142 | 1203 | 8.031 | 0.134 | 8.453 | 0.102 | 0.950 | 9.73E-04 |
| 693.56 | 1204 | 1.549 | 0.169 | 2.151 | 0.184 | 0.720 | 1.01E-03 |
| 310.2152 | 1204 | 2.713 | 0.091 | 2.415 | 0.081 | 1.123 | 1.02E-03 |
| 518.4343 | 1203 | 2.231 | 0.268 | 1.384 | 0.216 | 1.612 | 1.07E-03 |
| 566.3437 | 1102 | 1.489 | 0.141 | 0.990 | 0.155 | 1.503 | 1.09E-03 |
| 689.6527 | 1204 | 2.424 | 0.124 | 2.039 | 0.096 | 1.189 | 1.11E-03 |
| 804.5474 | 1201 | 6.295 | 0.071 | 6.015 | 0.097 | 1.047 | 1.12E-03 |
| 576.5109 | 1203 | 9.389 | 0.132 | 9.799 | 0.102 | 0.958 | 1.13E-03 |
| 440.2713 | 1201 | 0.264 | 0.095 | 0.737 | 0.188 | 0.358 | 1.16E-03 |
| 449.3171 | 1204 | 0.922 | 0.216 | 0.281 | 0.143 | 3.285 | 1.24E-03 |
| 459.1582 | 1203 | 1.001 | 0.232 | 1.912 | 0.321 | 0.524 | 1.26E-03 |
| 874.7062 | 1203 | 0.890 | 0.194 | 0.308 | 0.135 | 2.887 | 1.26E-03 |
| 281.2447 | 1204 | 6.344 | 0.106 | 5.984 | 0.111 | 1.060 | 1.32E-03 |
| 329.264 | 1202 | 0.790 | 0.183 | 1.472 | 0.232 | 0.537 | 1.35E-03 |
| 537.4501 | 1204 | 2.198 | 0.165 | 1.531 | 0.246 | 1.435 | 1.43E-03 |
| 280.2412 | 1204 | 8.699 | 0.109 | 8.331 | 0.114 | 1.044 | 1.46E-03 |
| 825.6926 | 1203 | 1.229 | 0.204 | 0.595 | 0.171 | 2.066 | 1.46E-03 |
| 804.5717 | 1102 | 2.955 | 0.096 | 2.601 | 0.121 | 1.136 | 1.47E-03 |
| 588.5115 | 1203 | 3.617 | 0.089 | 3.315 | 0.096 | 1.091 | 1.52E-03 |
| 602.5286 | 1203 | 8.518 | 0.111 | 8.889 | 0.115 | 0.958 | 1.53E-03 |
| 444.3599 | 1201 | 1.999 | 0.068 | 1.694 | 0.121 | 1.181 | 1.54E-03 |
| 218.0193 | 1101 | 2.686 | 0.184 | 3.262 | 0.161 | 0.823 | 1.56E-03 |
| 283.9863 | 1101 | 0.029 | 0.040 | 0.430 | 0.187 | 0.066 | 1.58E-03 |
| 858.766 | 1203 | 6.089 | 0.172 | 6.596 | 0.123 | 0.923 | 1.59E-03 |
| 860.7756 | 1203 | 3.656 | 0.189 | 4.201 | 0.124 | 0.870 | 1.60E-03 |
| 859.7718 | 1204 | 1.061 | 0.195 | 1.700 | 0.198 | 0.624 | 1.74E-03 |
| 614.3424 | 1202 | 2.236 | 0.096 | 2.558 | 0.104 | 0.874 | 1.75E-03 |
| 877.5815 | 1202 | 1.648 | 0.158 | 1.125 | 0.165 | 1.465 | 1.76E-03 |
| 468.3574 | 1201 | 4.315 | 0.083 | 4.044 | 0.085 | 1.067 | 1.79E-03 |
| 461.1552 | 1203 | 0.756 | 0.215 | 1.596 | 0.316 | 0.474 | 1.87E-03 |
| 578.5176 | 1203 | 5.603 | 0.257 | 6.290 | 0.120 | 0.891 | 1.91E-03 |
| 712.4704 | 1204 | 1.935 | 0.131 | 1.470 | 0.163 | 1.316 | 1.95E-03 |
| 326.2261 | 1204 | 1.887 | 0.172 | 2.476 | 0.201 | 0.762 | 2.08E-03 |
| 749.5359 | 1202 | 2.784 | 0.085 | 2.366 | 0.179 | 1.176 | 2.13E-03 |
| 858.7678 | 1204 | 1.862 | 0.219 | 2.525 | 0.192 | 0.737 | 2.21E-03 |
| 221.0733 | 1202 | 0.635 | 0.176 | 0.158 | 0.100 | 4.014 | 2.25E-03 |
| 523.4675 | 1203 | 3.901 | 0.258 | 3.075 | 0.264 | 1.269 | 2.25E-03 |
| 603.532 | 1203 | 7.217 | 0.111 | 7.576 | 0.117 | 0.953 | 2.27E-03 |
| 626.5286 | 1203 | 3.408 | 0.067 | 3.168 | 0.087 | 1.076 | 2.33E-03 |
| 269.9705 | 1101 | 3.238 | 0.143 | 2.783 | 0.145 | 1.164 | 2.33E-03 |
| 589.3396 | 1202 | 6.112 | 0.115 | 5.739 | 0.122 | 1.065 | 2.34E-03 |
| 564.513 | 1203 | 3.173 | 0.185 | 2.575 | 0.196 | 1.232 | 2.34E-03 |
| 460.1603 | 1203 | 0.298 | 0.129 | 0.843 | 0.223 | 0.354 | 2.39E-03 |
| 304.2379 | 1201 | 2.272 | 0.224 | 3.075 | 0.296 | 0.739 | 2.44E-03 |
| 834.5961 | 1201 | 3.998 | 0.067 | 4.255 | 0.100 | 0.940 | 2.45E-03 |
| 690.4865 | 1204 | 2.157 | 0.158 | 2.587 | 0.097 | 0.834 | 2.49E-03 |
| 749.5767 | 1202 | 2.180 | 0.106 | 2.504 | 0.100 | 0.870 | 2.55E-03 |
| 854.7373 | 1204 | 1.519 | 0.199 | 0.909 | 0.190 | 1.671 | 2.66E-03 |
| 830.589 | 1102 | 1.478 | 0.127 | 1.069 | 0.137 | 1.382 | 2.73E-03 |
| 558.4093 | 1204 | 1.158 | 0.209 | 1.868 | 0.255 | 0.620 | 2.76E-03 |
| 339.285 | 1203 | 2.667 | 0.112 | 2.983 | 0.087 | 0.894 | 2.94E-03 |
| 534.4658 | 1203 | 1.939 | 0.173 | 1.342 | 0.221 | 1.445 | 2.97E-03 |
| 183.066 | 1201 | 4.591 | 0.102 | 4.277 | 0.102 | 1.073 | 3.05E-03 |
| 575.2726 | 1101 | 2.063 | 0.102 | 1.683 | 0.151 | 1.226 | 3.14E-03 |
| 342.2198 | 1204 | 0.668 | 0.156 | 1.178 | 0.183 | 0.567 | 3.28E-03 |
| 282.2555 | 1202 | 2.757 | 0.245 | 3.580 | 0.304 | 0.770 | 3.29E-03 |
| 262.2294 | 1203 | 3.003 | 0.113 | 2.708 | 0.066 | 1.109 | 3.30E-03 |
| 819.5179 | 1201 | 4.478 | 0.065 | 4.242 | 0.093 | 1.056 | 3.31E-03 |
| 588.3273 | 1202 | 0.618 | 0.135 | 0.251 | 0.093 | 2.458 | 3.31E-03 |
| 842.7386 | 1203 | 1.913 | 0.190 | 1.345 | 0.182 | 1.422 | 3.38E-03 |
| 292.204 | 1204 | 2.164 | 0.112 | 1.822 | 0.114 | 1.187 | 3.43E-03 |
| 820.5213 | 1201 | 3.401 | 0.067 | 3.161 | 0.094 | 1.076 | 3.46E-03 |
| 743.5455 | 1202 | 2.517 | 0.134 | 2.144 | 0.105 | 1.174 | 3.48E-03 |
| 587.3228 | 1202 | 1.766 | 0.180 | 1.239 | 0.167 | 1.426 | 3.58E-03 |

TABLE 3-continued

Accurate neutral mass features differing between CRC and normal serum (p < 0.05, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 522.4639 | 1203 | 5.433 | 0.268 | 4.629 | 0.265 | 1.174 | 3.61E-03 |
| 102.0621 | 1204 | 2.296 | 0.108 | 1.948 | 0.128 | 1.179 | 3.84E-03 |
| 590.3426 | 1202 | 4.115 | 0.104 | 3.793 | 0.115 | 1.085 | 4.09E-03 |
| 915.5193 | 1201 | 3.194 | 0.058 | 3.020 | 0.061 | 1.058 | 4.38E-03 |
| 613.3402 | 1202 | 3.884 | 0.108 | 4.220 | 0.123 | 0.920 | 4.48E-03 |
| 617.0614 | 1204 | 4.859 | 0.065 | 4.651 | 0.080 | 1.045 | 4.87E-03 |
| 557.4528 | 1204 | 1.201 | 0.131 | 0.740 | 0.193 | 1.622 | 4.91E-03 |
| 789.5649 | 1201 | 3.490 | 0.063 | 3.690 | 0.077 | 0.946 | 4.93E-03 |
| 658.5913 | 1203 | 0.314 | 0.127 | 0.022 | 0.031 | 14.101 | 5.13E-03 |
| 746.5139 | 1204 | 1.980 | 0.178 | 2.454 | 0.143 | 0.807 | 5.43E-03 |
| 624.513 | 1203 | 3.469 | 0.078 | 3.208 | 0.108 | 1.081 | 5.56E-03 |
| 283.2589 | 1202 | 0.856 | 0.181 | 1.443 | 0.237 | 0.593 | 5.65E-03 |
| 589.5159 | 1203 | 2.441 | 0.093 | 2.154 | 0.110 | 1.133 | 5.68E-03 |
| 723.5217 | 1204 | 2.597 | 0.106 | 2.121 | 0.230 | 1.224 | 5.77E-03 |
| 556.4496 | 1204 | 2.541 | 0.091 | 2.166 | 0.178 | 1.173 | 6.26E-03 |
| 817.5011 | 1201 | 1.369 | 0.130 | 1.027 | 0.106 | 1.333 | 6.32E-03 |
| 803.5692 | 1102 | 4.118 | 0.106 | 3.792 | 0.129 | 1.086 | 6.40E-03 |
| 831.7406 | 1203 | 3.546 | 0.181 | 4.021 | 0.149 | 0.882 | 6.47E-03 |
| 493.422 | 1203 | 0.710 | 0.197 | 0.203 | 0.151 | 3.495 | 6.53E-03 |
| 833.5927 | 1201 | 4.967 | 0.066 | 5.190 | 0.096 | 0.957 | 6.58E-03 |
| 591.532 | 1203 | 2.662 | 0.116 | 2.334 | 0.118 | 1.141 | 6.66E-03 |
| 328.2391 | 1202 | 1.395 | 0.197 | 2.013 | 0.251 | 0.693 | 6.68E-03 |
| 296.2359 | 1204 | 4.596 | 0.125 | 4.259 | 0.115 | 1.079 | 6.95E-03 |
| 233.0648 | 1202 | 0.000 | 0.000 | 0.299 | 0.171 | 0.000 | 7.11E-03 |
| 223.9491 | 1101 | 2.665 | 0.135 | 3.041 | 0.137 | 0.876 | 7.48E-03 |
| 519.5021 | 1203 | 2.640 | 0.117 | 2.989 | 0.140 | 0.883 | 7.72E-03 |
| 350.2828 | 1204 | 1.458 | 0.166 | 1.008 | 0.161 | 1.447 | 7.87E-03 |
| 806.5641 | 1201 | 6.132 | 0.050 | 5.971 | 0.072 | 1.027 | 8.56E-03 |
| 623.5006 | 1203 | 1.607 | 0.141 | 1.167 | 0.191 | 1.377 | 8.77E-03 |
| 492.4181 | 1203 | 1.564 | 0.279 | 0.851 | 0.249 | 1.837 | 9.77E-03 |
| 564.5127 | 1202 | 0.208 | 0.096 | 0.576 | 0.186 | 0.361 | 9.98E-03 |
| 768.4964 | 1204 | 2.254 | 0.119 | 1.921 | 0.135 | 1.173 | 1.02E-02 |
| 807.5893 | 1202 | 2.736 | 0.126 | 3.050 | 0.106 | 0.897 | 1.03E-02 |
| 635.34 | 1202 | 0.641 | 0.142 | 1.098 | 0.212 | 0.584 | 1.05E-02 |
| 521.4526 | 1203 | 2.899 | 0.236 | 2.219 | 0.289 | 1.307 | 1.06E-02 |
| 600.5128 | 1203 | 8.293 | 0.117 | 7.966 | 0.135 | 1.041 | 1.08E-02 |
| 524.472 | 1203 | 1.524 | 0.269 | 0.839 | 0.249 | 1.817 | 1.08E-02 |
| 767.5501 | 1204 | 3.193 | 0.090 | 2.957 | 0.089 | 1.080 | 1.09E-02 |
| 844.5214 | 1201 | 2.139 | 0.090 | 2.427 | 0.136 | 0.881 | 1.15E-02 |
| 520.4497 | 1203 | 4.589 | 0.221 | 3.985 | 0.248 | 1.152 | 1.16E-02 |
| 695.646 | 1204 | 0.570 | 0.185 | 0.158 | 0.109 | 3.618 | 1.19E-02 |
| 449.3152 | 1202 | 1.438 | 0.249 | 0.851 | 0.189 | 1.689 | 1.21E-02 |
| 490.4024 | 1203 | 1.084 | 0.191 | 0.619 | 0.162 | 1.750 | 1.22E-02 |
| 559.4131 | 1204 | 0.163 | 0.084 | 0.536 | 0.205 | 0.304 | 1.23E-02 |
| 307.1185 | 1201 | 0.882 | 0.253 | 0.293 | 0.189 | 3.012 | 1.25E-02 |
| 739.5157 | 1202 | 1.103 | 0.162 | 1.482 | 0.121 | 0.745 | 1.26E-02 |
| 806.5863 | 1202 | 4.868 | 0.111 | 5.155 | 0.114 | 0.944 | 1.29E-02 |
| 830.7368 | 1203 | 4.321 | 0.188 | 4.767 | 0.151 | 0.907 | 1.32E-02 |
| 833.7567 | 1203 | 2.625 | 0.240 | 3.151 | 0.142 | 0.833 | 1.34E-02 |
| 601.5163 | 1203 | 7.045 | 0.117 | 6.727 | 0.136 | 1.047 | 1.37E-02 |
| 508.4487 | 1203 | 0.723 | 0.200 | 0.240 | 0.178 | 3.014 | 1.45E-02 |
| 224.1416 | 1204 | 1.978 | 0.145 | 1.617 | 0.142 | 1.223 | 1.49E-02 |
| 565.5157 | 1203 | 1.644 | 0.229 | 1.074 | 0.225 | 1.530 | 1.49E-02 |
| 832.7528 | 1203 | 3.413 | 0.248 | 3.948 | 0.147 | 0.865 | 1.50E-02 |
| 356.2929 | 1204 | 0.288 | 0.139 | 0.016 | 0.023 | 17.586 | 1.52E-02 |
| 793.5383 | 1102 | 2.428 | 0.098 | 2.150 | 0.129 | 1.129 | 1.54E-02 |
| 592.5453 | 1203 | 0.774 | 0.183 | 0.345 | 0.155 | 2.243 | 1.55E-02 |
| 828.5475 | 1201 | 4.737 | 0.094 | 5.011 | 0.132 | 0.945 | 1.61E-02 |
| 939.5193 | 1201 | 2.282 | 0.092 | 2.002 | 0.140 | 1.140 | 1.64E-02 |
| 471.2953 | 1201 | 0.759 | 0.197 | 0.328 | 0.136 | 2.317 | 1.68E-02 |
| 858.6202 | 1202 | 2.937 | 0.128 | 2.598 | 0.152 | 1.131 | 1.68E-02 |
| 647.6057 | 1204 | 2.830 | 0.099 | 2.610 | 0.074 | 1.084 | 1.75E-02 |
| 273.9573 | 1101 | 0.000 | 0.000 | 0.230 | 0.150 | 0.000 | 1.79E-02 |
| 703.5709 | 1101 | 2.890 | 0.063 | 2.695 | 0.101 | 1.073 | 1.82E-02 |
| 573.485 | 1203 | 4.750 | 0.113 | 4.450 | 0.139 | 1.067 | 1.85E-02 |
| 300.2098 | 1204 | 2.097 | 0.103 | 1.828 | 0.123 | 1.147 | 1.88E-02 |
| 805.5828 | 1202 | 6.134 | 0.120 | 6.429 | 0.127 | 0.954 | 1.99E-02 |
| 607.5616 | 1203 | 0.757 | 0.254 | 0.226 | 0.163 | 3.349 | 2.01E-02 |
| 632.5761 | 1203 | 1.009 | 0.202 | 0.556 | 0.170 | 1.815 | 2.04E-02 |
| 294.2205 | 1204 | 4.901 | 0.151 | 4.551 | 0.146 | 1.077 | 2.23E-02 |
| 716.4988 | 1204 | 2.371 | 0.109 | 2.106 | 0.119 | 1.126 | 2.25E-02 |
| 677.5763 | 1203 | 1.718 | 0.148 | 1.349 | 0.171 | 1.274 | 2.26E-02 |
| 572.4813 | 1203 | 6.067 | 0.112 | 5.782 | 0.136 | 1.049 | 2.28E-02 |

TABLE 3-continued

Accurate neutral mass features differing between CRC and normal serum ($p < 0.05$, log2 transformed)

| Detected Mass | Analysis Mode | AVG (log2) Normal | Std Error Normal | AVG (log2) CRC | Std Error CRC | Log(2) ratio | P value |
|---|---|---|---|---|---|---|---|
| 745.5663 | 1204 | 2.558 | 0.108 | 2.787 | 0.084 | 0.918 | 2.47E−02 |
| 732.4923 | 1204 | 1.802 | 0.165 | 1.430 | 0.163 | 1.260 | 2.71E−02 |
| 874.8477 | 1102 | 0.276 | 0.120 | 0.055 | 0.045 | 4.969 | 2.73E−02 |
| 464.3874 | 1203 | 0.584 | 0.183 | 0.205 | 0.140 | 2.847 | 2.74E−02 |
| 882.7684 | 1203 | 6.327 | 0.155 | 5.988 | 0.142 | 1.057 | 2.74E−02 |
| 569.3684 | 1102 | 2.360 | 0.124 | 2.045 | 0.160 | 1.154 | 2.81E−02 |
| 615.354 | 1202 | 2.392 | 0.101 | 2.153 | 0.115 | 1.111 | 2.84E−02 |
| 831.5536 | 1201 | 2.439 | 0.366 | 1.588 | 0.398 | 1.536 | 2.88E−02 |
| 297.2386 | 1204 | 2.034 | 0.141 | 1.724 | 0.136 | 1.180 | 2.98E−02 |
| 751.5514 | 1201 | 1.722 | 0.114 | 1.381 | 0.199 | 1.247 | 3.03E−02 |
| 308.2717 | 1204 | 2.288 | 0.128 | 2.557 | 0.112 | 0.895 | 3.09E−02 |
| 883.7727 | 1203 | 5.568 | 0.148 | 5.248 | 0.140 | 1.061 | 3.11E−02 |
| 827.5442 | 1201 | 5.719 | 0.093 | 5.963 | 0.132 | 0.959 | 3.12E−02 |
| 768.5545 | 1204 | 2.082 | 0.117 | 1.786 | 0.157 | 1.166 | 3.15E−02 |
| 832.6028 | 1102 | 1.971 | 0.109 | 1.695 | 0.147 | 1.163 | 3.15E−02 |
| 609.3247 | 1202 | 1.229 | 0.162 | 1.636 | 0.214 | 0.751 | 3.16E−02 |
| 660.6083 | 1203 | 0.312 | 0.152 | 0.045 | 0.044 | 7.005 | 3.17E−02 |
| 832.5788 | 1201 | 5.331 | 0.059 | 5.167 | 0.093 | 1.032 | 3.26E−02 |
| 303.2293 | 1204 | 1.818 | 0.124 | 1.529 | 0.146 | 1.189 | 3.44E−02 |
| 827.545 | 1101 | 2.585 | 0.105 | 2.320 | 0.145 | 1.114 | 3.49E−02 |
| 616.504 | 1201 | 2.171 | 0.146 | 2.461 | 0.114 | 0.882 | 3.49E−02 |
| 615.1693 | 1201 | 1.416 | 0.225 | 0.895 | 0.264 | 1.583 | 3.50E−02 |
| 749.5358 | 1201 | 1.926 | 0.090 | 1.648 | 0.172 | 1.169 | 3.52E−02 |
| 602.472 | 1204 | 2.476 | 0.080 | 2.206 | 0.173 | 1.122 | 3.58E−02 |
| 295.2286 | 1204 | 3.056 | 0.165 | 2.723 | 0.142 | 1.123 | 3.75E−02 |
| 244.2189 | 1203 | 3.033 | 0.067 | 2.898 | 0.058 | 1.047 | 3.80E−02 |
| 622.4973 | 1203 | 2.765 | 0.120 | 2.463 | 0.173 | 1.123 | 3.96E−02 |
| 252.0763 | 1201 | 0.462 | 0.253 | 0.041 | 0.058 | 11.223 | 4.01E−02 |
| 195.0535 | 1202 | 0.293 | 0.181 | 0.000 | 0.000 | 0.293 | 4.16E−02 |
| 467.4052 | 1203 | 0.500 | 0.188 | 0.148 | 0.136 | 3.385 | 4.17E−02 |
| 293.0679 | 1202 | 0.000 | 0.000 | 0.207 | 0.158 | 0.000 | 4.32E−02 |
| 847.5498 | 1201 | 3.490 | 0.057 | 3.344 | 0.088 | 1.044 | 4.48E−02 |
| 592.3569 | 1202 | 2.197 | 0.103 | 1.946 | 0.151 | 1.129 | 4.84E−02 |
| 670.57 | 1204 | 2.170 | 0.133 | 1.827 | 0.214 | 1.188 | 4.85E−02 |
| 447.3848 | 1204 | 0.952 | 0.193 | 0.578 | 0.173 | 1.649 | 4.85E−02 |
| 361.1439 | 1101 | 0.056 | 0.056 | 0.367 | 0.235 | 0.152 | 4.92E−02 |
| 732.5496 | 1201 | 1.909 | 0.155 | 2.217 | 0.150 | 0.861 | 4.98E−02 |
| 732.5496 | 1201 | 2.160 | 0.143 | 1.910 | 0.169 | 1.131 | 0.0498 |

TABLE 4

Retention Times of Seven CRC Biomarkers

| FT Accurate Mass | Formula | Theoretical Mass | Neutral Q-Star Mass | Q Star-Detected Mass | Retention Time (min) |
|---|---|---|---|---|---|
| 446.3406 | C28H46O4 | 446.3406 | 446.40132 | 445.3935 | 16.5 |
| 450.3726 | C28H50O4 | 450.3726 | 450.43052 | 449.4227 | 16.8 |
| 466.3661 | C28H50O5 | 466.36581 | 466.42027 | 465.41245 | 16.5 |
| 468.384 | C28H52O5 | 468.38145 | 468.42562 | 467.4178 | 16.5 |
| 538.4259 | C32H58O6 | 538.42332 | 538.423335 | 537.415515 | 16.4 |
| 592.4711 | C36H64O6 | 592.47026 | 592.521895 | 591.514075 | 16.5 |
| 594.4851 | C36H66O6 | 594.48591 | 594.54482 | 593.537 | 16.8 |

TABLE 5

Structural assignments for the key MS/MS fragments for Biomarker 3, $C_{28}H_{28}O_4$, (448.3726, neutral mass)

| m/z | Formula | Molecular fragment | Fragment loss |
|---|---|---|---|
| (a) 447 | $C_{28}H_{47}O_4$ | 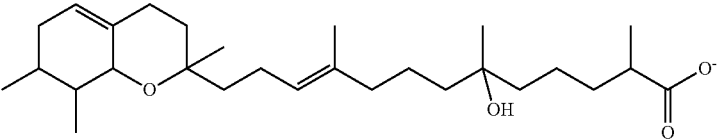 [SMILES: C/C(=C\CCC1(C)CCC2=CCC(C)C(C)C2O1)CCCC(C)(O)CCCC(C)C(=O)[O-]] | -H⁺ |

TABLE 5-continued

Structural assignments for the key MS/MS fragments for Biomarker 3, $C_{28}H_{28}O_4$, (448.3726, neutral mass)

| m/z | Formula | Molecular fragment | Fragment loss |
|---|---|---|---|
| (b) 429 | $C_{28}H_{45}O_3$ | | $-H_2O$ |
| (c) 403 | $C_{27}H_{47}O_2$ | | $-CO_2$ |
| (d) 385 | $C_{27}H_{45}O$ | | $-(CO_2 + H_2O)$ |
| (e) 279 | $C_{18}H_{31}O_2$ | | Ring opening of (d) at C9-O1 and |

TABLE 6

Structural assignments for the key MS/MS fragments for Biomarker 4, $C_{28}H_{48}O_5$, (464.3522, neutral mass).

| m/z | Formula | Molecular fragment | Fragment loss |
|---|---|---|---|
| (a) 463 | $C_{28}H_{47}O_5$ | | $-H^+$ |
| (b) 445 | $C_{28}H_{45}O_4$ | | $-H_2O$ |
| (c) 419 | $C_{27}H_{47}O_3$ | | $-CO_2$ |
| (d) 401 | $C_{27}H_{45}O_2$ | | $-(CO_2 + H_2O)$ |

TABLE 6-continued

Structural assignments for the key MS/MS fragments for Biomarker 4, $C_{28}H_{48}O_5$, (464.3522, neutral mass).

| m/z | Formula | Molecular fragment | Fragment loss |
|---|---|---|---|
| (e) 383 | $C_{27}H_{43}O$ | | $-(CO_2 + 2H_2O)$ |
| (f) 315 | $C_{22}H_{35}O$ | | Ring opening at C9-O1 |
| (g) 297 | $C_{22}H_{33}$ | | F - $H_2O$ |
| (h) 241 | $C_{14}H_{25}O_3$ | | |

TABLE 7

Structural assignments for the key MS/MS fragments for Biomarker 5, $C_{28}H_{46}O_4$, (446.3522, neutral mass)

| m/z | Formula | Molecular fragment | Fragment loss |
|---|---|---|---|
| (a) 445 | $C_{28}H_{45}O_4$ | | $-H^+$ |
| (b) 427 | $C_{28}H_{43}O_3$ | | $-H_2O$ |
| (c) 401 | $C_{27}H_{45}O_2$ | | $-CO_2$ |
| (d) 383 | $C_{27}H_{43}O$ | | $-(CO_2 + H_2O)$ |

TABLE 7-continued

Structural assignments for the key MS/MS fragments for Biomarker 5, $C_{28}H_{46}O_4$, (446.3522, neutral mass)

| m/z | Formula | Molecular fragment | Fragment loss |
|---|---|---|---|
| (e) 223 | $C_{14}H_{23}O_2$ | | (b) - |
| (f) 205 | $C_{14}H_{21}O$ | | |
| (g) 177 | $C_{12}H_{17}O$ | | (f) - $C_2H_8$ |
| (h) 162 | $C_{11}H_{114}O$ | | g - $CH_3$ |

TABLE 8

Structural assignments for the key MS/MS fragments for Biomarker 6, $C_{28}H_{50}O_5$, (466.3661, neutral mass)

| m/z | Formula | Molecular fragment | Fragment loss |
|---|---|---|---|
| (a) 465 | $C_{28}H_{49}O_5$ | | -$H^+$ |
| (b) 447 | $C_{28}H_{47}O_4$ | | -$H_2O$ |
| (c) 433 | $C_{27}H_{45}O_4$ | | -$CH_3OH$ |

TABLE 8-continued

Structural assignments for the key MS/MS fragments for Biomarker 6, $C_{28}H_{50}O_5$, (466.3661, neutral mass)

| m/z | Formula | Molecular fragment | Fragment loss |
|---|---|---|---|
| (d) 421 | $C_{26}H_{45}O_3$ | | $-CO_2$ |
| (e) 405 | $C_{26}H_{45}O_3$ | | (c) - $C_2H_4$ |
| (f) 403 | $C_{27}H_{47}O_2$ | | $-(CO_2 + H_2O)$ |
| (g) 349 | $C_{22}H_{37}O_3$ | | |
| (h) 297 | $C_{18}H_{33}O_3$ | | (b) - |
| (i) 279 | $C_{18}H_{31}O_2$ | | (h) - $H_2O$ |
| (j) 241 | $C_{15}H_{29}O_2$ | | |
| (k) 223 | $C_{13}H_{19}O_3$ | | |

TABLE 8-continued

Structural assignments for the key MS/MS fragments for Biomarker 6, C$_{28}$H$_{50}$O$_5$, (466.3661, neutral mass)

| m/z | Formula | Molecular fragment | Fragment loss |
|---|---|---|---|
| (l) 185 | C$_{13}$H$_{19}$O$_3$ | 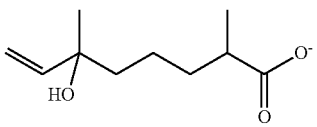 | 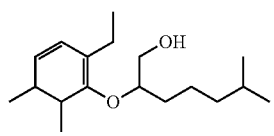 [SMILES: CCC1=C(OC(CO)CCCC(C)C)C(C)C(C)C=C1] |

TABLE 9

Structural assignments for the key MS/MS fragments for Biomarker 7, C$_{28}$H$_{50}$O$_4$, (450.3726, neutral mass)

| m/z | Formula | Molecular fragment | Fragment loss |
|---|---|---|---|
| (a) 449 | C$_{28}$H$_{49}$O$_4$ | 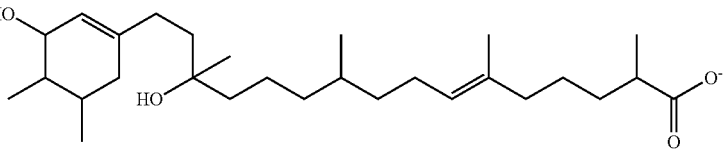 | -H$^+$ |
| (b) 431 | C$_{28}$H$_{49}$O$_4$ | 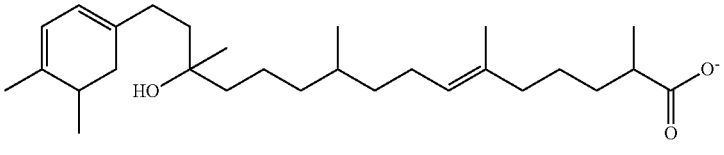 [SMILES: CC1=CC=C(CCC(C)(O)CCCC(C)CC/C=C(\C)CCCC(C)C(=O)[O-])CC1C] | - H$_2$O |
| (c) 417 | C$_{27}$H$_{45}$O$_3$ | 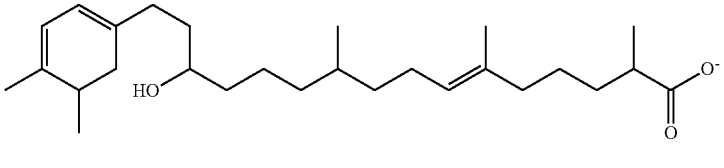 [SMILES: CC1=CC=C(CCC(O)CCCC(C)CC/C=C(\C)CCCC(C)C(=O)[O-])CC1C] | - (H$_2$O + CH$_3$) |
| (d) 413 | C$_{28}$H$_{45}$O$_2$ | 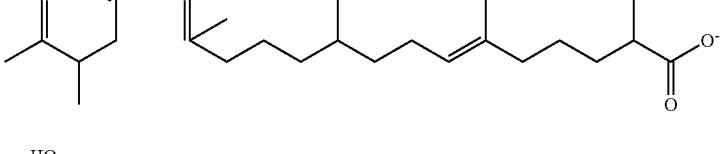 | - 2 × H$_2$O |
| (e) 405 | C$_{27}$H$_{49}$O$_2$ | 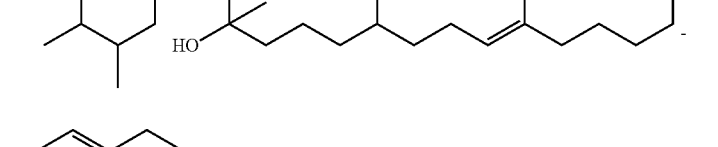 | -CO$_2$ |
| (f) 399 | C$_{27}$H$_{49}$O$_2$ | 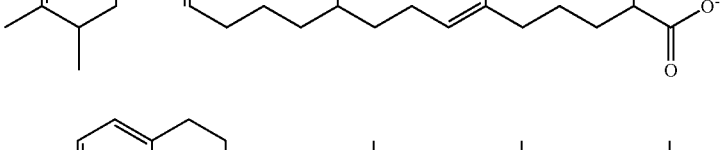 | (e) - H$_2$O |
| (g) 387 | C$_{27}$H$_{47}$O | 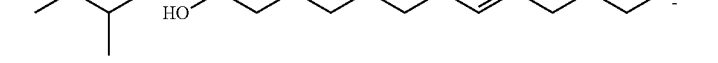 | - (CO$_2$ + H$_2$O) |

TABLE 9-continued

Structural assignments for the key MS/MS fragments for Biomarker 7, $C_{28}H_{50}O_4$, (450.3726, neutral mass)

| m/z | Formula | Molecular fragment | Fragment loss |
|---|---|---|---|
| (h) 371 | $C_{26}H_{43}O$ | | (g) - $CH_4$ |
| (i) 281 | $C_{18}H_{33}O_2$ | | |
| (j) 277 | $C_{19}H_{33}O$ | | (c) - |

TABLE 10

Structural assignments for the key MS/MS fragments for Biomarker 8, $C_{28}H_{52}O_5$, (468.3840, neutral mass)

| m/z | Formula | Molecular fragment | Fragment loss |
|---|---|---|---|
| (a) 467 | $C_{28}H_{51}O_5$ | | $-H^+$ |
| (b) 449 | $C_{28}H_{49}O_4$ | | $-H_2O$ |
| (c) 431 | $C_{28}H_{47}O_3$ | | $-2 \times H_2O$ |
| (d) 423 | $C_{27}H_{51}O_2$ | | $-CO_2$ |

TABLE 10-continued
Structural assignments for the key MS/MS fragments for Biomarker 8, $C_{28}H_{52}O_5$, (468.3840, neutral mass)
| m/z | Formula | Molecular fragment | Fragment loss |
|---|---|---|---|
| (e) 405 | $C_{27}H_{49}O_2$ | 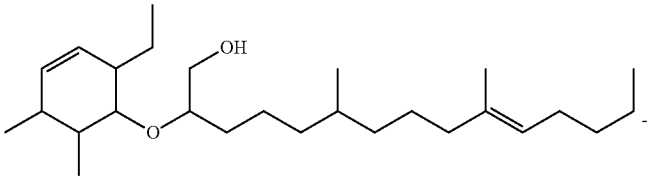 | $-(CO_2 + H_2O)$ |
| (f) 389 | $C_{26}H_{45}O_2$ | 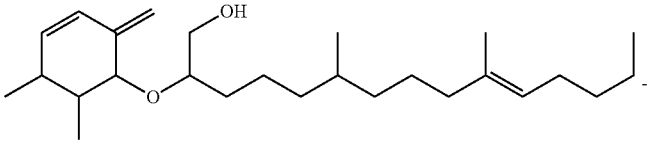 | (e) - $CH_4$ |
| (g) 297 | $C_{17}H_{33}O_3$ | 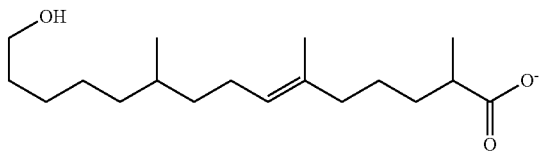 [SMILES: C/C(=C\CCC(C)CCCCCO)CCCC(C)C(=O)[O-]] | (b) - 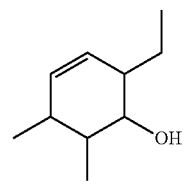 |
| (h) 279 | $C_{18}H_{31}O_2$ | 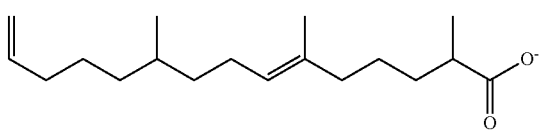 [SMILES: C=CCCCC(C)CC/C=C(\C)CCCC(C)C(=O)[O-]] | (g) - $H_2O$ |
| (i) 263 | $C_{17}H_{27}O_2$ | 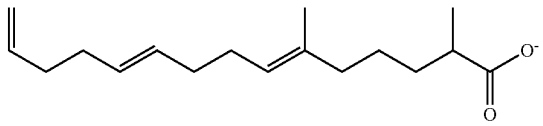 [SMILES: C=CCC/C=C/CC/C=C(\C)CCCC(C)C(=O)[O-]] | (h) - $CH_4$ |
| (i) 215 | $C_{12}H_{23}O_3$ | 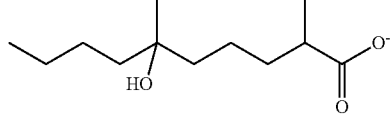 | i, 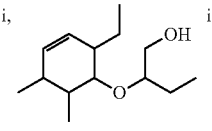 ii, $CH_3$ |
| (j) 187 | $C_{10}H_{19}O_3$ | 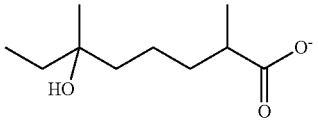 | 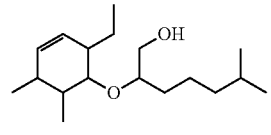 [SMILES: CCC1C=CC(C)C(C)C1OC(CO)CCCC(C)C] |
| (k) 169 | $C_{10}H_{17}O_2$ | 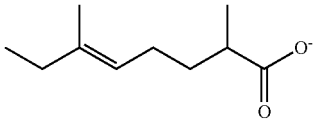 | (J) - $H_2O$ |
| (l) 141 | $C_8H_{13}O_2$ | 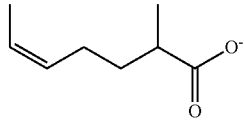 | (k) - $C_2H_4$ |

TABLE 11

$^1$H NMR (500 MHz) chemical shifts (ppm)$^a$, multiplicity and J (Hz)$^b$ of γ-tocopherol (1) and related compounds 3, 4, 5 and 6 in CDCl$_3$.

| H #'s | 1 | 2 | 3 | 4 | 5 | 6 |
|---|---|---|---|---|---|---|
| 1 | — | — | — | — | — | — |
| 2 | — | — | — | — | — | 5.12, m |
| 3 | 1.75, m | 1.95-2.10, m | 1.48-1.59, m | 1.41-1.53, m | 1.82-1.83, m | 1.24-1.25, m |
|   |         |              | 1.78-1.86, m | 1.80-1.83, m | 1.97-2.03, m |              |
| 4 | 2.66, m | 2.69, t | 1.78-1.86, m | 1.80-1.83, m | 1.97-2.03, m | 2.28-2.34, m |
|   |         |         | 1.94-2.01, m | 1.93-1.99, m | 2.23-2.30, m |              |
| 5 | 6.35, s | 6.38, s | 5.33-5.36, m | 1.80-1.83, m | 5.31-5.36, m | 5.25-5.37, m |
|   |         |         |              | 2.21-2.25, m |              |              |
| 6 | — | — | 1.78-1.86, m | 3.69-3.71, m | 5.31-5.36, m | 5.25-5.37, m |
|   |   |   | 1.94-2.01, m |              |              |              |
| 7 |   | — | 1.94-2.01, m | 1.41-1.53, m | — | 1.95-2.02, m |
| 8 | — | — | 2..24-2.31, m | 2.21-2.25, m | 2.74-2.76, m | 2.72-2.75, m |
| 9 | — | — | 4.59-4.62, m | — | 4.58-4.62, m | — |
| 10 | — | — | — | — | — | — |
| 11 | 1.05-1.25, m | 1.79, m | 1.10-1.32, m | 1.08-1.15, m | 1.24-1.36, m | 1.95-2.02, m |
| 12 | 1.05-1.25, m | 1.95-2.10, m | 2.24-2.31, m | 1.93-1.99, m | 1.97-2.03, m | 1.24-1.25, m |
| 13 | 1.05-1.25, m | 5.08-5.14, m | 5.33-5.36, m | 5.33-5.34, m | 5.31-5.36, m | 1.53-1.54, m |
| 14 | 1.32-1.36, m | — | — | — | — | — |
| 15 | 1.05-1.25, m | 1.95-2.10, m | 1.48-1.59, m | 1.41-1.53, m | 1.82-1.83, m | 1.53-1.54, m |
| 16 | 1.05-1.25, m | 1.95-2.10, m | 1.10-1.32, m | 1.08-1.15, m | 1.24-1.36, m | 1.24-1.25, m |
| 17 | 1.05-1.25, m | 5.08-5.14, m | 1.10-1.32, m | 1.23-1.31, m | — | 1.24-1.25, m |
| 18 | 1.32-1.36, m | — | — | 1.80-1.83, m | 1.24-1.36, m | 1.95-2.02, m |
| 19 | 1.05-1.25, m | 1.95-2.10, m | 1.10-1.32, m | 1.23-1.31, m | 1.24-1.36, m | 1.24-1.25, m |
| 20 | 1.05-1.25, m | 1.95-2.10, m | 1.10-1.32, m | 1.08-1.15, m | 1.24-1.36, m | 1.24-1.25, m |
| 21 | 1.05-1.25, m | 5.08-5.14, m | 1.10-1.32, m | 1.23-1.31, m | 1.24-1.36, m | 1.53-1.54, m |
| 22 | 1.32-1.36, m | — | 2..24-2.31, m | 2.21-2.25, m | 2.23-2.30, m | 2.28-2.34, m |
| 23 | 0.81-0.85, m | 1.60, s | — | — | — | — |
| 24 | 0.81-0.85, m | 1.69, s | 0.84-0.88, m | 0.0.83-0.85, m | 0.83-0.90, m | 0.85-0.87, m |
| 25 | 0.81-0.85, m | 1.61, s | 1.00$^c$, s | 0.95$^c$, s | 1.00$^c$, s | 0.85-0.87, m |
| 26 | 0.81-0.85, m | 1.61, s | 1.55, s | 1.53, s | 1.54, s | 1.53-1.54, m |
| 27 | 1.53, s | 1.27, s | 0.91, s | 0.89, s | 0.90, s | a: 4.04-4.14, dd (J = 6.0, 12.0) b: 4.27-4.29, dd (J = 4.0, 12.0) |
| 28 | 2.12, s | 2.13, s | 0.84-0.88, m | 0.0.83-0.85, m | 0.83-0.90, m | 1.24-1.25, m |
| 29 | 2.09, s | 2.14, s | 0.67$^c$, br s | 0.66$^c$, br s | 0.66$^c$, br s | 1.24-1.25, m |

$^a$The signals were determined and assigned from the position of cross peaks in $^1$H-$^1$H COSY, $^1$H-$^1$H homonuclear decoupling, HMQC and HMBC spectra.
$^b$Coupling constants (J) are reported to the nearest 0.5 Hz.
$^c$The assignments may be reversed

TABLE 12

$^{13}$C NMR (125.8 MHz) chemical shifts (ppm)$^a$ of γ tocopherol (1) and related compounds 3, 4, 5 and 6 in CDCl$_3$.

| Carbon # | 1 | 2 | 3 | 4 | 5 | 6 |
|---|---|---|---|---|---|---|
| 1 | — | — | — | — | — | — |
| 2 | 74.5 | 75.2 | 57.2 | 57.3 | 56.7 | 69.7 |
| 3 | 31.7 | 31.4 | 30.2 | 32.4 | 37.0 | 14.9 |
| 4 | 20.8 | 22.3 | 30.1 | 36.3 | 35.8 | 30.1$^b$ |
| 5 | 118.6 | 112.13 | 130.5 | 37.8 | 122.6 | 130.8 |
| 6 | 144.6 | 146.3 | 28.7 | 72.3 | 130.0 | 130.5 |
| 7 | 121.2 | 118.24 | 37.5 | 32.2 | 126.1 | 30.3 |
| 8 | 122.6 | 121.6 | 38.7 | 42.8 | 27.8 | 30.3 |
| 9 | 145.6 | 134.9 | 74.2 | 141.8 | 73.7 | 147.5 |
| 10 | 117.3 | 135.0 | 140.2 | 100.5 | 138.5 | 100.8 |
| 11 | 39.9 | 39.8 | 40.2 | 40.0 | 36.6 | 30.5 |
| 12 | 21.1 | 22.3 | 24.3 | 28.7 | 31.9 | 23.3 |
| 13 | 37.4 | 124.4 | 120.7 | 119.9 | 128.3 | 39.5 |
| 14 | 32.8 | 125.7 | 130.3 | 122.2 | 139.7 | 69.0 |
| 15 | 37.4 | 39.6 | 32.4 | 24.8 | 28.2 | 35.0 |
| 16 | 24.5 | 26.6 | 40.0$^b$ | 19.9$^b$ | 28.0$^b$ | 23.5$^b$ |
| 17 | 37.4 | 124.4 | 37.1$^b$ | 36.7$^b$ | 27.8 | 30.0 |
| 18 | 32.7 | 134.9 | 56.6 | 56.7 | 56.1 | 31.2 |
| 19 | 37.4 | 36.7 | 28.5$^b$ | 40.2$^b$ | 29.0$^b$ | 29.9 |
| 20 | 24.8 | 26.8 | 23.3$^b$ | 23.3$^b$ | 24.3$^b$ | 29.7 |
| 21 | 39.4 | 124.2 | 36.3$^b$ | 28.5$^b$ | 23.8$^b$ | 34.8 |
| 22 | 28.0 | 131.2 | 42.8 | 37.0 | 39.7 | 32.7 |
| 23 | 22.7 | 25.7 | 173.8 | 173.8 | 174.0 | 174.1 |
| 24 | 21.1 | 17.8 | 23.0 | 24.3 | 22.8 | 24.6$^b$ |
| 25 | 19.7 | 16.0 | 19.2$^b$ | 19.2$^b$ | 18.7$^b$ | 26.4 |
| 26 | 19.7 | 15.87 | 19.8 | 23.0 | 22.5 | 28.0$^b$ |
| 27 | 23.8 | 24.5 | 30.1$^b$ | 21.6$^b$ | 21.0$^b$ | 62.9 |
| 28 | 12.1 | 11.9 | 19.2$^b$ | 24.3$^b$ | 193.3$^b$ | 25.7$^b$ |
| 29 | 11.8 | 11.8 | 19.8$^b$ | 12.3$^b$ | 11.8$^b$ | 11.7$^b$ |

$^a$The signals were determined and assigned from the position of cross peaks in HMQC and HMBC spectra.
$^b$The assignments may be reversed

TABLE 13

A. Summary of HTS results including cross-cancer specificities, demographic and disease staging data. B. P-values showing no statistical significance between randomly selected sets of patients based on ethnicity, gender, age, BMI, presence of polyps and staging.

A

| Disease | Normal | CRC | Ovarian | Prostate | Renal Cell | Lung | Breast |
|---|---|---|---|---|---|---|---|
| Sample Size | 288 | 186 | 20 | 24 | 30 | 25 | 25 |
| Average CRC Score** | −0.45 ± 0.076* | −2.31 ± 1.18* | −1.96 ± 0.94* | −0.71 ± 0.56* | −1.10 ± 1.03* | −1.20 ± 0.90* | −0.76 ± 0.71* |
| P-value versus normal | — | 5.40E−68 | 2.00E−16 | 7.00E−02 | 9.60E−06 | 1.80E−06 | 3.20E−02 |
| Predicted CRC Positive (%) | 11.4 | 78.1 | 70.0 | 16.7 | 33.3 | 40.0 | 20.0 |
| Predicted CRC Negative (%) | 88.6 | 21.9 | 30.0 | 83.3 | 66.7 | 60.0 | 80.0 |
| Mean age | 58.7 ± 13.7 | 60.3 ± 14.8 | 60.7 ± 12.8 | 63.1 ± 9.9 | 67.6 ± 12.1 | 61.2 ± 13.0 | 57.7 ± 12.8 |
| Mean BMI | 26.4 ± 5.2 | 23.8 ± 6.0 | 21.5 ± 7.8 | 24.6 ± 4.6 | 24.3 ± 5.8 | 24.0 ± 4.6 | 25.0 ± 6.5 |
| Gender | | | | | | | |
| Male | 157 | 115 | — | 24 | 17 | 11 | — |
| Female | 131 | 71 | 20 | — | 13 | 14 | 25 |
| Ethnicity | | | | | | | |
| Caucasian | 218 | 76 | 13 | 24 | 26 | 22 | 18 |
| Asian/Hispanic | 42 | 101 | 7 | — | 2 | 1 | 3 |
| African American | 20 | 6 | — | — | 24 | 2 | 4 |
| Other | 8 | 3 | — | — | — | — | — |
| Disease Stage | | | | | | | |
| 0 | — | 2 | — | — | — | — | 1 |
| I | — | 25 | 5 | 1 | 14 | 12 | 3 |
| II | — | 79 | — | 12 | 6 | 2 | 13 |
| III | — | 45 | 13 | 8 | 5 | 3 | 4 |
| IV | — | 15 | — | 1 | 2 | 2 | 1 |
| Not Available | — | 20 | 2 | 2 | 3 | 6 | 3 |
| Pathology | — | 186 Adenocarcinoma | 2 Adenocarcinoma 7 Epithelial 8 Papillary 3 Other | 22 Adenocarcinoma 2 Other | 19 Clear Cell 4 Papillary 7 Other | 5 Non-small cell adenocarcinoma 3 Non-small cell carcinoma 5 Carcinoid 3 Small cell 2 Squamous non-small cell 2 Bronchioalveolar Carcinoma 3 Other | 4 Ductal 16 Infiltrating Ductal 2 Lobular 2 Infiltrating Lobular 1 Pagets |
| Polyp Status for CRC | | | | | | | |
| Polyps Present | — | 29 | — | — | — | — | — |
| Polyps Absent | — | 143 | — | — | — | — | — |
| Not Available | — | 14 | — | — | — | — | — |
| Gleason Score | — | — | — | 7.3 | — | — | — |

B

| | Hispanic/Asian vs Caucasian | Male vs Female | Age <60 vs >60 | BMI <25 vs >25 | Polyps Yes vs No | Stage I/II vs III/IV |
|---|---|---|---|---|---|---|
| p-value | 0.3[1] | 0.6[2] | 0.3[3] | 0.2[4] | 0.2[5] | 0.5[6] |

*Standard Deviation
**Based on the lowest mean-normalized ratio among the six biomarker signals
[1] 40 CRC-positive Hispanic/Asian, 40 normal Hispanic/Asian, 40 CRC-positive Causasian and 40 normal Caucasian
[2] ALL subjects
[3] 20 CRC-positive < age 60, 20 normal < age 60, 20 CRC-positive > age 60, 20 normal > age 60
[4] 25 CRC-positive BMI <25, 25 normal BMI <20, 25 CRC-positive BMI >25, 25 normal BMI >25
[5] 29 CRC-positive with polyps, 29 CRC-positive with no polyps
[6] 30 CRC-positive TNM stage I or II, 30 CRC-positive TNM stage III or IV

The invention claimed is:

1. An analytical method for diagnosing a patient's colorectal cancer (CRC) health state, or change in CRC health state, or for diagnosing risk of CRC or the presence of CRC in a patient, comprising the steps of:

a) performing a mass spectrometry assay on at least one blood sample from said patient using a Fourier transform ion cyclotron resonance, time of flight, magnetic sector, quadrupole or triple quadrupole mass spectrometer to obtain a collision induced dissociation (CID)

MS/MS fragmentation pattern for one or more than one metabolite marker and to obtain quantifying data for said one or more than one metabolite marker;

b) generating a result of said mass spectrometry assay, said result comprising at least the presence or absence of a decrease in the level of said one or more than one metabolite marker in said blood sample based on a comparison of said quantifying data for said one or more than one metabolite marker to corresponding data obtained for one or more than one reference blood sample; and c) assigning the patient as having or not having colorectal cancer (CRC), or having or not having a change in CRC health state, or having or not having a risk of CRC, wherein the one or more than one metabolite marker is at least a metabolite having the molecular formula of $C_{28}H_{46}O_4$ and which is characterized by a collision induced dissociation (CID) MS/MS fragmentation pattern using $N_2$ as collision gas and analyzed under negative ionization comprising the following daughter ions: 445, 383, 427, 401, 223, 205, 177 and 162, wherein a decrease in the level of said one or more than one metabolite marker in the blood sample from the patient relative to a reference blood sample indicates that the patient has CRC, a change in CRC, or is at risk of CRC.

2. The method of claim 1, wherein the mass spectrometer is equipped with a chromatographic system.

3. The method of claim 1, wherein the blood sample is a whole blood sample, a subfraction of whole blood, a blood serum sample, or a blood plasma sample.

4. The method of claim 1, wherein a liquid/liquid extraction is performed on the sample whereby non-polar metabolites are dissolved in an organic solvent and polar metabolites are dissolved in an aqueous solvent.

5. The method of claim 4, wherein the extracted samples are analyzed by positive or negative electrospray ionization, positive or negative atmospheric pressure chemical ionization, or combinations thereof.

6. The method of claim 4, wherein the extracted samples are analyzed by MS/MS transition.

7. The method of claim 6, wherein at least one MS/MS transition is identified for the metabolite having the molecular formula of $C_{28}H_{46}O_4$, said at least one MS/MS transition being selected from the group consisting of 445.4/383.4, 445.4/427.4, 445.4/401.4, 445.4/401.4, 445.4/223.2, 445.4/205.2 and combinations thereof.

8. The method of claim 4, wherein the extracted samples are analyzed by extracted ion current (EIC) chromatography and MS/MS transition.

9. The method of claim 1, wherein said one or more than one reference sample is from one or more CRC-negative humans.

10. The method of claim 1, further comprising
performing a mass spectrometry assay on a blood sample from said patient to obtain quantifying data for one or more than one internal standard molecule; and
obtaining a ratio for each of the levels of said one or more than one metabolite marker to the level obtained for the one or more than one internal standard molecule;
wherein step (b) comprises generating said result based on a comparison of each ratio to one or more corresponding ratios obtained for the one or more than one reference blood sample.

11. The method of claim 10, wherein the internal standard molecule is cholic acid.

12. An analytical method for detecting a colorectal cancer (CRC) disease marker, comprising the steps of:
providing at least one blood sample from a patient; and
performing a mass spectrometry assay on the at least one blood sample using a Fourier transform ion cyclotron resonance, time of flight, magnetic sector, quadrupole or triple quadrupole mass spectrometer to obtain a collision induced dissociation (CID) MS/MS fragmentation pattern for one or more than one metabolite marker and to obtain quantifying data for said one or more than one metabolite marker;
wherein the one or more than one metabolite marker is at least $C_{28}H_{46}O_4$, which is characterized by a collision induced dissociation (CID) MS/MS fragmentation pattern using $N_2$ as collision gas and analyzed under negative ionization comprising the following daughter ions: 445, 383, 427, 401, 223, 205, 177 and 162.

\* \* \* \* \*